US009309574B1

(12) United States Patent
Gallo et al.

(10) Patent No.: US 9,309,574 B1
(45) Date of Patent: Apr. 12, 2016

(54) MOLECULAR CLONING OF HIV-1 FROM IMMORTALIZED CELL LINES

(75) Inventors: Robert C. Gallo, Bethesda, MD (US); Flossie Wong-Staal, San Diego, CA (US); Mikulas Popovic, Bethesda, MD (US); Beatrice H. Hahn, Wallingford, PA (US); George M. Shaw, Wallingford, PA (US); Amanda G. Fisher, London (GB)

(73) Assignee: The United States of America as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 08/385,231

(22) Filed: Feb. 8, 1995

Related U.S. Application Data

(63) Continuation of application No. 07/832,603, filed on Feb. 12, 1992, now abandoned, which is a continuation of application No. 07/160,827, filed on Feb. 26, 1988, now abandoned, which is a continuation-in-part of application No. 07/033,891, filed on Apr. 3, 1987, now abandoned, which is a continuation of application No. 06/643,306, filed on Aug. 22, 1984, now abandoned, said application No. 07/160,827 is a continuation-in-part of application No. 06/813,069, filed on Dec. 24, 1985, now abandoned, and a continuation-in-part of application No. 06/693,866, filed on Jan. 23, 1985, which is a continuation-in-part of application No. 06/659,339, filed on Oct. 10, 1984, now abandoned, which is a continuation-in-part of application No. 06/643,306, filed on Aug. 22, 1984, now abandoned.

(51) Int. Cl.
C12Q 1/68 (2006.01)
C12Q 1/70 (2006.01)

(52) U.S. Cl.
CPC .............. *C12Q 1/703* (2013.01); *C12Q 1/6834* (2013.01); *C12Q 1/6876* (2013.01)

(58) Field of Classification Search
USPC ............... 435/235, 252.3, 240.2, 172.3, 69.1, 435/236, 320.1, 91, 91.1, 91.32, 91.4; 536/27
See application file for complete search history.

(56) References Cited

U.S. PATENT DOCUMENTS

| 4,401,756 A | 8/1983 | Gillis |
| 4,520,113 A | 5/1985 | Gallo |
| 4,647,773 A | 3/1987 | Gallo |
| 4,652,599 A | 3/1987 | Gallo |
| 4,665,032 A | 5/1987 | Laurence |
| 4,689,398 A | 8/1987 | Wu |
| 4,692,403 A | 9/1987 | Lindner |
| 4,707,439 A | 11/1987 | Seto |
| 4,716,102 A * | 12/1987 | Levy ................................. 435/5 |
| 4,725,669 A | 2/1988 | Essex |
| 4,738,922 A | 4/1988 | Haseltine |
| 4,743,678 A | 5/1988 | Essex |
| 4,839,288 A | 6/1989 | Montagnier |
| 4,883,813 A | 11/1989 | Maxim |
| 4,886,743 A | 12/1989 | Hood |
| 4,892,865 A | 1/1990 | Townsend |
| 4,910,132 A | 3/1990 | Knight |
| 4,925,784 A | 5/1990 | Crowl |
| 4,931,393 A | 6/1990 | Martin |
| 4,935,372 A | 6/1990 | Goh |
| 4,950,652 A | 8/1990 | Carter |
| 4,957,737 A | 9/1990 | Heimer |
| 4,963,497 A | 10/1990 | Wong-Staal |
| 4,981,790 A | 1/1991 | Haseltine |
| 4,985,249 A | 1/1991 | Sakagami |
| 5,008,182 A | 4/1991 | Sninsky |
| 5,019,510 A | 5/1991 | Wain-Hobson |
| 5,024,940 A | 6/1991 | Brenner |
| 5,025,800 A | 6/1991 | Zelson |
| 5,026,635 A | 6/1991 | Ferguson et al. |
| 5,030,714 A | 7/1991 | Alizon |
| 5,030,718 A | 7/1991 | Montagnier |
| 5,034,511 A | 7/1991 | Alizon |
| 5,039,604 A | 8/1991 | Papsidero |
| 5,043,262 A | 8/1991 | Haseltine |
| 5,047,435 A | 9/1991 | Lavie |
| 5,051,496 A | 9/1991 | Alizon |
| 5,053,509 A | 10/1991 | Antoine |
| 5,055,391 A | 10/1991 | Montagnier |
| 5,063,053 A | 11/1991 | Wong-Staal |
| 5,064,946 A | 11/1991 | Shaver |
| 5,066,579 A | 11/1991 | Reyes |
| 5,066,782 A | 11/1991 | Montagnier |
| 5,070,012 A | 12/1991 | Nolan |
| 5,079,342 A | 1/1992 | Alizon |
| 5,087,557 A | 2/1992 | McClure |

(Continued)

OTHER PUBLICATIONS

Barré-Sinoussi, et al. Science 220 : 868, 1983.*

(Continued)

*Primary Examiner* — Aaron Priest

(74) *Attorney, Agent, or Firm* — Siegfried J. W. Ruppert; Susan S. Rucker

(57) ABSTRACT

Disclosed is the molecular cloning of HTLV-III, the adult leukemia and acquired immune deficiency syndrome (AIDS) virus. Clone BH10 contains a 9.0 Kb viral insert constituting the entire HTLV-III genome. Clones BH8 and BH5 contain viral inserts of 5.5 Kb and 3.5 Kb, respectively. These clones are suitable for the development of diagnostic and therapeutic measures for AIDS, as well as use as probes for the detection of AIDS. By scientific convention, HTLV-III, referred to herein also as HIV, has been renamed as HIV-1.

161 Claims, 16 Drawing Sheets

(56) References Cited

U.S. PATENT DOCUMENTS

| | | | |
|---|---|---|---|
| 5,087,625 A | 2/1992 | Hargrave |
| 5,098,833 A | 3/1992 | Lasky |
| 5,098,927 A | 3/1992 | Takatsuki |
| 5,104,790 A | 4/1992 | Flesher |
| 5,108,904 A | 4/1992 | Landay |
| 5,108,920 A | 4/1992 | Ng |
| 5,109,123 A | 4/1992 | Reinherz |
| 6,531,276 B1 | 3/2003 | Luciw |
| 7,393,949 B1 | 7/2008 | Luciw |
| RE41,158 E | 3/2010 | Luciw |
| 8,329,396 B1 | 12/2012 | Alizon |

OTHER PUBLICATIONS

Popovic, et al. Science 224 : 497, 1984.*
Gelmann, et al. PNAS USA 81 : 993, 1984.*
Stratowa, et al EMBO J. 1(12) : 1573, 1982 Fuisawa, et al. Gene 40 : 23, 1985.*
G.M. Shaw et al (1984) Science 226 : 1165-1171.*
M. Alizon et al (1986) Cell 46 : 63-74.*
Y. Koyanagi et al (1987) Science 236 : 819-822.*
W.A. Haseltine (1991) Science 253 : 366.*
A. G. Fisher et al (1985) Nature 316 : 262-265.*
E. Terwilliger et al (1986) 60 : 754-760.*
Nature-Based Products Examples, attached, available at http://www.uspto.gov/patents/law/exam/mdc_examples_nature-based_products.pdf, accessed Nov. 25, 2015.*
Merriam-Webster (definition of "bind," attached, available at http://beta.merriam-webster.com/dictionary /bind, accessed Nov. 25, 2015).*
George M. Shaw et al., "Molecular Characterization of Human T-Cell Leukemia (Lymphotropic) Virus Type III in the Acquired Immune Deficiency Syndrome," Science, vol. 226, pp. 1165-1171, Dec. 7, 1984.
*Alice Corporation Pty. Ltd. v. CLS Bank International et al.*, U.S. Supreme Court, No. 13-298; Decided Jun. 19, 2014.
*Association for Molecular Pathology et al. v. Myriad Genetics, Inc., et al.*; U.S. Supreme Court, No. 12-398; Decided Jun. 13, 2013.
*Mayo Collaborative Services, DBA Mayo Medical Laboratories, et al. v. Prometheus Laboratories, Inc.*; U.S. Supreme Court, No. 10-1150; Decided Mar. 20, 2012.
*Bilski et al. v. Kappos*, Under Secretary Ofcommerce for Intellectual Property and Director, Patent and Trademark Office; U.S. Supreme Court, No. 08-964; Decided Jun. 28, 2010.
*University of Utah Research Foundation, The Trustees of the University of Pennsylvania, HSC Research and Development Limited Partnership, Endorecherche, Inc., and Myriad Genetics, Inc. v. Ambry Genetics Corporation*; Fed. Cir. 2014-1361, -1366; Decided Dec. 17, 2014.
In Re Roslin Institute (Edinburgh); Fed. Cir. 2013-1407; Decided May 8, 2014.
*Classen Immunotherapies, Inc., v. Biogen Idec, and Glaxosmithkline, and Merck & Co., Inc., and Chiron Corporation, Kaiser-Permanente, Inc., Kaiser Permanente Ventures, Kaiser Permanente International, Kaiser Permanente Insurance Company, The Permanente Federation, LLC, The Permanente Company, LLC, The Permanente Foundation, The Permanente Medical Group, Inc., Kaiser Foundation Hospitals, Kaiser Foundation Added Choice Health Plan, Inc., and Kaiser Foundation Health Plan Inc.*; Fed. Cir. 2006-1634,-1649; Decided Aug. 31, 2011.
U.S. Appl. No. 06/693,866, filed Jan. 23, 1985, Chang.
Alizon M., etal.; "Genetic Variability of the AIDS Virus: Nucleotide Sequence Analysis of Two Isolates from African Patients"; *Cell*, vol. 225, Aug. 31, 1984; pp. 927-930.
Arya S.K., et al.; "Homology of Genome of AIDS-Associated Virus with Genomes of Human T-Cell Leukemia Viruses"; *Science*, vol. 225, Aug. 31, 1984; pp. 927-930.
Barre-Sinoussi, F. etal.; "Isolation of a T-Lymphotropic retrovirus from a Patient at Risk for Acquired Immune Deficiency Syndrome (AIDS)"; Science, vol. 220, May 20, 1983; pp. 868-870.
Chang, N.T., et al.; :Expression in *Escherichia coli* of Open Reading Frame Gene Segments of HTLV-III; Science., vol. 228, 1985; pp. 93-96.
Dowbenko D.J., et al.; "Bacterial expression of the acquired immunodeficiency syndrome retrovirus p24 gag protein and its use as a diagnostic reagent"; *Proc. Natl. Acad. Sci. USA.*, vol. 82, Nov. 1985; pp. 7748-7752.
Essex M.; "Adult T-Cell Leukemia-Lymphoma: Role of a Human Retrovirus"; *Journal of National Cancer Institute*, vol. 69, No. 4, Oct. 4, 1982; pp. 981-985.
Feorino P.M., et al.; "Lymphadenopathy associated virus infection of a blood donor-recipient pair with acquired immunodeficiency syndrome"; *Science.*, vol. 225, Jul. 6, 1984; pp. 69-72.
Fisher, A.G., et al.; "A molecular clone of HTLV-III with biological activity"; *Nature.*, vol. 316, Jul. 18, 1985; pp. 262-265.
Fujisawa Y., et al.; "Expression of hepatitis B virus surface antigen P31 gene in *Escherichia coli*"; Gene., vol. 40, 1985; pp. 23-29.
Gelmann, E.P.; "Molecular cloning of a unique human T-cell leukemia virus (HTLV-II$_{Mo}$)"; Proc. Nat!. Acad. Sci. USA., vol. 81, Feb. 1984; pp. 993-997.
Genbank: K02011.1; "HIV-1 isolate BH8 tat protein and rev protein genes, partial cds; vpu protein and envelope protein precursor, genes, complete cds; and long terminal repeat, partial sequence"; http://www.ncbi.nlm.nih.gov/nuccore/327466, Jul. 9,1999; 4 pages.
Genbank: K02012.1; "Human immunodeficiency virus type 1, isolate BH5, gag, pol vif, and vpr genes"; http://www.ncbi.nlm.nih.gov/nuccore/327459, Aug. 2, 1993; 5 pages.
Genbank: M15654.1; "Human immunodeficiency virus type 1, isolate BH10, genome"; http://www.ncbi.nlm.nih.gov/nuccore/326383, Aug. 2, 2006; 7 pages.
Hahn, B.H., et al.; "Molecular cloning and characterization of the HTLV-III virus associated with AIDS";*Nature.*, vol. 312, Nov. 8, 1984; pp. 166-169.
Haseltine, W.A.; "HIV Research and nef Alleles"; *Science*, vol. 253, 1991; p. 366.
Klatzmann D., et al.; "T-Iymphocyte T4 molecule behaves as the receptor for human retrovirus LAV"; *Nature.*, vol. 312, Dec. 20, 1984; pp. 767-768.
Koyanagi Y., et al.; "Dual Infection of the Central Nervous System by AIDS Viruses with Distinct Cellular Tropisms"; *Science*, vol. 236, May 15, 1987; pp. 819-822.
Manzari V., et al.; "Human T-cell leukemia-lymphoma virus (HTLV): cloning of an integrated defective provirus and flanking cellular sequences"; *Proc. Nat!. Acad. Sci. USA*, vol. 80, No. 12, Jun. 1, 1983; pp. 1574-1578.
Marx J.L.; "A Virus by Any Other Name . . ."; *Science, Mar. 22, 1985; in AIDS Papers from Science*, 1982-1985, ed. Ruth Kulstad, 1986, pp. 450-454.
Merriam Webster; (definition of "bind," available at http://beta.merriam-webster.com/dictionary/bind, accessed Nov. 25, 2015).
Muesing, M.A., et al.; "Nucleic acid structure and expression of the human AIDS/lymphadenopathy retrovirus"; *Nature.*, vol. 313, Feb. 7, 1985; pp. 450-458.
Nature-Based Products Examples; available at http://www.uspto.gov/patents/law/exam/mdc-examples-nature-based-products.pdf, accessed Nov. 25, 2015.
Patent Interference No. 105,291; "Decision-Priority—BD.R. 125(a)"; Sep. 28, 2007; 33 pages.
Patent Interference No. 105,291; "Judgment—Merits—BD.R. 127"; Sep. 28, 2007; 3 pages.
Popopvic M. et al.; "Detection, Isolation, and Continuous Production of Cytopathic Retroviruses (HTLV-III) from Patients with Aids and Pre-AIDS"; *Science.*, vol. 224, May 4, 1984; pp. 497-500.
Ratner, L., etal.; "Complete nucleotide sequence of the AIDS virus, HTLV-III"; *Nature.*, vol. 313, Jan. 24, 1985; pp. 277-284.
Seiki M., et al.; "Human adult T-cell leukemia virus: molecular cloning of the provirus DNA and the unique terminal structure"; *Proc. Natl. Acad. Sci.* USA, vol. 79, No. 22, Nov. 1, 1982; pp. 6899-6902.
Seiki M., et al.; "Human adult T-cell leukemia virus: complete nucleotide sequence of the provirus genome integrated in leukemia cell DNA"; *Proc. Natl. Acad. Sci. USA*, vol. 80, No. 12, Jun. 1, 1983; pp. 3618-3622.

(56) References Cited

OTHER PUBLICATIONS

Shaw, G.M., etal.; "Molecular Characterization of Human T-Cell Leukemia (Lymphotropic) Virus Type III in the Acquired Immune Deficiency Syndrome"; *Science.*, vol. 226, Dec. 7, 1984; pp. 1165-1171.

Stratowa C. al.; "Recombinant retroviral DNA yielding high expression of hepatitis B surface antigen"; *EMBO J.*, vol. 1 No. 12, 1982; pp. 1573-1578.

Terwilliger E., et al; "Effects of Mutations within the 3' orf Open Reading Frame Region of Human T-Cell Lymphotropic Virus Type III (HTLV-III/LAV) on Replication and Cytopathogenicity"; *J. Virol.*, vol. 60, No. 2, Nov. 1986; pp. 754-760.

*Ariosa Diagnostics, Inc., Natera, Inc., DNA Diagnostics Center, Inc., v. Sequenom, Inc., Sequenom Center for Molecular Medicine, LLC, ISIS Innovation Limited*; Fed Cir. 2014-1139, 2014-1144; Decided: Jun. 12, 2015 (2015).

*Ariosa Diagnostics, Inc., Natera, Inc., DNA Diagnostics Center, Inc., v. Sequenom, Inc., Sequenom Center for Molecular Medicine, LLC, ISIS Innovation Limited*; Fed Cir. 2014-1139, 2014-1144; Decided: Dec. 2, 2015 (2015).

\* cited by examiner

| | |
|---|---|
| GAGCTCTCTCGACGCAGGACTCGGCTTGCTGAAGCGCGCACGGCAAGAGGCGAGGGGCGG | 60 |
| CGACTGGTGAGTACGCCAAAAATTTTGACTAGCGGAGGCTAGAAGGAGAGAGATGGGTGC | 120 |
| GAGAGCGTCAGTATTAAGCGGGGGAGAATTAGATCGATGGGAAAAAATTCGGTTAAGGCC | 180 |
| AGGGGGAAAGAAAAAATATAAATTAAAACATATAGTATGGGCAAGCAGGGAGCTAGAACG | 240 |
| ATTCGCAGTTAATCCTGGCCTGTTAGAAACATCAGAAGGCTGTAGACAAATACTGGGACA | 300 |
| GCTACAACCATCCCTTCAGACAGGATCAGAAGAACTTAGATCATTATATAATACAGTAGC | 360 |
| AACCCTCTATTGTGTGCATCAAAGGATAGAGATAAAAGACACCAAGGAAGCTTTAGACAA | 420 |
| GATAGAGGAAGAGCAAAACAAAAGTAAGAAAAAAGCACAGCAAGCAGCAGCTGACACAGG | 480 |
| ACACAGCAGTCAGGTCAGCCAAAATTACCCTATAGTGCAGAACATCCAGGGGCAAATGGT | 540 |
| ACATCAGGCCATATCACCTAGAACTTTAAATGCATGGGTAAAAGTAGTAGAAGAGAAGGC | 600 |
| TTTCAGCCCAGAAGTAATACCCATGTTTTCAGCATTATCAGAAGGAGCCACCCCACAAGA | 660 |
| TTTAAACACCATGCTAAACACAGTGGGGGGACATCAAGCAGCCATGCAAATGTTAAAAGA | 720 |
| GACCATCAATGAGGAAGCTGCAGAATGGGATAGAGTGCATCCAGTGCATGCAGGGCCTAT | 780 |
| CGCACCAGGCCAGATGAGAGAACCAAGGGGAAGTGACATAGCAGGAACTACTAGTACCCT | 840 |
| TCAGGAACAAATAGGATGGATGACAAATAATCCACCTATCCCAGTAGGAGAAATTTATAA | 900 |
| AAGATGGATAATCCTGGGATTAAATAAAATAGTAAGGATGTATAGTCCTACCAGCATTCT | 960 |
| GGACATAAGACAAGGACCAAAGGAACCCTTTAGAGACTATGTAGACCGGTTCTATAAAAC | 1020 |
| TCTAAGAGCCGAGCAAGCTTCACAGGAAGTAAAAAATTGGATGACAGAAACCTTGTTGGT | 1080 |
| CCAAAATGCGAACCCAGATTGTAAGACTATTTTAAAAGCATTGGGACCAGCAGCTACTCT | 1140 |
| AGAAGAAATGATGACAGCATGTCAGGGAGTGGGAGGACCCGGCCATAAAGCAAGAGTTTT | 1200 |
| GGCTGAAGCAATGAGCCAAGTAACAAATTCAACTACCATAATGATGCAAAGAGGCAATTT | 1260 |
| TAGGAACCAAAGAAAGATTGTTAAGTGTTTCAATTGTGGCAAAGAAGGGCACATAGCAAG | 1320 |
| AAATTGCAAGGCCCCTAGAAAAAGAGGCTGTTGGAAATGTGGAAAGGAAGGACACCAAAT | 1380 |
| GAAAGATTGTACTGAGAGACAGGCTAATTTTTTAGGGAAGATCTGGCCTTCCTACAAGGG | 1440 |
| AAGGCCAGGGAATTTTCTTCAGAGCAGACCAGAGCCAACAGCCCCACCATTTCTTCAGAG | 1500 |
| CAGACCAGAGCCAACAGCCCCACCAGAAGAGAGCTTCAGGTCTGGGGTAGAGACAACAAC | 1560 |
| TCCCTCTCAGAAGCAGGAGCCGATAGACAAGGAACTGTATCCTTTAACTTCCCTCAGATC | 1620 |
| ACTCTTTGGCAACGACCCCTCGTCACAATAAAGATAGGGGGCAACTAAAGGAAGCTCTA | 1680 |
| TTAGATACAGGAGCAGATGATACAGTATTAGAAGAAATGAGTTTGCCAGGAAGATGGAAA | 1740 |
| CCAAAAATGATAGGGGGAATTGGAGGTTTTATCAAAGTAAGACAGTATGATCAGATACTC | 1800 |
| ATAGAAATCTGTGGACATAAAGCTATAGGTACAGTATTAGTAGGACCTACACCTGTCAAC | 1860 |
| ATAATTGGAAGAAATCTGTTGACTCAGATTGGTTGCACTTTAAATTTTCCCATTAGTCCT | 1920 |
| ATTGAAACTGTACCAGTAAAATTAAAGCCAGGAATGGATGGCCCAAAAGTTAAACAATGG | 1980 |
| CCATTGACAGAAGAAAAAATAAAAGCATTAGTAGAAATTTGTACAGAAATGGAAAAGGAA | 2040 |
| GGGAAAATTTCAAAAATTGGGCCTGAAAATCCATACAATACTCCAGTATTTGCCATAAAG | 2100 |

FIG. 5

```
AAAAAAGACAGTACTAAATGGAGAAAATTAGTAGATTTCAGAGAACTTAATAGGAGAACT        2160
CAAGACTTCTGGGAAGTTCAATTGGGAATACCACATCCCGCAGGGTTAAAAAAGAAAAAA        2220
TCAGTAACAGTACTGGATGTGGGTGATGCATATTTTTCAGTTCCCTTAGATGAAGACTTC        2280
AGGAAGTATACTGCATTTACCATACCTAGTATAAATAATGAGACACCAGGGATTAGATAT        2340
CAGTACAATGTGCTTCCACAGGGATGGAAAGGATCACCAGCAATATTCCAAAGTAGCATG        2400
ACAAAAATCTTAGAGCCTTTTAGAAAACAAAATCCAGACATAGTTATCTATCAATACATG        2460
GATGATTTGTATGTAGGATCTGACTTAGAAATAGGGCAGCATAGAACAAAAATAGAGGAG        2520
CTGAGACAACATCTGTTGAGGTGGGGATTTACCACACCAGACAAAAAACATCAGAAAGAA        2580
CCTCCATTCCTTTGGATGGGTTATGAACTCCATCCTGATAAATGGACAGTACAGCCTATA        2640
GTGCTGCCAGAAAAAGACAGCTGGACTGTCAATGACATACAGAAGTTAGTGGGAAAATTG        2700
AATTGGGCAAGTCAGATTTATCCAGGGATTAAAGTAAGGCAATTATGTAAACTCCTTAGA        2760
GGAACCAAAGCACTAACAGAAGTAATACCACTAACAGAAGAAGCAGAGCTAGAACTGGCA        2820
GAAAACAGAGAGATTCTAAAAGAACCAGTACATGGAGTGTATTATGACCCATCAAAAGAC        2880
TTAATAGCAGAAATACAGAAGCAGGGGCAAGGCCAATGGACATATCAAATTTATCAAGAG        2940
CCATTTAAAAATCTGAAAACAGGAAAATATGCAAGAATGAGGGGTGCCCACACTAATGAT        3000
GTAAAACAATTAACAGAGGCAGTGCAAAAAATAACCACAGAAAGCATAGTAATATGGGGA        3060
AAGACTCCTAAATTTAAACTACCCATACAAAAAGAAACATGGGAAACATGGTGGACAGAG        3120
TATTGGCAAGCCACCTGGATTCCTGAGTGGGAGTTTGTTAATACCCCTCCTTTAGTGAAA        3180
TTATGGTACCAGTTAGAGAAAGAACCCATAGTAGGAGCAGAAACCTTCTATGTAGATGGG        3240
GCAGCTAGCAGGGAGACTAAATTAGGAAAAGCAGGATATGTTACTAATAGAGGAAGACAA        3300
AAAGTTGTCACCCTAACTGACACAACAAATCAGAAGACTGAATTACAAGCAATTCATCTA        3360
GCTTTGCAGGATTCGGGATTAGAAGTAAATATAGTAACAGACTCACAATATGCATTAGGA        3420
ATCATTCAAGCACAACCAGATAAAAGTGAATCAGAGTTAGTCAATCAAATAATAGAGCAG        3480
TTAATAAAAAAGGAAAAGGTCTATCTGGCATGGGTACCAGCACACAAAGGAATTGGAGGA        3540
AATGAACAAGTAGATAAATTAGTCAGTGCTGGAATCAGGAAAATACTATTTTTAGATGGA        3600
ATAGATAAGGCCCAAGAAGAACATGAGAAATATCACAATAATTGGAGAGCAATGGCTAGT        3660
GATTTTAACCTGCCACCTGTAGTAGCAAAAGAAATAGTAGCCAGCTGTGATAAATGTCAG        3720
CTAAAAGGAGAAGCCATGCATGGACAAGTAGACTGTAGTCCAGGAATATGGCAACTAGAT        3780
TGTACACATTTAGAAGGAAAAGTTATCCTGGTAGCAGTTCATGTAGCCAGTGGATATATA        3840
GAAGCAGAAGTTATTCCAGCAGAAACAGGGCAGGAAACAGCATATTTTCTTTTAAAATTA        3900
GCAGGAAGATGGCCAGTAAAAACAATACATACAGACAATGGCAGCAATTTCACCAGTGCT        3960
ACGGTTAAGGCCGCCTGTTGGTGGGCGGGAATCAAGCAGGAATTTGGAATTCCCTACAAT        4020
CCCCAAAGTCAAGGAGTAGTAGAATCTATGAATAAAGAATTAAAGAAAATTATAGGACAG        4080
GTAAGAGATCAGGCTGAACATCTTAAGACAGCAGTACAAATGGCAGTATTCATCCACAAT        4140
TTTAAAAGAAAAGGGGGGATTGGGGGGTACAGTGCAGGGGAAAGAATAGTAGACATAATA        4200
```

FIG. 5 (continued)

```
GCAACAGACATACAAACTAAAGAATTACAAAAACAAATTACAAAAATTCAAAATTTTCGG      4260
GTTTATTACAGGGACAGCAGAAATCCACTTTGGAAAGGACCAGCAAAGCTCCTCTGGAAA      4320
GGTGAAGGGGCAGTAGTAATACAAGATAATAGTGACATAAAAGTAGTGCCAAGAAGAAAA      4380
GCAAAGATCATTAGGGATTATGGAAAACAGATGGCAGGTGATGATTGTGTGGCAAGTAGA      4440
CAGGATGAGGATTAGAACATGGAAAAGTTTAGTAAAACACCATATGTATGTTTCAGGGAA      4500
AGCTAGGGGATGGTTTTATAGACATCACTATGAAAGCCCTCATCCAAGAATAAGTTCAGA      4560
AGTACACATCCCACTAGGGGATGCTAGATTGGTAATAACAACATATTGGGGTCTGCATAC      4620
AGGAGAAAGAGACTGGCATTTGGGTCAGGGAGTCTCCATAGAATGGAGGAAAAGGAGATA      4680
TAGCACACAAGTAGACCCTGAACTAGCAGACCAACTAATTCATCTGTATTACTTTGATTG      4740
TTTTTCAGACTCTGCTATAAGAAAGGCCTTATTAGGACACATAGTTAGCCCTAGGTGTGA      4800
ATATCAAGCAGGACATAACAAGGTAGGATCTCTACAATACTTGGCACTAGCAGCATTAAT      4860
AACACCAAAAAAGGGAAAGCCACCTTTGCCTAGTGTTACGAAACTGACAGAGGATAGATG      4920
GAACAAGCCCCAGAAGACCAAGGGCCACAGAGGGAGCCACACAATGAATGGACACTAGAG      4980
CTTTTAGAGGAGCTTAAGAATGAAGCTGTTAGACATTTTCCTAGGATTTGGCTCCATGGC      5040
TTAGGGCAACATATCTATGAAACTTATGGGGATACTTGGGCAGGAGTGGAAGCCATAATA      5100
AGAATTCTGCAACAACTGCTGTTTATCCATTTTCAGAATTGGGTGTCGACATAGCAGAAT      5160
AGGCGTTACTCAACAGAGGAGAGCAAGAAATGGAGCCAGTAGATCCTAGACTAGAGCCCT      5220
GGAAGCATCCAGGAAGTCAGCCTAAAACTGCTTGTACCACTTGCTATTGTAAAAAGTGTT      5280
GCTTTCATTGCCAAGTTTGTTTCATAACAAAAGCCTTAGGCATCTCCTATGGCAGGAAGA      5340
AGCGGAGACAGCGACGAAGAGCTC
```

FIG. 5 (continued)

| | |
|---|---|
| TGGAAGGGCTAATTCACTCCCAACGAAGACAAGATATCCTTGATCTGTGGATCCACCACA | 60 |
| CACAAGGCTACTTCCCTGATTGGCAGAACTACACACCAGGGCCAGGAGTCAGATATCCAC | 120 |
| TGACCTTTGGATGGTGCTACAAGCTAGTACCAGTTGAGCCAGAGAAGTAAGAAGAAGCCA | 180 |
| ATAAAGGAGAGAACACCAGCTTGTTACACCCTGTGAGCCTGCATGGAATTGATGACCCGG | 240 |
| AGAGAGAAGTGTTAGAGTGGAGGTTTGACAGCCGCCTAGCATTTCATCACATGGCCCGAG | 300 |
| AGCTGCATCCGGAGTACTTCAAGAACTGCTGACATCGAGCTTGCTACAAGGGACTTTCCG | 360 |
| CTGGGGACTTTCCAGGGAGGCGTGGCCTGGGCGGGACTGGGGAGTGGCGAGCCCTCAGAT | 420 |
| CCTGCATATAAGCAGCTGCTTTTTGCCTGTACTGGGTCTCTCTGGTTAGACCAGATCTGA | 480 |
| GCCTGGGAGCTCGAGCTCATCGAAGCAGTCAGACTCATCAAGTTTCTCTATCAAAGCAGT | 540 |
| AAGTAGTACATGTAATGCAACCTATACAAATAGCAATAGTAGCATTAGTAGTAGCAATAA | 600 |
| TAATAGCAATAGTTGTGTGGTCCATAGTAATCATAGAATATAGGAAAATATTAAGACAAA | 660 |
| GAAAAATAGACAGGTTAATTGATAGACTAATAGAAAGAGCAGAAGACAGTGGCAATGAGA | 720 |
| GTGAAGGAGAAATATCAGCACTTGTGGAGATGGGGGTGGAGATGGGGCACCATGCTCCTT | 780 |
| GGGATGTTGATGATCTGTAGTGCTACAGAAAAATTGTGGGTCACAGTCTATTTAGGGGTA | 840 |
| CCTGTGTGGAAGGAAGCAACCACCACTCTATTTTGTGCATCAGATGCTAAAGCATATGAT | 900 |
| ACAGAGGTACATAATGTTTGGGCCACACATGCCTGTGTACCCACAGACCCCAACCCACAA | 960 |
| GAAGTAGTATTGGTAAATGTGACAGAAAATTTTAACATGTGGAAAAATGACATGGTAGAA | 1020 |
| CAGATGCATGAGGATATAATCAGTTTATGGGATCAAAGCCTAAAGCCATGTGTAAAATTA | 1080 |
| ACCCCACTCTGTGTTAGTTTAAAGTGCACTGATTTGAAGAATGATACTAATACCAATAGT | 1140 |
| AGTAGCGGGAGAATGATAATGGAGAAAGGAGAGATAAAAAACTGCTCTTTCAATATCAGC | 1200 |
| ACAAGCAAAAGAGGTAAGGTGCAGAAAGAATATGCATTTTTTTATAAACTTGATATAATA | 1260 |
| CCAATAGATAATGATACTACCAGCTATACGTTGACAAGTTGTAACACCTCAGTCATTACA | 1320 |
| CAGGCCTGTCCAAAGGTATCCTTTGAGCCAATTCCCATACATTATTGTGCCCCGGCTGGT | 1380 |
| TTTGCGATTCTAAAATGTAATAATAAGACGTTCAATGGAACAGGACCATGTACAAATGTC | 1440 |
| AGCACAGTACAATGTACACATGGAATTAGGCCAGTAGTATCAACTCAACTGCTGTTAAAT | 1500 |
| GGCAGTCTAGCAGAAGAAGAGGTAGTAATTAGATCTGTCAATTTCACGGACAATGCTAAA | 1560 |
| ACCATAATAGTACAGCTGAACACATCTGTAGAAATTAATTGTACAAGACCCAACAACAAT | 1620 |
| ACAAGAAAAAGTATCCAAATCCAGAGGGGACCAGGGAGAGCATTTGTTACAATAGGAAAA | 1680 |
| ATAGGAAATATGAGACAAGCACATTGTAACATTAGTAGAGCAAAATGGAATGCCACTTTA | 1740 |
| AAACAGATAGATAGCAAATTAAGAGAACAATTTGGAAATAATAAAACAATAATCTTTAAG | 1800 |
| CAGTCCTCAGGAGGGGACCCAGAAATTGTAACGCACAGTTTTAATTGTGGAGGGGAATTT | 1860 |
| TTCTACTGTAATTCAACACAACTGTTTAATAGTACTTGGAGTACTAAAGGGTCAAATAAC | 1920 |
| ACTGAAGGAAGTGACACAATCACCCTCCCATGCAGAATAAAACAAATTATAAACATGTGG | 1980 |
| CAGGAAGTAGGAAAAGCAATGTATGCCCCTCCCATCAGTGGACAAATTAGATGTTCATCA | 2040 |
| AATATTACAGGGCTGCTATTAACAAGAGATGGTGGTAATAGCAACAATGAGTCCGAGATC | 2100 |

FIG. 6

```
TTCAGACCTGGAGGAGGAGATATGAGGGACAATTGGAGAAGTGAATTATATAAATATAAA    2160
GTAGTAAAAATTGAACCATTAGGAGTAGCACCCACCAAGGCAAAGAGAAGAGTGGTGCAG    2220
AGAGAAAAAAGAGCAGTGGGAATAGGAGCTTTGTTCCTTGGGTTCTTGGGAGCAGCAGGA    2280
AGCACTATGGGCGCAGCGTCAATGACGCTGACGGTACAGGCCAGACAATTATTGTCTGGT    2340
ATAGTGCAGCAGCAGAACAATTTGCTGAGGGCTATTGAGGGCCAACAGCATCTGTTGCAA    2400
CTCACAGTCTGGGGCATCAGCAGCTCCAGGCAAGAATCCTGGCTGTGGAAAGATACCTAA    2460
AGGATCAACAGCTCCTGGGGATTTGGGGTTGCTCTGGAAAACTCATTTGCACCACTGCTG    2520
TGCCTTGGAATGCTAGTTGGAGTAATAAATCTCTGGAACAGATTTGGAATAACATGACCT    2580
GGATGGAGTGGGACAGAGAAATTAACAATTACACAAGCTTAATACACTCCTTAATTGAAG    2640
AATCGCAAAACCAGCAAGAAAAGAATGAACAAGAATTATTGGAATTAGATAAATGGGCAA    2700
GTTTGTGGAATTGGTTTAACATAACAAATTGGCTGTGGTATATAAAATTATTCATAATGA    2760
TAGTAGGAGGCTTGGTAGGTTTAAGAATAGTTTTTGCTGTACTTTCTATAGTGAATAGAG    2820
TTAGGCAGGGATATTCACCATTATCGTTTCAGACCCACCTCCCAAACCCGAGGGGACCCG    2880
ACAGGCCCGAAGGAATAGAAGAAGAAGGTGGAGAGAGAGACAGAGACAGATCCATTCGAT    2940
TAGTGAACGGATCCTTAGCACTTATCTGGGACGATCTGCGGAGCCTGTGCCTCTTCAGCT    3000
ACCACCGCTTGAGAGACTTACTCTTGATTGTAACGAGGATTGTGGAACTTCTGGGACGCA    3060
GGGGGTGGGAAGCCCTCAAATATTGGTGGAATCTCCTACAGTATTGGAGTCAGGAACTAA    3120
AGAATAGTGCTGTTAACTTGCTCAATGCCACAGCCATAGCAGTAGCTGAGGGGACAGATA    3180
GGGTTATAGAAGTATTACAAGCAGCTTATAGAGCCATTCGCCACATACCTAGAAGAATAA    3240
GACAGGGCTTGGAAAGGATTTTGCTATAAGATGGGTGGCAAGTGGTCAAAAAGTAGTGTG    3300
GTTGGATGGCCTGCTGTAAGGGAAAGAATGAGACGAGCTGAGCCAGCAGCAGATGGGGTG    3360
GGAGCAGTATCTCGAGACCTAGAAAAACATGGAGCAATCACAAGTAGCAATACAGCAGCT    3420
ACCAATGCTGATTGTGCTTGGCTAGAAGCACAAGAGGAGGAGGAGGTGGGTTTTCCAGTC    3480
ACACCTCAGGTACCTTTAAGACCAATGACTTACAAGGCAGCTGTAGATCTTAGCCACTTT    3540
TTAAAAGAAAAGGGGGGACTGGAAGGGCTAATTCACTCCCAACGAAGACAAGATATCCTT    3600
GATCTGTGGATCCACCACACACAAGGCTACTTCCCTGATTGGCAGAACTACACACCAGGG    3660
CCAGGGATCAGATATCCACTGACCTTTGGATGGTGCTACAAGCTAGTACCAGTTGAGCCA    3720
GAGAAGATAGAAGAAGCCAATAAAGGAGAGAACACCAGCTTGTTACACCCTGTGAGCCTG    3780
CATGGGATGGATGACCCTGAGAGAGAAGTGTTAGAGTGGAGGTTTGACAGCCGCCTAGCA    3840
TTTCATCACATGGCCCGAGAGCTGCATCCGGAGTACTTCAAGAACTGCTGACATCGAGCT    3900
TGCTACAAGGGACTTTCCGCTGGGGACTTTGCGTGGCCTGGGCGGGACTGGGGAGTGGCG    3960
AGCCCTCAGATCCTGCATATAATTTTTGCCTGTACTGGGTCTCTCTGGTTAGACCAGATC    4020
TGAGCCTGGGAGCTC
```

FIG. 6 (continued)

```
TGGAAGGGCTAATTCACTCCCAACGAAGACAAGATATCCTTGATCTGTGGATCTACCACA      60
CACAAGGCTACTTCCCTGATTAGCAGAACTACACACCAGGGCCAGGGATCAGATATCCAC     120
TGACCTTTGGATGGTGCTACAAGCTAGTACCAGTTGAGCCAGAGAAGTTAGAAGAAGCCA     280
ACAAAGGAGAGAACACCAGCTTGTTACACCCTGTGAGCCTGCATGGAATGGATGACCCGG     240
AGAGAGAAGTGTTAGAGTGGAGGTTTGACAGCCGCCTAGCATTTCATCACATGGCCCGAG     300
AGCTGCATCCGGAGTACTTCAAGAACTGCTGACATCGAGCTTGCTACAAGGGACTTTCCG     360
CTGGGGACTTTCCAGGGAGGCGTGGCCTGGGCGGGACTGGGGAGTGGCGAGCCCTCAGAT     420
CCTGCATATAAGCAGCTGCTTTTTGCCTGTACTGGGTCTCTCTGGTTAGACCAGATCTGA     480
GCCTGGGAGCTCGAGCTCTCTCGACGCAGGACTCGGCTTGCTGAAGCGCGCACGGCAAGA     540
GGCGAGGGGCGGCGACTGGTGAGTACGCCAAAAATTTTGACTAGCGGAGGCTAGAAGGAG     600
AGAGATGGGTGCGAGAGCGTCAGTATTAAGCGGGGGAGAATTAGATCGATGGGAAAAAAT     660
TCGGTTAAGGCCAGGGGGAAAGAAAAAATATAAATTAAAACATATAGTATGGGCAAGCAG     720
GGAGCTAGAACGATTCGCAGTTAATCCTGGCCTGTTAGAAACATCAGAAGGCTGTAGACA     780
AATACTGGGACAGCTACAACCATCCCTTCAGACAGGATCAGAAGAACTTAGATCATTATA     840
TAATACAGTAGCAACCCTCTATTGTGTGCATCAAAGGATAGAGATAAAAGACACCAAGGA     900
AGCTTTAGACAAGATAGAGGAAGAGCAAAACAAAAGTAAGAAAAAAGCACAGCAAGCAGC     960
AGCTGACACAGGACACAGCAGTCAGGTCAGCCAAAATTACCCTATAGTGCAGAACATCCA    1020
GGGGCAAATGGTACATCAGGCCATATCACCTAGAACTTTAAATGCATGGGTAAAAGTAGT    1080
AGAAGAGAAGGCTTTCAGCCCAGAAGTAATACCCATGTTTTCAGCATTATCAGAAGGAGC    1140
CACCCCACAAGATTTAAACACCATGCTAAACACAGTGGGGGGACATCAAGCAGCCATGCA    1200
AATGTTAAAAGAGACCATCAATGAGGAAGCTGCAGAATGGGATAGAGTACATCCAGTGCA    1260
TGCAGGGCCTATTGCACCAGGCCAGATGAGAGAACCAAGGGGAAGTGACATAGCAGGAAC    1320
TACTAGTACCCTTCAGGAACAAATAGGATGGATGACAAATAATCCACCTATCCCAGTAGG    1440
AGAAATTTATAAAAGATGGATAATCCTGGGATTAAATAAAATAGTAAGAATGTATAGCCC    1500
TACCAGCATTCTGGACATAAGACAAGGACCAAAAGAACCTTTTAGAGACTATGTAGACCG    1560
GTTCTATAAAACTCTAAGAGCCGAGCAAGCTTCACAGGAGGTAAAAAATTGGATGACAGA    1620
AACCTTGTTGGTCCAAAATGCGAACCCAGATTGTAAGACTATTTTAAAAGCATTGGGACC    1680
AGCGGCTACACTAGAAGAAATGATGACAGCATGTCAGGGAGTAGGAGGACCCGGCCATAA    1740
GGCAAGAGTTTTGGCTGAAGCAATGAGCCAAGTAACAAATACAGCTACCATAATGATGCA    1800
GAGAGGCAATTTTAGGAACCAAAGAAAGATGGTTAAGTGTTTCAATTGTGGCAAAGAAGG    1860
GCACACAGCCAGAAATTGCAGGGCCCCTAGGAAAAAGGGCTGTTGGAAATGTGGAAAGGA    1920
AGGACACCAAATGAAAGATTGTACTGAGAGACAGGCTAATTTTTTAGGGAAGATCTGGCC    1980
TTCCTACAAGGGAAGGCCAGGGAATTTTCTTCAGAGCAGACCAGAGCCAACAGCCCCACC    2040
ATTTCTTCAGAGCAGACCAGAGCCAACAGCCCCACCAGAAGAGAGCTTCAGGTCTGGGGT    2100
AGAGACAACAACTCCCCCTCAGAAGCAGGAGCCGATAGACAAGGAACTGTATCCTTTAAC    2160
```

FIG. 7

```
TTCCCTCAGATCACTCTTTGGCAACGACCCCTCGTCACAATAAAGATAGGGGGCAACTA        2220
AAGGAAGCTCTATTAGATACAGGAGCAGATGATACAGTATTAGAAGAAATGAGTTTGCCA        2280
GGAAGATGGAAACCAAAAATGATAGGGGGAATTGGAGGTTTTATCAAAGTAAGACAGTAT        2340
GATCAGATACTCATAGAAATCTGTGGACATAAAGCTATAGGTACAGTATTAGTAGGACCT        2400
ACACCTGTCAACATAATTGGAAGAAATCTGTTGACTCAGATTGGTTGCACTTTAAATTTT        2460
CCCATTAGCCCTATTGAGACTGTACCAGTAAAATTAAAGCCAGGAATGGATGGCCCAAAA        2520
GTTAAACAATGGCCATTGACAGAAGAAAAAATAAAAGCATTAGTAGAAATTTGTACAGAA        2580
ATGGAAAAGGAAGGGAAAATTTCAAAAATTGGGCCTGAGAATCCATACAATACTCCAGTA        2640
TTTGCCATAAAGAAAAAAGACAGTACTAAATGGAGAAAATTAGTAGATTTCAGAGAACTT        2700
AATAAGAGAACTCAAGACTTCTGGGAAGTTCAATTAGGAATACCACATCCCGCAGGGTTA        2760
AAAAAGAAAAAATCAGTAACAGTACTGGATGTGGGTGATGCATATTTTTCAGTTCCCTTA        2820
GATGAAGACTTCAGGAAGTATACTGCATTTACCATACCTAGTATAAACAATGAGACACCA        2880
GGGATTAGATATCAGTACAATGTGCTTCCACAGGGATGGAAAGGATCACCAGCAATATTC        2940
CAAAGTAGCATGACAAAAATCTTAGAGCCTTTTAAAAAACAAAATCCAGACATAGTTATC        3000
TATCAATACATGGATGATTTGTATGTAGGATCTGACTTAGAAATAGGGCAGCATAGAACA        3060
AAAATAGAGGAGCTGAGACAACATCTGTTGAGGTGGGGACTTACCACACCAGACAAAAAA        3120
CATCAGAAAGAACCTCCATTCCTTTGGATGGGTTATGAACTCCATCCTGATAAATGGACA        3180
GTACAGCCTATAGTGCTGCCAGAAAAAGACAGCTGGACTGTCAATGACATACAGAAGTTA        3240
GTGGGGAAATTGAATTGGGCAAGTCAGATTTACCCAGGGATTAAAGTAAGGCAATTATGT        3300
AAACTCCTTAGAGGAACCAAAGCACTAACAGAAGTAATACCACTAACAGAAGAAGCAGAG        3360
CTAGAACTGGCAGAAAACAGAGAGATTCTAAAAGAACCAGTACATGGAGTGTATTATGAC        3420
CCATCAAAAGACTTAATAGCAGAAATACAGAAGCAGGGGCAAGGCCAATGGACATATCAA        3480
ATTTATCAAGAGCCATTTAAAAATCTGAAAACAGGAAAATATGCAAGAATGAGGGGTGCC        3540
CACACTAATGATGTAAAACAATTAACAGAGGCAGTGCAAAAAATAACCACAGAAAGCATA        3600
GTAATATGGGGAAAGACTCCTAAATTTAAACTACCCATACAAAAGGAAACATGGGAAACA        3600
TGGTGGACAGAGTATTGGCAAGCCACCTGGATTCCTGAGTGGGAGTTTGTTAATACCCCT        3660
CCTTTAGTGAAATTATGGTACCAGTTAGAGAAAGAACCCATAGTAGGAGCAGAAACCTTC        3720
TATGTAGATGGGGCAGCTAACAGGGAGACTAAATTAGGAAAAGCAGGATATGTTACTAAC        3780
AAAGGAAGACAAAAGGTTGTCCCCCTAACTAACACAACAAATCAGAAAACTGAGTTACAA        3840
GCAATTTATCTAGCTTTGCAGGATTCAGGATTAGAAGTAAACATAGTAACAGACTCACAA        3900
TATGCATTAGGAATCATTCAAGCACAACCAGATAAAAGTGAATCAGAGTTAGTCAATCAA        3960
ATAATAGAGCAGTTAATAAAAAAGGAAAAGGTCTATCTGGCATGGGTACCAGCACACAAA        4020
GGAATTGGAGGAAATGAACAAGTAGATAAATTAGTCAGTGCTGGAATCAGGAAAATACTA        4080
TTTTTAGATGGAATAGATAAGGCCCAAGATGAACATGAGAAATATCACAGTAATTGGAGA        4140
GCAATGGCTAGTGATTTTAACCTGCCACCTGTAGTAGCAAAAGAAATAGTAGCCAGCTGT        4200
GATAAATGTCAGCTAAAAGGAGAAGCCATGCATGGACAAGTAGACTGTAGTCCAGGAATA        4260
```

FIG. 7 (continued)

| | |
|---|---|
| TGGCAACTAGATTGTACACATTTAGAAGGAAAAGTTATCCTGGTAGCAGTTCATGTAGCC | 4320 |
| AGTGGATATATAGAAGCAGAAGTTATTCCAGCAGAAACAGGGCAGGAAACAGCATATTTT | 4380 |
| CTTTTAAAATTAGCAGGAAGATGGCCAGTAAAAACAATACATACAGACAATGGCAGCAAT | 4440 |
| TTCACCAGTGCTACGGTTAAGGCCGCCTGTTGGTGGGCGGGAATCAAGCAGGAATTTGGA | 4500 |
| ATTCCCTACAATCCCCAAAGTCAAGGAGTAGTAGAATCTATGAATAAAGAATTAAAGAAA | 4560 |
| ATTATAGGACAGGTAAGAGATCAGGCTGAACATCTTAAGACAGCAGTACAAATGGCAGTA | 4620 |
| TTCATCCACAATTTTAAAAGAAAAGGGGGGATTGGGGGGTACAGTGCAGGGGAAAGAATA | 4680 |
| GTAGACATAATAGCAACAGACATACAAACTAAAGAATTACAAAAACAAATTACAAAAATT | 4740 |
| CAAAATTTTCGGGTTTATTACAGGGACAGCAGAAATCCACTTTGGAAAGGACCAGCAAAG | 4800 |
| CTCCTCTGGAAAGGTGAAGGGGCAGTAGTAATACAAGATAATAGTGACATAAAAGTAGTG | 4860 |
| CCAAGAAGAAAAGCAAAGATCATTAGGGATTATGGAAAACAGATGGCAGGTGATGATTGT | 4920 |
| GTGGCAAGTAGACAGGATGAGGATTAGAACATGGAAAAGTTTAGTAAAACACCATATGTA | 4980 |
| TGTTTCAGGGAAAGCTAGGGGATGGTTTTATAGACATCACTATGAAAGCCCTCATCCAAG | 5040 |
| AATAAGTTCAGAAGTACACATCCCACTAGGGGATGCTAGATTGGTAATAACAACATATTG | 5100 |
| GGGTCTGCATACAGGAGAAAGAGACTGGCATTTGGGTCAGGGAGTCTCCATAGAATGGAG | 5160 |
| GAAAAGAGATATAGCACACAAGTAGACCCTGAACTAGCAGACCAACTAATTCATCTGTA | 5220 |
| TTACTTTGACTGTTTTTCAGACTCTGCTATAAGAAAGGCCTTATTAGGACACATAGTTAG | 5280 |
| CCCTAGGTGTGAATATCAAGCAGGACATAACAAGGTAGGATCTCTACAATACTTGGCACT | 5340 |
| AGCAGCATTAATAACACCAAAAAAGATAAAGCCACCTTTGCCTAGTGTTACGAAACTGAC | 5400 |
| AGAGGATAGATGGAACAAGCCCCAGAAGACCAAGGGCCACAGAGGGAGCCACACAATGAA | 5460 |
| TGGACACTAGAGCTTTTAGAGGAGCTTAAGAATGAAGCTGTTAGACATTTTCCTAGGATT | 5520 |
| TGGCTCCATGGCTTAGGGCAACATATCTATGAAACTTATGGGGATACTTGGGCAGGAGTG | 5580 |
| GAAGCCATAATAAGAATTCTGCAACAACTGCTGTTTATCCATTTTCAGAATTGGGTGTCG | 5640 |
| ACATAGCAGAATAGGCGTTACTCGACAGAGGAGAGCAAGAAATGGAGCCAGTAGATCCTA | 5700 |
| GACTAGAGCCCTGGAAGCATCCAGGAAGTCAGCCTAAAACTGCTTGTACCAATTGCTATT | 5760 |
| GTAAAAGTGTTGCTTTCATTGCCAAGTTTGTTTCATAACAAAAGCCTTAGGCATCTCCT | 5820 |
| ATGGCAGGAAGAAGCGGAGACAGCGACGAAGACCTCCTCAAGGCAGTCAGACTCATCAAG | 5880 |
| TTTCTCTATCAAAGCAGTAAGTAGTACATGTAATGCAACCTATACAAATAGCAATAGTAG | 5940 |
| CATTAGTAGTAGCAATAATAATAGCAATAGTTGTGTGGTCCATAGTAATCATAGAATATA | 6000 |
| GGAAAATATTAAGACAAAGAAAAATAGACAGGTTAATTGATAGACTAATAGAAAGAGCAG | 6060 |
| AAGACAGTGGCAATGAGAGTGAAGGAGAAATATCAGCACTTGTGGAGATGGGGGTGGAGA | 6120 |
| TGGGGCACCATGCTCCTTGGGATGTTGATGATCTGTAGTGCTACAGAAAATTGTGGGTC | 6180 |
| ACAGTCTATTATGGGGTACCTGTGTGGAAGGAAGCAACCACCACTCTATTTTGTGCATCA | 6240 |
| GATGCTAAAGCATATGATACAGAGGTACATAATGTTTGGGCCACACATGCCTGTGTACCC | 6300 |
| ACAGACCCCAACCCACAAGAAGTAGTATTGGTAAATGTGACAGAAAATTTTAACATGTGG | 6360 |
| AAAAATGACATGGTAGAACAGATGCATGAGGATATAATCAGTTTATGGGATCAAAGCCTA | 6420 |

FIG. 7 (continued)

```
AAGCCATGTGTAAAATTAACCCCACTCTGTGTTAGTTTAAAGTGCACTGATTTGAAGAAT        6480
GATACTAATACCAATAGTAGTAGCGGGAGAATGATAATGGAGAAAGGAGAGATAAAAAAC        6540
TGCTCTTTCAATATCAGCACAAGCATAAGAGGTAAGGTGCAGAAAGAATATGCATTTTTT        6600
TATAAACTTGATATAATACCAATAGATAATGATACTACCAGCTATACGTTGACAAGTTGT        6660
AACACCTCAGTCATTACACAGGCCTGTCCAAAGGTATCCTTTGAGCCAATTCCCATACAT        6720
TATTGTGCCCCGGCTGGTTTTGCGATTCTAAAATGTAATAATAAGACGTTCAATGGAACA        6780
GGACCATGTACAAATGTCAGCACAGTACAATGTACACATGGAATTAGGCCAGTAGTATCA        6840
ACTCAACTGCTGTTAAATGGCAGTCTAGCAGAAGAAGAGGTAGTAATTAGATCTGCCAAT        6900
TTCACAGACAATGCTAAAACCATAATAGTACAGCTGAACCAATCTGTAGAAATTAATTGT        6960
ACAAGACCCAACAACAATACAAGAAAAAGTATCCGTATCCAGAGAGGACCAGGGAGAGCA        7020
TTTGTTACAATAGGAAAATAGGAAATATGAGACAAGCACATTGTAACATTAGTAGAGCA        7080
AAATGGAATAACACTTTAAAACAGATAGATAGCAAATTAAGAGAACAATTTGGAAATAAT        7140
AAAACAATAATCTTTAAGCAGTCCTCAGGAGGGGACCCAGAAATTGTAACGCACAGTTTT        7200
AATTGTGGAGGGGAATTTTTCTACTGTAATTCAACACAACTGTTTAATAGTACTTGGTTT        7260
AATAGTACTTGGAGTACTAAAGGGTCAAATAACACTGAAGGAAGTGACACAATCACCCTC        7320
CCATGCAGAATAAAACAAATTATAAACATGTGGCAGGAAGTAGGAAAAGCAATGTATGCC        7380
CCTCCCATCAGTGGACAAATTAGATGTTCATCAAATATTACAGGGCTGCTATTAACAAGA        7440
GATGGTGGTAATAGCAACAATGAGTCCGAGATCTTCAGACCTGGAGGAGGAGATATGAGG        7500
GACAATTGGAGAAGTGAATTATATAAATATAAAGTAGTAAAAATTGAACCATTAGGAGTA        7560
GCACCCACCAAGGCAAAGAGAAGAGTGGTGCAGAGAGAAAAAAGAGCAGTGGGAATAGGA        7620
GCTTTGTTCCTTGGGTTCTTGGGAGCAGCAGGAAGCACTATGGGCGCAGCGTCAATGACG        7680
CTGACGGTACAGGCCAGACAATTATTGTCTGGTATAGTGCAGCAGCAGAACAATTTGCTG        7740
AGGGCTATTGAGGCGCAACAGCATCTGTTGCAACTCACAGTCTGGGGCATCAAGCAGCTC        7800
CAGGCAAGAATCCTGGCTGTGGAAAGATACCTAAAGGATCAACAGCTCCTGGGGATTTGG        7860
GGTTGCTCTGGAAAACTCATTTGCACCACTGCTGTGCCTTGGAATGCTAGTTGGAGTAAT        7920
AAATCTCTGGAACAGATTTGGAATAACATGACCTGGATGGAGTGGGACAGAGAAATTAAC        7980
AATTACACAAGCTTAATACACTCCTTAATTGAAGAATCGCAAAACCAGCAAGAAAAGAAT        8040
GAACAAGAATTATTGGAATTAGATAAATGGGCAAGTTTGTGGAATTGGTTTAACATAACA        8100
AATTGGCTGTGGTATATAAAATTATTCATAATGATAGTAGGAGGCTTGGTAGGTTTAAGA        8160
ATAGTTTTTGCTGTACTTTCTGTAGTGAATAGAGTTAGGCAGGGATATTCACCATTATCG        8220
TTTCAGACCCACCTCCCAATCCCGAGGGGACCCGACAGGCCCGAAGGAATAGAAGAAGAA        8280
GGGGAGAGAGAGACAGAGACAGATCCATTCGATTAGTGAACGGATCCTTAGCACTTATCT        8340
GGGACGATCTGCGGAGCCTGTGCCTCTTCAGCTACCACCGCTTGAGAGACTTACTCTTGA        8400
TTGTAACGAGGATTGTGGAACTTCTGGGACGCAGGGGGTGGGAAGCCCTCAAATATTGGT        8460
GGAATCTCCTACAGTATTGGAGTCAGGAGCTAAAGAATAGTGCTGTTAGCTTGCTCAATG        8520
CCACAGCTATAGCAGTAGCTGAGGGGACAGATAGGGTTATAGAAGTAGTACAAGGAGCTT        8580
```

FIG. 7 (continued)

```
ATAGAGCTATTCGCCACATACCTAGAAGAATAAGACAGGGCTTGGAAAGGATTTTGCTAT      8640
AAGATGGGTGGCAAGTGGTCAAAAAGTAGTGTGGTTGGATGGCCTGCTGTAAGGGAAAGA      8700
ATGAGACGAGCTGAGCCAGCAGCAGATGGGGTGGGAGCAGCATCTCGAGACCTAGAAAAA      8760
CATGGAGCAATCACAAGTAGCAACACAGCAGCTAACAATGCTGATTGTGCCTGGCTAGAA      8820
GCACAAGAGGAGGAGGAGGTGGGTTTTCCAGTCACACCTCAGGTACCTTTAAGACCAATG      8880
ACTTACAAGGCAGCTGTAGATCTTAGCCACTTTTTAAAAGAAAAGGGGGACTGGAAGGG       8940
CTAATTCACTCCCAACGAAGACAAGATATCCTTGATCTGTGGATCTACCACACACAAGGC     9000
TACTTCCCTGATTAGCAGAACTACACACCAGGGCCAGGGATCAGATATCCACTGACCTTT     9060
GGATGGTGCTACAAGCTAGTACCAGTTGAGCCAGAGAAGTTAGAAGAAGCCAACAAAGGA     9120
GAGAACACCAGCTTGTTACACCCTGTGAGCCTGCATGGAATGGATGACCCGGAGAGAGAA     9180
GTGTTAGAGTGGAGGTTTGACAGCCGCCTAGCATTTCATCACATGGCCCGAGAGCTGCAT    9240
CCGGAGTACTTCAAGAACTGCTGACATCGAGCTTGCTACAAGGGACTTTCCGCTGGGGAC    9300
TTTCCAGGAGGCGTGGCCTGGGCGGGACTGGGGAGTGGCGAGCCCTCAGATCCTGCATAT    9360
AAGGAGCTGCTTTTTGCCTGTACTGGGTCTCTCTGGTTAGACCAGATCTGAGCCTGGGAG    9420
CTC
```

FIG. 7 (continued)

MOLECULAR CLONING OF HIV-1 FROM IMMORTALIZED CELL LINES

REFERENCE TO RELATED APPLICATIONS

This application, Ser. No. 08/385,231, filed Feb. 8, 1995, is a file wrapper continuation of patent application Ser. No. 07/832,603, filed Feb. 12, 1992, now abandoned, which is a file wrapper continuation of patent application Ser. No. 07/160,827, filed Feb. 26, 1988, now abandoned, which is (i) a continuation-in-part of patent application Ser. No. 07/033,891, filed Apr. 3, 1987, now abandoned, which is a continuation of patent application Ser. No. 06/643,306, filed Aug. 22, 1984, now abandoned, (ii) a continuation-in-part of patent application Ser. No. 06/693,866, filed Jan. 23, 1985, pending, which is a continuation-in-part of patent application Ser. No. 06/659,339, filed Oct. 10, 1984, now abandoned, which is a continuation-in-part of patent application Ser. No. 06/643,306, filed Aug. 22, 1984, now abandoned, and (iii) a continuation-in-part of patent application Ser. No. 06/813,069, filed Dec. 24, 1985, now abandoned, the disclosures of which are incorporated herein by reference in their entirety for all purposes.

TERMINOLOGY

The causative agent of acquired immune deficiency syndrome (AIDS) has been known as human T-lymphotropic virus type III (HTLV-III) and as human immunodeficiency virus (HIV). The virus, in accord with the newer practice, will be called HIV except in some instances where a deposit relating to the organism has been made using the earlier terminology.

BRIEF DESCRIPTION OF THE INVENTION

The cultivation of viruses using molecular clones provides a dependable source of virus for study of the natural virus and for preparation of diagnostic and immunogenic products of the virus. The isolation of virus believed to be the causative agent of AIDS was reported by Barre-Sinoussi, et al. in *Science*, Vol. 220, at pages 868-870 (1983). However, no reproduction of the virus in an immortalized cell line is disclosed in that publication. HIV is highly cytopathic to the cells which it infects in nature. This is one characteristic which differentiates HIV from related retroviruses such as HTLV-I and HTLV-II. HIV is further characterized by variation of its genome in nature. Gallo, et al. discovered cell lines useful for continuous production of the virus. The use of such cell lines which are CD-4 positive cells was disclosed in U.S. patent application Ser. No. 06/652,599, which issued as U.S. Pat. No. 4,652,599. The disclosure of that patent is incorporated herein by reference. The disclosure herein provides means for producing clones of virus which are grown in the immortalized cell lines.

The infectious clones of the inventions are useful for producing specific viral proteins in both eukaryotic and prokaryotic systems for use in diagnostic evaluation and for vaccine development. The infectious clones also provide a source of homogeneous viral particles for use in evaluation of vaccines. While HXB2 and HXB3 were shown to be non-infectious or only mildly infectious, infectious clones which have been derived therefrom are disclosed. Transfection of the derivative clones into bacteria provides a means for amplifications of the genome of these clones.

It is the object of this invention to provide a reliable source of HIV, viral particles, proteins, and antibodies by preparation of clones containing essentially the entire genome of the HIV. The virus or viral fragments produced in immortalized cell lines are useful as probes to detect HIV viral sequences in HIV strains isolated from patients. By use of such probes the variant strains of HIV can be studied as a means of determining source of the disease in an individual. Such determination of source is vital in evaluating means of transmission of this disease.

It is a further object of the invention to provide reliable sources of viral products for use as immunogens and diagnostic agents.

BACKGROUND OF THE INVENTION

The characterization of HIV as the causative agent of AIDS by Barre-Sinoussi, et al. [*Science*, Vol. 220 (1983)] did not provide enablement for producing the virus in vitro. However, it was discovered by workers in this laboratory that the causative agent of AIDS could be grown in immortalized CD-4 positive cell lines to provide a reliable source of the virus and viral products. The use of these products as diagnostic tools is disclosed in U.S. Pat. No. 4,520,113, which is incorporated herein by reference.

A method of cloning human T-cell leukemia-lymphoma virus (HTLV), a transforming virus which lacks both the variability and cytopathic properties of HIV, is taught in Manzari, et al., [Proc. Natl. Acad. Sci., Vol. 80, pages 1574-1577 (1983)]. There is no teaching of how to clone a highly cytopathic virus of such diverse genomic structure as the HIV. To obtain a virus for cloning, it was necessary to have an infected, immortalized cell line from which to extract the virus. U.S. Pat. No. 4,652,599 to Gallo, et al. teaches such cell lines.

DESCRIPTION OF THE FIGURES

FIG. 5 represents the entire nucleotide sequence of the molecular clone BH5 (ATCC #40126), which is approximately one half of a cloned genomic sequence for an HIV strain on deposit with the American Type Culture Collection.

FIG. 6 represents the entire nucleotide sequence of the molecular clone BH8 (ATCC #40127), which is approximately the second half of the genomic sequence for the HIV strain noted in FIG. 5.

FIG. 7 represents the entire nucleotide sequence of the molecular clone BH10 (ATCC #40125), which is approximately the entire cloned genomic sequence of an HIV strain, different from the strain noted in FIGS. 5 and 6, on deposit with the American Type Culture Collection.

DETAILED DESCRIPTION OF THE INVENTION

Clones are prepared using both unintegrated DNA and integrated DNA proviral DNA. The clones of integrated DNA and unintegrated DNA are similar, but are distinguishable by differences in several restriction cleavage sites. From FIG. 8, it is shown λBH-10 and λBH-5/λBH-8 are incomplete viral clones which lack a short SstI-SstI segment of approximately 190 base pairs in the 5' LTR-leader sequence as a consequence of use of Sst I in their cloning. The λHXB-2 and λHXB-3 clones contain full-length integrated provirus [~10 kilobases (kb)] with cellular flanking sequences.

Plasmids are constructed using λHXB-2 to produce pHXB-2D A 12.7 kb XbaI fragment derived from pHXB-2D was inserted into the XbaI site in the polylinker of plasmid pSP62 to provide a plasmid suitable for transfection into the DH-1 bacteria.

Preparation of Clones λBH10, λBH5, and λBH8

Example 1

Figure 1:
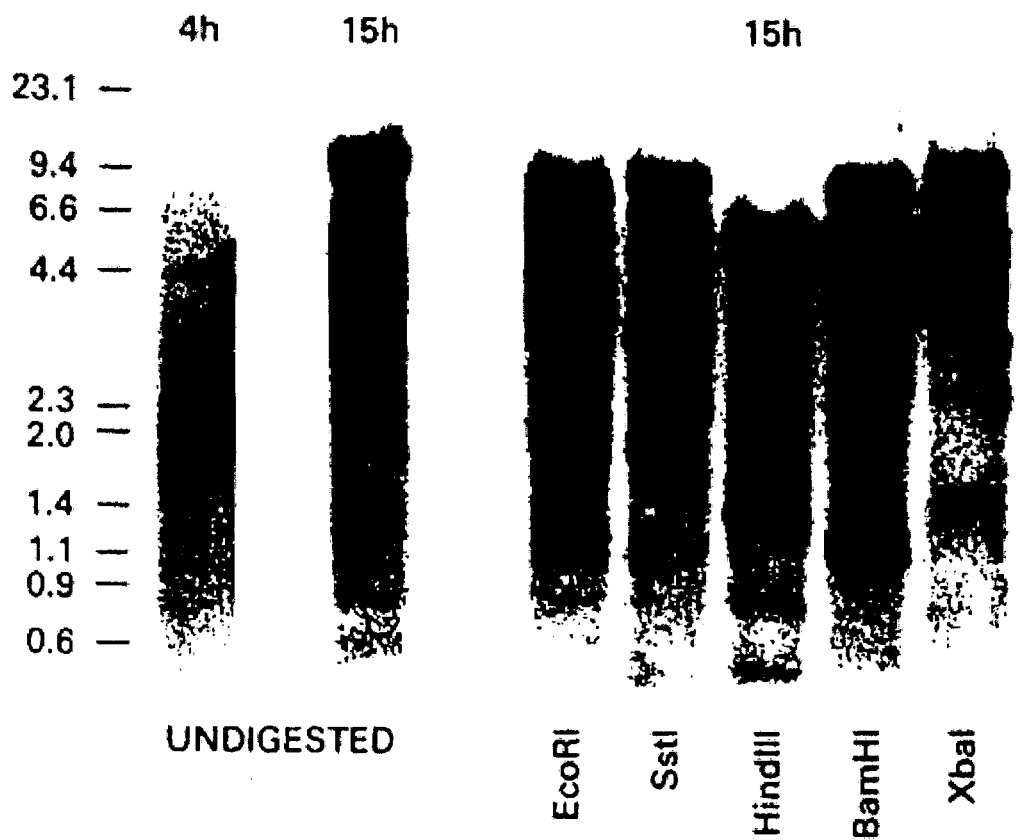
FIG. 1 is a Southern blot analysis of unintegrated DNA of HIV. No viral sequences could be detected in the undigested DNA after 4 hours. However, a major species of viral DNA of approximately 10 kb length was present in the 10, 15, 24 and 48 hour harvest representing the linear unintegrated form of the virus. A representative Southern blot of the 15 hour harvest digested with several restriction enzymes is shown in this figure. Methods: $8 \times 10^8$ fresh uninfected H9 cells were infected with concentrated supernatant from cell line H9/HTLV-III (H9/HIV) containing $4 \times 10^{11}$ particles of HIV. Infected cells were divided into five Roller bottles and harvested after 4, 10, 15, 24 and 48 hours. Low molecular weight DNA was prepared using the Hirt fractionation procedure and 30 g of undigested and digested DNA were separated on a 0.8% agarose gel, transferred to nitrocellulose paper and hybridized to a HIV cDNA probe for 24 hours at 37° C. in 1×SSC, 40% formamide and 10% Dextran sulfate. cDNA was synthesized from poly(A) selected RNA prepared from doubly banded HIV virus in the presence of oligo(dT) primers. Filters were washed at 1×SSC at 65° C.

Concentrated virus from the H9/HTLV-III cell line as used to infect fresh uninfected H9 cells at a multiplicity of 50 viral particles per cell and cultures were collected after 4, 10, 15, 24 and 48 hours. Extrachromosomal DNA was extracted according to the procedure of Hirt [Hirt, R., J. Molec. Biol. 26: 365-367 (1967)] and assayed for its content of unintegrated viral DNA using HIV cDNA as a probe. The synthesis of this cDNA was primed with oligo(dT) and reverse-transcribed from poly(A)-containing RNA of virions that had been banded twice on sucrose density gradients [Arya, et al., Science 225: 927-930 (1984)]. Unintegrated linear viral DNA was first detected after 10 h and was also present at the subsequent time points. (FIG. 1 shows a Southern blot of the 15-h sampling.) A band of ~10 kilobases (kb) in the undigested DNA represents the linear form of unintegrated HIV. No closed or nicked circular DNA could be detected at 10, 15 or 24 hours, but both forms were evident in small amounts at 48 hours (data not shown). The viral genome was not cleaved by XbaI, whereas SstI generated three predominant bands of 9, 5.5 and 3.5 kb (FIG. 1). These bands represent the genomes of two forms of HIV, both cut by SstI in or near the long terminal repeat (LTR), and one having an additional SstI site in the middle of its genome. The other enzymes generate a more complex pattern of restriction fragments.

Figure 2:
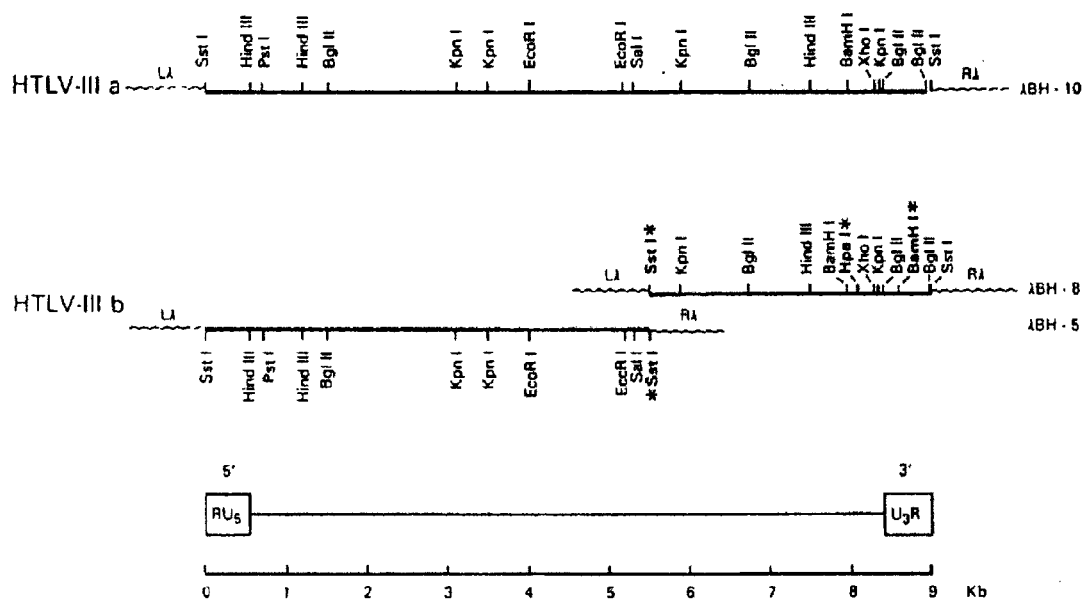
FIG. 2 is a restriction endonuclease map of two closely related HIV variants cloned from unintegrated viral DNA. Three recombinant clones (λBH10, λBH5 and λBH8) were analyzed and their inserts (9 Kb, 5.5 Kb and 3.5 Kb, respectively) were mapped with the indicated enzymes. They represent two variant forms of HIV differing in three enzyme sites which are depicted in bold letters and by an asterisk. As SstI cuts the LTR of the HIV the three clones represent two full-length genomes with one LTR. A schematic map of this viral genome is shown at the bottom of the figure, although the total length of the LTR is approximate.

FIG. 2 shows the restriction map of three clones, designated λBH10, λBH5 and λBH8, which correspond in size to the three SstI fragments shown in FIG. 1. Comparison of these maps suggests that λBH5 plus λBH8 constitute one HIV genome, and BH10 another. The two viral forms differ in 3 of 21 mapped enzymes sites, including the internal SstI site. As expected, the phage inserts of λBH5 and λBH8 hybridize in high-stringency conditions ($T_m$-25° C.) to λBH10 but not to each other, as analyzed by Southern blot hybridization and electron microscopic hetero-duplex analysis (data not shown). To determine the orientation of the three clones, we used as a probe a cDNA clone (C15) containing U3 and R sequences. C15 hybridized strongly to the 0.5 kb BglII fragment of λBH10 and λBH8, orienting this side 3'. Assuming that SstI cuts only once in the vicinity of the HIV LTR, the clones λBH10 and λBH5/λBH8 represent two complete genomic equivalents of the linear unintegrated form of HIV that vary in three restriction enzyme sites.

Methods: Low molecular weight DNA combined from the 15 and 24 hour harvest was fractionated on a 10-40% sucrose gradient. Aliquots of the fractions were electrophoresed on a 0.5% agarose gel, transferred to nitrocellulose paper and hybridized to HIV cDNA under conditions described in FIG. 1. Fractions which contained the unintegrated linear HIV genome shown by hybridization were pooled, the DNA was subsequently digested with SstI and ligated to phosphatase treated SstI arms of λgtWes. λB. After in vitro packaging, recombinant phages were screened for viral sequences with HIV cDNA.

Example 2

Figure 3:
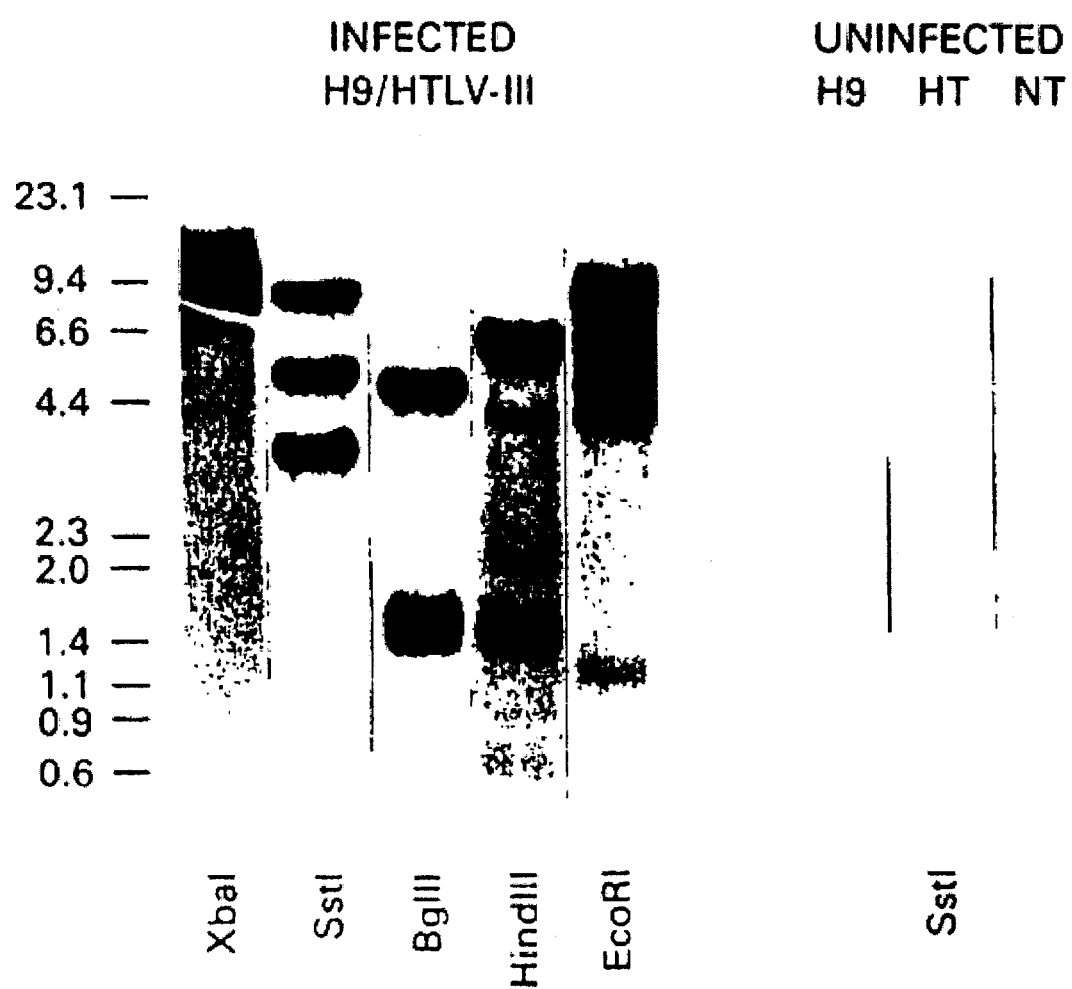
FIG. 3 demonstrates HIV viral sequences in the infected cell line H9/HIV. Both variant forms of HIV were detected as integrated provirus as well as unintegrated viral DNA in the infected cell line. However, no viral sequences were found in uninfected H9 cells, uninfected HT cells nor in normal human thymus (NT).

The presence of two variant forms of HIV in the original cell line was demonstrated by hybridizing the radiolabelled insert of λBH10 to a Southern blot of H9/HIV genomic DNA digested with several restriction enzymes (FIG. 3); both forms were detected using SstI, which generated the expected three bands of 9, 5.5 and 3.5 kb. XbaI, which does not cut the provirus, generated a high-molecular weight smear representing polyclonal integration of the provirus, plus a band of ~10 kb. This 10-kb band was also detected in undigested H9/HIV DNA (not shown), indicating that it represents unintegrated viral DNA. The presence of unintegrated viral DNA also explains the 4- and 4.5-kb EcoRI fragments seen in both the Hirt and total cellular DNA preparations (FIGS. 1, 3). Both BglII and HindIII cut within the LTR and generate the expected internal bands. Several faint bands in addition to the expected internal bands generated by HindIII digestion, represent either defective proviruses or other variant forms of HIV present in low copy number.

Method: 10 μg of high molecular weight DNA were digested with restriction enzymes as indicated and hybridized to nick translated phage insert from BH10 under the same conditions as described in FIG. 1.

For comparison, sub-clones of full length genomes of a prototype HTLV-I, HTLV-Ib, HTLV and GaLV (Seato strain) were digested with the following enzymes, PstI plus SstI (HTLV-I and HTLV-Ib), BamHI plus SmaI (HTLV-II) and Hind III plus SmaI plus XhoI (GaLV). Four replicate filters were prepared and hybridized for 36 hours under low stringency (8×SSC, 20% formamide, 10% Dextran sulfate at 37° C.) to nick translated insert of λBH10. Filters were then washed in 1×SSC at different temperatures, 22° C. (Tm−70° C.) filter 1, 37° C. (Tm−56° C.) filter 2, 50° C. (Tm−42° C.) filter 3 and 65° C. (Tm−28° C.).

Figure 4:
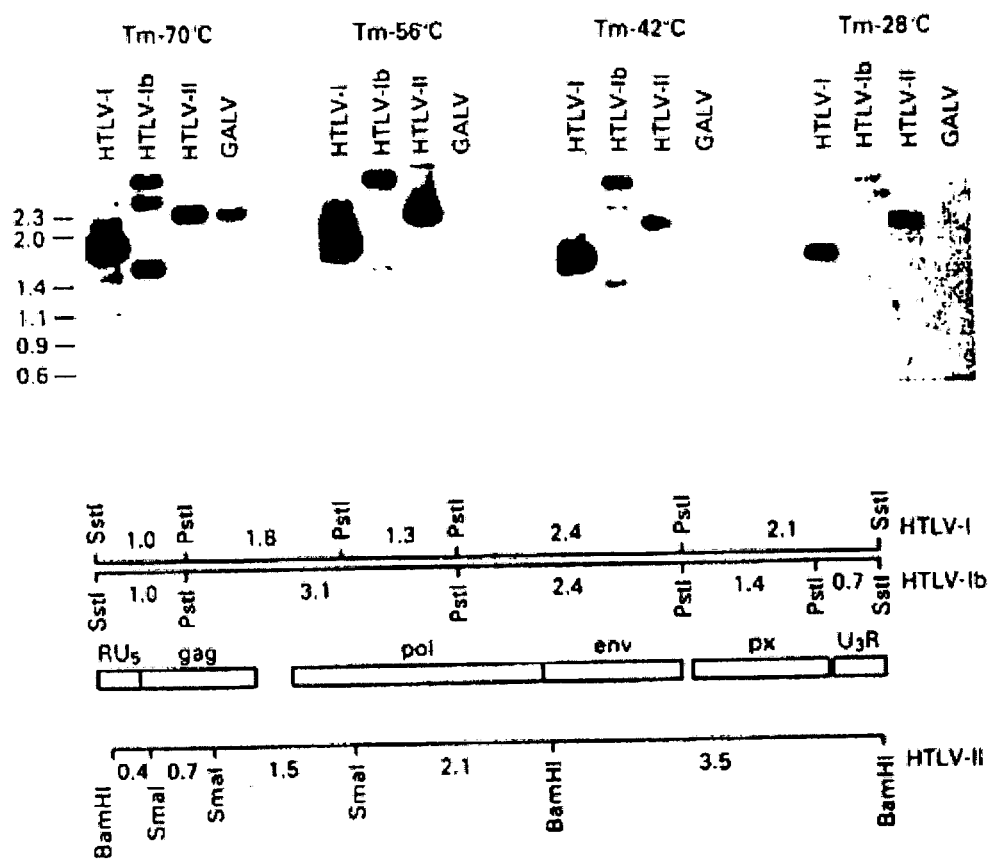
FIG. 4 shows a sequence homology of HIV to related retroviral members of the HTLV family. A schematic restriction map of HTLV-I, HTLV-Ib and HTLV-II is drawn below indicating the length and the location of the generated fragments in respect to the corresponding genomic regions.

FIG. 4 shows a sequence homology between HIV and other related retroviruses. Hybridization of HIV with the related HTLV family could be detected where no hybridization to GaLV was seen.

Preparation of Clones Containing Integrated Proviral DNA

Example 3

The HIV is used to infect H9 cells in accord with the method of Example 1. Preliminary analyses of Southern digests of H9/HIV DNA reveals that the virus is present in this cell line both as unintegrated DNA and as proviral DNA integrated into the cellular genome at multiple different sites. Since the HIV provirus lacks Xba I restriction sites, a genomic library was constructed by using Xba I-digested H9/HIV DNA, and this was screened with an HIV cDNA probe to obtain molecular clones of full-length integrated provirus with flanking cellular sequences. Fourteen such clones were obtained from an enriched library of $10^6$ recombinant phage, and two of these were plaque-purified and characterized. (See FIG. 8.)

Figure 8:
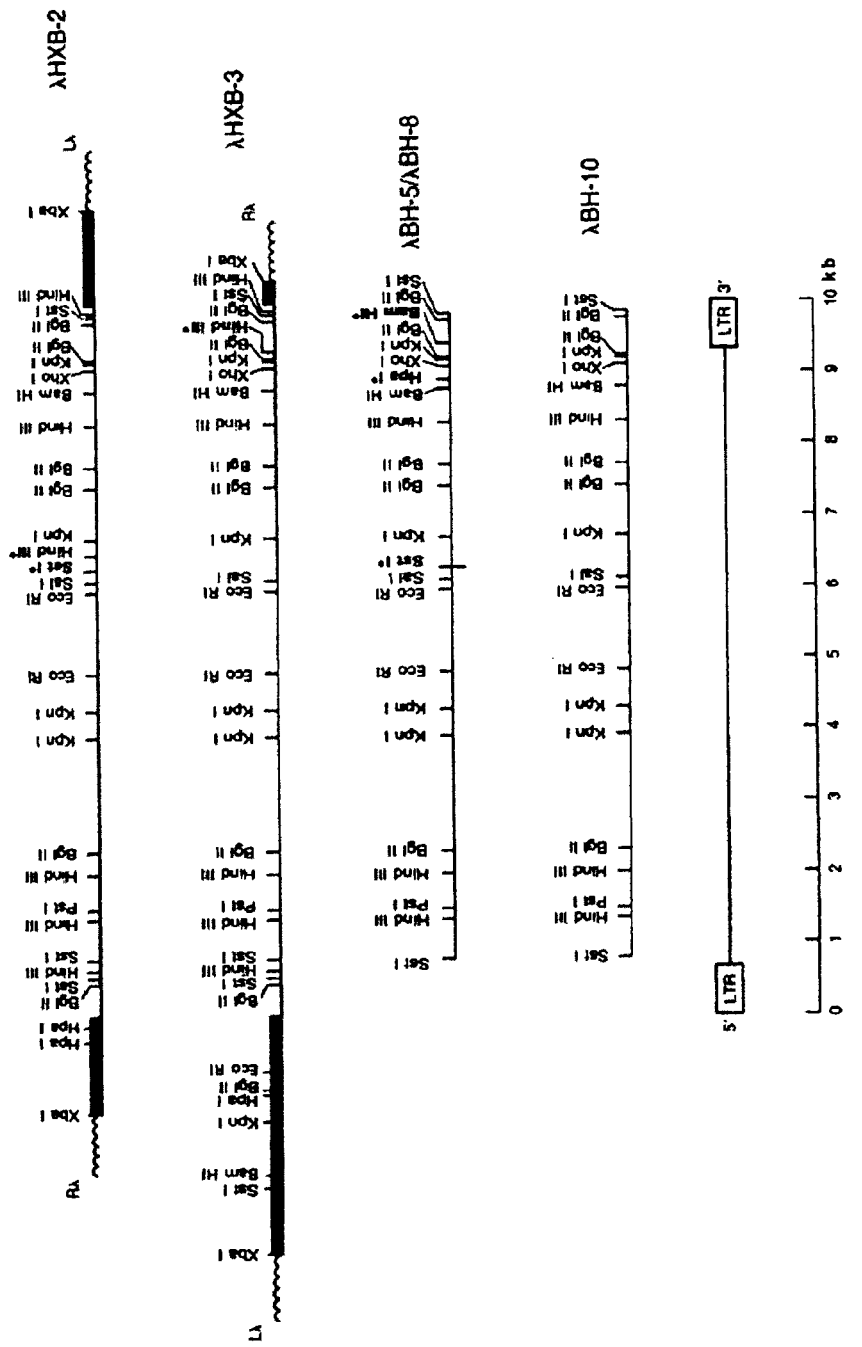
FIG. 8 shows restriction endonuclease maps of four closely related clones of HIV. λHXB-2 and λHXB-3 represent full-length integrated proviral forms of HIV obtained from the λ phage library of H9/HIV DNA (Example 3). These clones contain the complete provirus (thin lines) including two LTR regions plus flanking cellular sequences (heavy lines). The LTR regions are known to contain the three restriction enzyme sites Bgl II, Sst I, and Hind III, as shown, but their overall lengths are estimated. Clones λBH-10 and λBH-5/λBH-8 are shown here for comparison with λHXB-2 and λHXB-3 and with Southern blots of genomic DNA from other HTLV-III containing cells. It should be noted that λBH-5/λBH-8 consists of two separate clones Sst I fragments (λBH-5 and λBH-8) which together constitute one HIV genomic equivalent but which are not necessarily derived from the same viral molecule. Also, because λBH-10 and λBH-5 were cloned with the restriction enzyme Sst I, they lack 5' LTR sequences as shown. Other differences in the restriction maps between these HIV clones are indicated by bold letters and asterisks, with λBH-10 being used as a reference.

To show that the restriction enzyme cleavage sites depicted in FIG. 8 for clones λHXB-2 and λHXB-3 are actually present in the viral DNA of HIV-infected H9 cells, DNA was digested from the H9/HIV cell line with various restriction enzymes and analyzed it by the Southern blot technique. The restriction fragments for Sst I, Eco RI, Hind III, Pst I, Bam H1, and BglII predicted from the restriction maps of λHXB-2 and λHXB-3 (FIG. 8) are shown to be present in the Southern blots of HIV infected cellular DNA.

Example 4

To determine whether the HIV genome contains sequences homologous to normal human DNA, the viral insert of λHXB-2 (5.5 kb and 3.5 kb Sst I-Sst I fragments) was isolated, nick translated, and used to probe HIV-infected and uninfected cellular DNA. Under standard conditions of hybridization [washing conditions: 1×SSC (standard saline citrate), 65° C.; annealing temperature $T_m$−27 C], this probe hybridizes to DNA from H9/HIV cells as well as other HIV-infected cells, but not to DNA from uninfected H9 cells, uninfected HT cells (the parent cell line from which H9 as cloned), or normal human tissues (data not shown). This finding is in agreement with previous results in which the unintegrated (replicative intermediate) form of HIV was used as probe and demonstrates that HIV, like HTLV-1 and HTLV-II, is an exogenous retrovirus lacking nucleic acid sequences derived from human DNA.

Example 5

Figure 9:
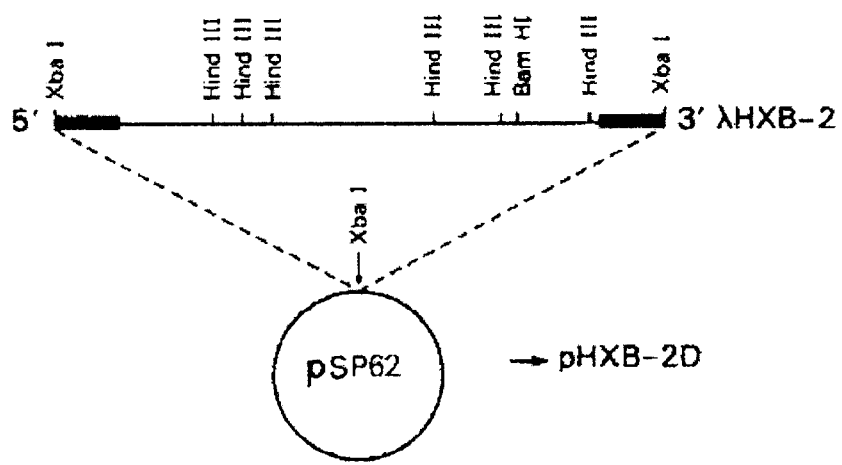
FIG. 9 shows the construction of a plasmid containing sequences of the HIV genome. A 12.7-kb XbaI fragment derived from HXB-2, a molecular clone containing about 10 kb of HIV proviral sequences, was inserted into the XbaI site in the polylinker of plasmid pSP62 to produce the plasmid clone pHXB-2D. This plasmid construct was then transfected into DH-1 bacteria and used in protoplast fusion experiments. The thin horizontal line represents HIV and the solid boxes represent flanking cellular sequences.

A 12.7 kb XbaI fragment derived from λHXB-2 is inserted into the polylinker of plasmid pSP62 to produce plasmid clone pHXB-2D (FIG. 9). The pHXB-2D is transfected into DH-1 bacteria for use in protoplast fusion experiments.

Example 6

Kinetics of cell growth and reverse transcriptase activity in cord blood mononuclear cell cultures following protoplast fusion: Mononuclear cells were prepared from cord blood samples using Ficoll Triosil and cultured for 5 days in media containing PHA. These cells were then fused with bacterial protoplasts carrying the plasmid pHXB-2D, pSV2neo or pCH-1gpt and maintained in culture at a density of $5 \times 10^5$ cells $ml^{-1}$ by addition of RPMI-1640 medium containing 20% fetal calf serum, 10% T-cell growth factor (inter-leukin-2) and antibiotics. Three parallel fusions using cells from different individuals were established for each plasmid. Spent medium removed from two cultures at 5, 11, 14 and 18 days after fusion was concentrated 10-fold and assayed for the presence of reverse transcriptase using standard techniques. The activity detected in each of the culture supernatants is expressed as the amount of $^3$H-labeled deoxyribonucleotide monophosphate ($^3$H-dTMP) incorporated (in pmol per 0.3-ml sample) using $dT_{15} \cdot (rA)_n$ as the template primer.

The growth of all cultures was comparable for the first 14 days after protoplast fusion. By day 18, however, the number of viable cells in cultures transfected with pHXB-2D had fallen dramatically: there was a 10-fold and a 100-fold reduction between days 18 and 21 and 18 and 32, respectively. Cultures transfected with either pSV2neo or pCH-1gpt showed only a 4-5-fold reduction over the same time period. When supernatant from the cultures was assayed for the presence of reverse transcriptase, activity was detected exclusively in cultures transfected with pHXB-2D. These data suggest that replicating virus was present in cultures 11-18 days after fusion with pHXB-2D protoplasts.

Example 7

Expression of the HIV gag-related proteins p15 and p24 by transfected cells was demonstrated using specific monoclonal antibodies. Maximum expression was observed 18 days after transfection, when 4-11% and 5-9% of cells were reactive with antibody to p15 and p24, respectively. Virus particles were detected by electron microscopy in all cultures 14-18 days after transfection with pHXB-2D. The particles contained condensed, truncated cores, which are characteristic of HIV particles.

Example 8

In time-course experiments, DNA isolated from a single culture 6, 11, 14, 18 and 31 days after transfection with pHXB-2D, was digested with BamHI and analyzed for HIV sequences. Six days after transfection, an 8.6-kb DNA fragment was detected as a faint band; 18 days after transfection it was possible to detect a 1.5-kb DNA fragment in addition to the 8.6-kb fragment. The total amount of unintegrated virus in the cultures appeared to increase, as suggested by the increase in intensity of these bands with time; this is evidence that cells originally transfected with pHXB-2D are able to produce fully infectious virus which is then transmitted within the culture.

No HIV viral sequences were detected 31 days after transfection; at this point the culture may have contained only cells which failed to be infected by HIV. This result is again consistent with the transfected DNA exerting a cytopathic effect on T cells. The finding that, at any stage, only a minor population of the transfected cells are apparently infected by the virus (<15% express viral proteins) suggests that the cytopathic effects may not result solely from direct viral infection and that secreted factors and/or other cell-to-cell interactions may play a part in the cytopathic phenomenon.

The biological materials relating to the invention have been deposited at the American Type Culture Collection, Rockville, Md., under the following accession numbers:

| | |
|---|---|
| λBH-10 | 40125 (FIG. 7) |
| λBH-5 | 40126 (FIG. 5) |
| λBH-8 | 40127 (FIG. 6) |
| λ-HXB$_2$ | 40231 |
| λ-HXB$_3$ | 40232 |
| pHXB3 | 67081 |
| pHXB-2D | 67082 |
| X10-1 (*E coli* DH-1) | 67083 |

Upon issuance of a patent on the present invention, this deposit will continue to be viably maintained for 30 years and made available to the public without restriction, of course, consistent with the provisions of the law.

Examples of useful products are now described:
1. Viral particles and proteins may be extracted from both supernatants and whole cells.
2. Supernatant material may be purified for use in test kits for immunoblotting and immunoadsorbent tests.
3. Monoclonal antibodies may be produced which react against HIV antigens.
4. The antigens may be used as immunogens in vaccine development.

Both antibodies and antigens can be used in diagnostic kits. Both antibodies and antigens can be provided as compositions. Particularly preferred compositions of matter are solid supports having antigens of the invention adhering thereto for use in identifying antibodies to HIV proteins for use in Enzyme-linked-immunoabsorbent (ELISA) assays.

It is understood that the examples and embodiments described herein are for illustration purposes. Examples are not intended to be viewed as limitations since many obvious modifications are within the scope of one skilled in the art.

TABLE I

CLAIMS SUPPORT CHART

| Claim | Support in U.S. patent application 06/643,306 filed on Aug. 22, 1984 |
|---|---|
| 61. (new) A method for detecting the presence of a polynucleotide comprising a human immunodeficiency virus (HIV) nucleotide sequence in a nucleic acid sample obtained from a physiological sample, which method comprises the steps of:<br>(a) combining said nucleic acid sample with a single-stranded nucleic acid probe comprising a sequence of at least about 18 contiguous bases selected from one of the nucleotide sequences shown in FIGS. 5, 6 or 7 and complementary to said HIV genomic sequence comprised in said polynucleotide, said probe not forming a duplex with HTLV-I and -II nucleic acid sequences under conditions of stringency for hybridization under which said probe forms a duplex with said polynucleotide; and<br>(b) determining duplex formation between said probe and nucleic acid present in said sample. | page 1, lines 28-34. discusses the use of cDNA clones of the invention to distinguish HTLV III from HTLV I and II.<br>p. 3 line 25 to p. 4 line 8 discuss regions of homology and regions of variability between HTLV III, and HTLV I and II, that can be exploited in distinguishing between the different viruses.<br>p. 5, lines 12-14 discusses production of a cDNA library for use in analyzing the HIV genome.<br>p. 5 line 29 - p. 6 line 10 provides support for making probes from HIV mRNA.<br>p. 6, lines 23-26 discusses using probes to assay viral DNA<br>p. 7, lines 18-30 discuss using an λ phage clone in Southern analysis of restriction fragments from HIV DNA.<br>Statement of Deposit, p. 6.<br>p. 1 discussion relating to detection of HIV in human sera.<br>BH10 contains an 18 base BglII-SstI restriction fragment.<br>FIG. 4 shows that only a fraction of the HTLV-I and -II genomes hybridize to HTLV-III.<br>Example 2, p. 8 discusses the use of stringency washes to distinguish homology between HIV, HTLV I and HTLV II. |
| 62. (new) The method of claim 61 wherein the probe sequence is complementary to a sequence which is part of the gag, pol or env open reading frame. | p. 3 contains a discussion relating to the presence of gag, pol and env in HTLV-III. |
| 63. (new) The method of claim 62 wherein the probe sequence is complementary to a sequence which is part of the gag open reading frame. | |
| 64. (new) The method of claim 62 wherein the probe is complementary to a sequence which is part of the pol open reading frame. | |
| 65. (new) The method of claim 61 wherein the probe comprises RNA. | p. 5 discussion of the use of RNA as probe/probe template. |
| 67. (new) The method of claim 62 wherein the probe comprises RNA. | |
| 66. (new) The method of claim 61 wherein the probe comprises DNA. | Support noted for claim 1 refers to DNA probes |
| 68. (new) The method of claim 62 wherein the probe comprises DNA. | |

TABLE I-continued

CLAIMS SUPPORT CHART

| Claim | Support in U.S. patent application 06/643,306 filed on Aug. 22, 1984 |
|---|---|
| 69. (new) A method comprising the steps of:<br>(a) providing a sample suspected of containing a polynucleotide;<br>(b) providing a single-stranded nucleic acid of 18-103 bases comprising a sequence of bases of at least 18 contiguous bases selected from the gag, env, or pol open reading frames of FIG. 5, 6 or 7 or the complement thereof; and<br>(c) combining said sample and said single-stranded nucleic acid under hybridization conditions that (i) permit duplex formation between said single-stranded nucleic acid and either strand of viral DNA from a lambda bacteriophage selected from the group consisting of ATCC Accession no. 40143 and 40144, but (ii) do not permit duplex formation with either HTLV-I or HTLV-II genomic sequences. | Support noted for claim 61 also applies here.<br>clone BH5 contains a HindIII-XbaI fragment that is 103 bases in length.<br>p. 3 contains a discussion relating to the presence of gag, pol and env in HTLV-III. |
| 70. (new) A method comprising the steps of:<br>(a) providing a sample suspected of containing a polynucleotide;<br>(b) providing a single-stranded nucleic acid of 32-103 bases comprising a sequence of bases of at least 32 contiguous bases selected from the gag, env, or pol open reading frames of FIG. 5, 6 or 7 or the complement thereof; and<br>(c) combining said sample and said single-stranded nucleic acid under hybridization conditions that (i) permit duplex formation between said single-stranded nucleic acid and either strand of viral DNA from a lambda bacteriophage selected from the group consisting of ATCC Accession no. 40143 and 40144, but (ii) do not permit duplex formation with either HTLV-I or HTLV-II genomic sequences. | |
| 71. (new) The method of claim 69 or 70 wherein contiguous bases are from the gag open reading frame or the complement thereof. | p. 3 contains a discussion relating to the presence of gag, pol and env in HTLV-III. |
| 72. (new) The method of claim 69 or 70 wherein said contiguous bases are from the env open reading frame or the complement thereof. | |
| 73. (new) The method of claim 69 or 70 wherein said contiguous bases are from the pol open reading frame or the complement thereof. | |
| 74. (new) The method of claim 61, 69 or 70 wherein said single-stranded nucleic acid comprises DNA and wherein said contiguous bases are within a restriction fragment produced by cleavage of the nucleic acid presented in FIG. 5, 6 or 7 using one or more restriction enzymes selected from the group consisting of SstI, HindIII, PstI, Bgl II, Kpn I, EcoRI, BamHI, HpaI, XhoI, XbaI and SmaI. | SstI pg. 2 and FIG. 2;<br>HindIII pg. 4, and FIG. 2;<br>PstI pg. 2 and FIG. 2<br>Bgl II pg. 7 and FIG. 2;<br>Kpn I FIG. 2;<br>EcoRI Page 7 and FIG. 2;<br>BamHI Page 2 and FIG. 2;<br>HpaI Page 2 and FIG. 2;<br>XhoI Page 2 and FIG. 2;<br>XbaI Page 7 and FIG. 3; and<br>SmaI FIG. 2. |
| 75. (new) The method of claim 74 wherein the single-stranded nucleic acid probe comprises one of the nucleotide sequences selected from the group consisting of: [Restriction Fragments supported in Wong-Staal specification.] | p. 9, lines 28-32 discusses the use of λBH10 and restriction fragments to analyze the HIV genome.<br>p. 6, lines 23-26 discusses using cDNA to detect viral DNA |
| 76. (new) The method of claim 75, wherein the single-stranded nucleic acid is 5'-CTTTAAGACCAATGACTTACAAGGCAGCTGTA -3'. | p. 7, lines 18-30 and p. 9 lines 15-26 discuss using an λ phage clone in Southern analysis of restriction fragments from HIV DNA.<br>32 nucleotide restriction fragment present in BH8.<br>Nucleotide sequence of claim 76 nucleic acid is a 32 nucleotide KpnI-BglII restriction fragment from clone BH8 |
| 77. (new) A method for detecting the presence of a polynucleotide comprising a human immunodeficiency virus (HIV) nucleotide sequence in a nucleic acid sample obtained from a physiological sample, which method comprises the steps of:<br>(a) combining said nucleic acid sample with a single-stranded nucleic acid probe comprising a sequence of at least about 32 contiguous bases selected from one of the nucleotide sequences shown in FIGS. 5, 6 or 7 and complementary to said HIV genomic sequence comprised in said polynucleotide, said probe not forming a duplex with HTLV-I and -II nucleic acid sequences under conditions of stringency for hybridization under which said probe forms a duplex with said polynucleotide; and<br>(b) determining duplex formation between said probe and nucleic acid present in said sample. | Support cited for claim 1 is applicable here.<br>See also support for claim 76. |
| 78. (new) The method of claim 61, wherein the single-stranded nucleic acid probe is 5'- GATCTGAGCCTGGGAGCT-3'. | 18 base BglII-SstI restriction fragment of BH10. |
| 79. (new) The method of any of claims 69-73 wherein said single-stranded nucleic acid comprises RNA. | Discussion on p. 5 relating to the use of RNA as probe/probe template. |
| 80. (new) The method of any of claims 69-73 wherein said single-stranded nucleic acid comprises DNA. | p. 1, lines 28-34. discusses the use of cDNA clones of the invention to distinguish HTLV III from HTLV I and II. |
| 81. (new) The method of claim 79 wherein said single-stranded nucleic acid further comprises a label. | Original claim 5 discusses radiolabels.<br>FIGS. 1, 3 and 4 show assays using labeled DNA. |
| 82. (new) The method of claim 80 wherein said single-stranded nucleic acid further comprises a label. | p5, lines 24-26 discuss labeled probes, and p. 7 lines 18-22 discuss nick translation. |
| 83. (new) The method of claims 69-73, wherein said sample is a human sample. | p. 1 contains a discussion of the use of probes to detect HTLV-III in human sera. |

TABLE I-continued

CLAIMS SUPPORT CHART

| Claim | Support in U.S. patent application 06/643,306 filed on Aug. 22, 1984 |
|---|---|
| 84. (new) The method of claim 83, wherein said human sample is blood, lymph or saliva. | |
| 85. (new) The method of claims 84, wherein said sample is blood. | |
| 86. (new) A method for detecting the presence of a polynucleotide comprising a human immunodeficiency virus (HIV) nucleotide sequence in a nucleic acid sample, the method comprising the steps of: (a) combining said nucleic acid sample with a single-stranded nucleic acid probe hybridizing under stringent conditions to an HIV nucleotide sequence present in a nucleic acid deposit selected from the group consisting of H9/HTLV-III cell line, CRL 8543; BH10, ATCC #40125; BH8, ATCC #40127; and BH5, ATCC #40126, said probe not forming a duplex with HTLV-I and -II nucleic acid sequences under conditions of stringency for hybridization that allow said probe to form a duplex with said polynucleotide; and (b) determining duplex formation between said probe and said nucleic acid present in said sample. | page 1, lines 28-34. discusses the use of cDNA clones of the invention to distinguish HTLV III from HTLV I and II. p. 3 line 25 to p. 4 line 8 discuss regions of homology and regions of variability between HTLV III, and HTLV I and II, that can be exploited in distinguishing between the different viruses. p. 5, lines 12-14 discusses production of a cDNA library for hybridization analysis of the HIV genome. p. 5 line 29 - p. 6 line 10 provides support for making cDNA probes from HIV mRNA. p. 6, lines 23-26 discusses using cDNA probes to assay viral DNA p. 7, lines 18-30 discuss using an λ phage clone in southern analysis of restriction fragments from HIV DNA by Southern blot. Statement of Deposit, p. 6. Example 2, p. 8 discusses the use of stringency washes to distinguish homology between HIV, HTLV I and HTLV II. |
| 87. (new) The method of claim 86, wherein the nucleic acid probe is a restriction fragment. | p. 5 lines 23-28 discuss hybridizing cDNA sequences to genomic restriction fragments of HIV. |
| 88. (new) The method of claim 86, wherein the probe sequence is complementary to a sequence that is part of the gag, pol or env coding regions. | p. 5, lines 12-14 discusses production of a cDNA library for hybridization analysis of the HIV genome. p. 5 lines 23-28 discuss hybridizing cDNA sequences to genomic restriction fragments of HIV. See also, FIG. 4 (restriction map) and p. 3, line 30 to p. 4 line 3. |
| 89. (new) The method of claim 86, wherein the probe comprises DNA. | Support noted for claim 1 refers to DNA probes |
| 90. (new) The method of claim 87, wherein the probe comprises DNA. | |
| 91. (new) A method comprising the steps of: (a) providing a sample suspected of containing a polynucleotide; (b) providing a single-stranded HIV cDNA; and, (c) combining said sample and said single-stranded HIV cDNA under hybridization conditions that (i) permit duplex formation between said HIV cDNA and either nucleotide strand from a lambda bacteriophage selected from the group consisting of λBH10, λBH5 and λBH8, but (ii) do not permit duplex formation with either HTLV-I or HTLV-II genomic sequences. | p. 1, lines 28-34. discusses the use of cDNA clones of the invention to distinguish HTLV III from HTLV I and II. p. 3 line 25 to p. 4 line 8 discuss regions of homology and regions of variability between HTLV III, and HTLV I and II, that can be exploited in distinguishing between the different viruses. p. 5, lines 12-14 discusses production of a cDNA library for hybridization analysis of the HIV genome. p. 5 line 29 - p. 6 line 10 provides support for making cDNA probes from HIV mRNA. p. 9, lines 28-32 discusses the use of the λBH10 clone and HIV genomic restriction fragments in hybridization studies. p. 6, lines 23-26 discusses using cDNA probes to assay viral DNA p. 7, lines 18-30 and p. 9 lines 15-26 discuss using an λ phage clone in Southern analysis of restriction fragments from HIV DNA. Statement of Deposit, p. 6. Example 2, p. 8 discusses the use of stringency washes to distinguish homology between HIV, HTLV I and HTLV II. |
| 92. (new) The method of claim 91, wherein said single-stranded nucleic acid is an SstI fragment or complement thereof. | FIGS. 2 and 3 provide restriction maps that would allow one of skill to identify probes to particular genomic regions. p. 9, lines 28-32 specifically discusses use probes to analyze restriction fragments. Also note discussion from p. 5, line 29 to p. 6, line 26 regarding the use of cDNA probes See also, FIG. 4 and p. 3, line 30 to p. 4 line 3. |
| 93. (new) The method of claim 91 wherein said single-stranded nucleic acid is a HindIII fragment or complement thereof. | FIGS. 2 and 3 provide restriction maps that would allow one of skill to identify probes to particular genomic regions. p. 9, lines 28-32 specifically discusses hybridization analysis using restriction fragments. Also note discussion from p. 5, line 29 to p. 6, line 26 regarding the use of cDNA sequences as probes. See also, FIG. 4 and p. 3, line 30 to p. 4 line 3. |
| 94. (new) The method of claim 91 wherein said single-stranded nucleic acid comprises DNA and hybridizes to a restriction fragment generated by treating an HIV genomic nucleic acid with HindIII and BamHI. | FIGS. 2 and 3 provide restriction maps that would allow one of skill to identify probes to particular genomic regions. p. 9, lines 28-32 specifically discusses use probes to analyze restriction fragments. Also note discussion from p. 5, line 29 to p. 6, line 26 regarding the use of cDNA probes See also, FIG. 4 and p. 3, line 30 to p. 4 line 3. |
| 95. (new) The method of any of claims 91-94 wherein said single-stranded nucleic acid comprises DNA. | p. 1, lines 28-34. discusses the use of cDNA clones of the invention to distinguish HTLV III from HTLV I and II. |
| 96. (new) The method of claim 95 wherein said single-stranded nucleic acid further comprises a label. | Original claim 5 discusses radiolabels. FIGS. 1, 3 and 4 show assays using labeled DNA. p5, lines 24-26 discuss labeled probes, and p. 7 lines 18-22 discuss nick translation. |
| 97. (new) The method of claim 92 wherein said single-stranded nucleic acid comprises DNA and wherein said contiguous bases are within the gag open reading frame. | FIGS. 2 and 3 provide restriction maps that would allow one of skill to identify probes to particular genomic regions. p. 9, lines 28-32 specifically discusses hybridization analysis using restriction fragments. Also note discussion from p. 5, line 29 to p. 6, line 26 regarding the use of cDNA sequences as probes. See also, FIG. 4 and p. 3, line 30 to p. 4 line 3. |

TABLE I-continued

CLAIMS SUPPORT CHART

| Claim | Support in U.S. patent application 06/643,306 filed on Aug. 22, 1984 |
|---|---|
| 98. (new) The method of claim 97 wherein said single-stranded nucleic acid further comprises a label. | Original claim 5 discusses radiolabels.<br>FIGS. 1, 3 and 4 show assays using labeled DNA.<br>p5, lines 24-26 discuss labeled probes, and p. 7 lines 18-22 discuss nick translation. |
| 99. (new) A method for detecting the presence of a polynucleotide comprising a human immunodeficiency virus (HIV) genomic sequence in a nucleic acid sample obtained from a physiological sample, which method comprises the steps of:<br>(a) combining said nucleic acid sample with a single-stranded nucleic acid probe comprising a sequence of at least about 20 contiguous bases selected from the nucleotide sequences shown in FIGS. 5-7 and complementary to said HIV genomic sequence comprised in said polynucleotide, said probe not forming a duplex with HTLV-I and -II nucleic acid sequences under conditions of stringency for hybridization under which said probe forms a duplex with said polynucleotide; and<br>(b) determining duplex formation between said probe and nucleic acid present in said sample. | page 1, lines 28-34. discusses the use of cDNA clones of the invention to distinguish HTLV III from HTLV I and II.<br>p. 3 line 25 to p. 4 line 8 discuss regions of homology and regions of variability between HTLV III, and HTLV I and II, that can be exploited in distinguishing between the different viruses.<br>p. 5, lines 12-14 discusses production of a cDNA library for use in hybridization studies of the HIV genome.<br>p. 5 line 29 - p. 6 line 10 provides support for making cDNA probes from HIV mRNA.<br>p. 6, lines 23-26 discusses using cDNA sequences for use in hybridization studies of the HIV genome.<br>p. 7, lines 18-30 discuss using an λ phage clone in Southern analysis of restriction fragments from HIV DNA.<br>Statement of Deposit, p. 6.<br>p. 1 discussion relating to detection of HIV in human sera.<br>BH10 contains an 18 base BglII-SstI restriction fragment. |
| 100. (new) The method of claim 99 wherein the probe sequence is complementary to a sequence which is part of the gag, pol or env open reading frame. | p. 3 contains a discussion relating to the presence of gag, pol and env in HTLV-III. |
| 101. (new) The method of claim 100 wherein the probe sequence is complementary to a sequence which is part of the gag open reading frame. | |
| 102. (new) The method of claim 100 wherein the probe is complementary to a sequence which is part of the pol open reading frame. | |
| 103. (new) The method of claim 99 wherein the probe comprises RNA. | p. 5 discussion of the use of RNA as probe/probe template. |
| 105. (new) The method of claim 100 wherein the probe comprises RNA. | |
| 104. (new) The method of claim 99 wherein the probe comprises DNA. | Support noted for claim 1 refers to DNA probes |
| 106. (new) The method of claim 100 wherein the probe comprises DNA. | |
| 107. (new) A method comprising the steps of:<br>(a) providing a sample suspected of containing a polynucleotide;<br>(b) providing a single-stranded nucleic acid of 20-100 bases comprising a sequence of bases of at least 20 contiguous bases selected from the gag, env, or pol open reading frames; and<br>(c) combining said sample and said single-stranded nucleic acid under hybridization conditions that (i) permit duplex formation between said single-stranded nucleic acid and either strand of viral DNA from a lambda bacteriophage selected from the group consisting of ATCC Accession no. 40143 and 40144, but (ii) do not permit duplex formation with either HTLV-I or HTLV-II genomic sequences. | Support noted for claim 61 also applies here.<br>p. 3 contains a discussion relating to the presence of gag, pol and env in HTLV-III. |
| 108. (new) The method of any of claims 107 wherein said single-stranded nucleic acid comprises RNA. | p. 5 discussion of the use of RNA as probe/probe template. |
| 109. (new) The method of any of claims 107 wherein said single-stranded nucleic acid comprises DNA. | Support noted for claim 1 refers to DNA probes |
| 110. (new) The method of claim 108 wherein said single-stranded nucleic acid further comprises a label. | Original claim 5 discusses radiolabels.<br>FIGS. 1, 3 and 4 show assays using labeled DNA.<br>p5, lines 24-26 discuss labeled probes, and p. 7 lines 18-22 discuss nick translation. |
| 111. (new) The method of claim 109 wherein said single-stranded nucleic acid further comprises a label. | |
| 112. (new) The method of claim 108 wherein said single-stranded nucleic acid is chemically synthesized at least in part. | The paragraph spanning pages 5 and 6 discusses chemically synthesizing DNA using NaOH, an RNA template, and restriction enzymes. |
| 113. (new) The method of claim 109 wherein said single-stranded nucleic acid is chemically synthesized at least in part. | |
| 114. (new) The method of claim 110 wherein said single-stranded nucleic acid is chemically synthesized at least in part. | |
| 115. (new) The method of claim 111 wherein said single-stranded nucleic acid is chemically synthesized at least in part. | |
| 116. (new) The method of claims 99 or 101 wherein said sample is a human sample. | p. 1 contains a discussion of the use of probes to detect HTLV-III in human sera. |
| 117. (new) The method of claim 116 wherein said human sample is blood, lymph or saliva. | |
| 118. (new) The method of claims 99 or 101 wherein said sample is blood, lymph or saliva. | |

TABLE II (BH 5 and 8 v. LUCIW)
89.8% identity

```
            10        20        30        40        50
BH 8   -TGGAAGGGCTAATTCACTCCCAACGAAGACAAGATATCCTTGATCTGTGGATCCACCAC
        :::::::::::::      ::::::  ::::::::::  :::::::::::::::::::  :::::
Licuw, CTGGAAGGGCTAATTTGGTCCCAAAGAAGACAAGAGATCCTTGATCTGTGGATCTACCAC
            10        20        30        40        50        60

60        70        80        90       100       110
BH 8   ACACAAGGCTACTTCCCTGATTGGCAGAACTACACACCAGGGCCAGGAGTCAGATATCCA
       :::::::::::::::::::::::::::::::::::  ::::::::::::::  :::::::::::
Licuw, ACACAAGGCTACTTCCCTGATTGGCAGAATTACACACCAGGGCCAGGGATCAGATATCCA
           70        80        90       100       110       120

120       130       140       150       160       170
BH 8   CTGACCTTTGGATGGTGCTACAAGCTAGTACCAGTTGAGCCAGAGAAGTAAGAAGAAGCC
       ::::::::::::::::::::  :::::::::::::::::::::::::::::      :::::  :::
Licuw, CTGACCTTTGGATGGTGCTTCAAGCTAGTACCAGTTGAGCCAGAGAAGGTAGAAGAGGCC
          130       140       150       160       170       180

180       190       200       210       220       230
BH 8   AATAAAGGAGAGAACACCAGCTTGTTACACCCTGTGAGCCTGCATGGAATTGATGACCCG
       :::  :::::::::::::::: ::::::::::::::: :::::::::::::::::  ::  :::  ::
Licuw, AATGAAGGAGAGAACAACAGCTTGTTACACCCTATGAGCCTGCATGGGATGGAGGACGCG
          190       200       210       220       230       240

240       250       260       270       280       290
BH 8   GAGAGAGAAGTGTTAGAGTGGAGGTTTGACAGCCGCCTAGCATTTCATCACATGGCCCGA
       ::::  :::::::::::::  ::::::::::::::::::  :::::::::::::::::::::::::
Licuw, GAGAAAGAAGTGTTAGTGTGGAGGTTTGACAGCAAACTAGCATTTCATCACATGGCCCGA
          250       260       270       280       290       300

300       310       320       330       340       350
BH 8   GAGCTGCATCCGGAGTACTTCAAGAACTGCTGACATCGAGCTTGCTACAAGGGACTTTCC
       ::::::::::::::::::::  :::   ::::::::::::::::::::::  :::::::::::::::
Licuw, GAGCTGCATCCGGAGTACTACAAAGACTGCTGACATCGAGCTTTCTACAAGGGACTTTCC
          310       320       330       340       350       360

360       370       380       390       400       410
BH 8   GCTGGGGACTTTCCAGGGAGGCGTGGCCTGGGCGGGACTGGGGAGTGGCGAGCCCTCAGA
       ::::::::::::::::::::::::::::::::::::::::::::::::::::::  ::::::::
Licuw, GCTGGGGACTTTCCAGGGAGGCGTGGCCTGGGCGGGACTGGGGAGTGGCGT-CCCTCAGA
          370       380       390       400       410

420       430       440       450       460       470
BH 8   TCCTGCATATAAGCAG-CTGCTTTTTGCCTGTACTGGGTCTCTCTGGTTAGACCAGATCT
       :  :::::::::::::::  :::::::::::::::::::::::::::::::::::::::::::
Licuw, TGCTGCATATAAGCAGACTGCTTTTTGCCTGTACTGGGTCTCTCTGGTTAGACCAGATCT
          420       430       440       450       460       470

480       490
BH 8   GAGCCTGGGAGCTC---------------------------------------------
       :::::::::::::::
Licuw, GAGCCTGGGAGCTCTCTGGCTAACTAGGGAACCCACTGCTTAAGCCTCAATAAAGCTTGC
          480       490       500       510       520       530

------------------------------------------------------------

Licuw, CTTGAGTGCTTCAAGTAGTGTGTGCCCGTCTGTTGTGTGACTCTGGTAACTAGAGATCCC
          540       550       560       570       580       590

------------------------------------------------------------

Licuw, TCAGACCCTTTTAGTCAGTGTGGAAAAATCTCTAGCAGTGGCGCCCGAACAGGGACGCGA
          600       610       620       630       640       650

500       510       520       530
BH 5   -------------------GAGCTCTCTCGACGCAGGACTCGGCTTGCTGAAGCGCGCA
                           ::::::::::::::::::::::::::::::::::::::::::
Licuw, AAGCGAAAGTAGAACCAGAGGAGCTCTCTCGACGCAGGACTCGGCTTGCTGAAGCGCGCA
          660       670       680       690       700       710

540       550       560       570       580       590
BH 5   CGGCAAGAGGCGAGGGGCGGCGACTGGTGAGTACGCCAAAAATTTTGACTAGCGGAGGCT
       : ::::::::::::::::::::::::::::::::::::::::  ::::::::::::::::::
Licuw, CAGCAAGAGGCGAGGGGCGGCGACTGGTGAGTACGCCAAT--TTTTGACTAGCGGAGGCT
          720       730       740       750       760       770

600       610       620       630       640       650
```

TABLE II-continued (BH 5 and 8 v. LUCIW)
89.8% identity

```
BH 5    AGAAGGAGAGAGA--TGGGTGCGAGAGCGTCAGTATTAAGCGGGGGAGAATTAGATCGAT
        ::::::::::::: :::::::::::::::::: ::::::::::::::::::::::: ::
Licuw,  AGAAGGAGAGAGAGATGGGTGCGAGAGCGTCGGTATTAAGCGGGGGAGAATTAGATAAAT
        780       790       800       810       820       830

660       670       680       690       700       710
BH 5    GGGAAAAAATTCGGTTAAGGCCAGGGGGAAAGAAAAAATATAAATTAAAACATATAGTAT
        :::::::::::::::::::::::::::::::::::::::::: :::::::::::::::::
Licuw,  GGGAAAAAATTCGGTTAAGGCCAGGGGGAAAGAAAAAATATAAGTTAAAACATATAGTAT
        840       850       860       870       880       890

720       730       740       750       760       770
BH 5    GGGCAAGCAGGGAGCTAGAACGATTCGCAGTTAATCCTGGCCTGTTAGAAACATCAGAAG
        :::::::::::::::::::::::::::::::: :::::::::::::::::::::::::::
Licuw,  GGGCAAGCAGGGAGCTAGAACGATTCGCAGTCAATCCTGGCCTGTTAGAAACATCAGAAG
        900       910       920       930       940       950

780       790       800       810       820       830
BH 5    GCTGTAGACAAATACTGGGACAGCTACAACCATCCCTTCAGACAGGATCAGAAGAACTTA
        :::: :::::::::: ::::::::::::: ::::::::::::::::::::::::::::::
Licuw,  GCTGCAGACAAATATTGGGACAGCTACAGCCATCCCTTCAGACAGGATCAGAAGAACTTA
        960       970       980       990      1000      1010

840       850       860       870       880       890
BH 5    GATCATTATATAATACAGTAGCAACCCTCTATTGTGTGCATCAAAGGATAGAGATAAAAG
        :::::::::::::::::::::::::::::::::::::::: :::::::::::: :::::
Licuw,  GATCATTATATAATACAGTAGCAACCCTCTATTGTGTACATCAAAGGATAGATGTAAAAG
        1020      1030      1040      1050      1060      1070

900       910       920       930       940       950
BH 5    ACACCAAGGAAGCTTTAGACAAGATAGAGGAAGAGCAAAACAAAAGTAAGAAAAAAGCAC
        :::::::::::::::::::: :::::::::::::::::::::::::::::::::: ::::
Licuw,  ACACCAAGGAAGCTTTAGAGAAGATAGAGGAAGAGCAAAACAAAAGTAAGAAAAAGGCAC
        1080      1090      1100      1110      1120      1130

960       970       980       990      1000
BH 5    AGCAAGCAGCAGCTGA------CACAGGACACAGCAGTCAGGTCAGCCAAAATTACCCTA
        :::::::::::::::::      :::::::::::::: :::::::::::::::::::::
Licuw,  AGCAAGCAGCAGCTGCAGCTGGCACAGGAAACAGCAGCCAGGTCAGCCAAAATTACCCTA
        1140      1150      1160      1170      1180      1190

1010      1020      1030      1040      1050      1060
BH 5    TAGTGCAGAACATCCAGGGGCAAATGGTACATCAGGCCATATCACCTAGAACTTTAAATG
        ::::::::::::: :::::::::::::::::::::::::::::::::::::::::::::
Licuw,  TAGTGCAGAACCTACAGGGGCAAATGGTACATCAGGCCATATCACCTAGAACTTTAAATG
        1200      1210      1220      1230      1240      1250

1070      1080      1090      1100      1110      1120
BH 5    CATGGGTAAAAGTAGTAGAAGAGAAGGCTTTCAGCCCAGAAGTAATACCCATGTTTTCAG
        :::::::::::::::::::::::: ::::::::::::::::::::::::::::::::::
Licuw,  CATGGGTAAAAGTAGTAGAAGAAAAGGCTTTCAGCCCAGAAGTAATACCCATGTTTTCAG
        1260      1270      1280      1290      1300      1310

1130      1140      1150      1160      1170      1180
BH 5    CATTATCAGAAGGAGCCACCCCACAAGATTTAAACACCATGCTAAACACAGTGGGGGAC
        ::::::::::::::::::::::::::::::::::::::::::::::::::::::::::::
Licuw,  CATTATCAGAAGGAGCCACCCCACAAGATTTAAACACCATGCTAAACACAGTGGGGGAC
        1320      1330      1340      1350      1360      1370

1190      1200      1210      1220      1230      1240
BH 5    ATCAAGCAGCCATGCAAATGTTAAAAGAGACCATCAATGAGGAAGCTGCAGAATGGGATA
        :::::::::::::::::::::::::::::::: :::::::::::::::::::::::::::
Licuw,  ATCAAGCAGCCATGCAAATGTTAAAAGAGACTATCAATGAGGAAGCTGCAGAATGGGATA
        1380      1390      1400      1410      1420      1430

1250      1260      1270      1280      1290      1300
BH 5    GAGTGCATCCAGTGCATGCAGGGCCTATCGCACCAGGCCAGATGAGAGAACCAAGGGGAA
        :::::::::::::::::::::::::::: ::::::::::::: :::::::::::::::::
Licuw,  GAGTGCATCCAGTGCATGCAGGGCCTATTGCACCAGGCCAAATGAGAGAACCAAGGGGAA
        1440      1450      1460      1470      1480      1490

1310      1320      1330      1340      1350      1360
BH 5    GTGACATAGCAGGAACTACTAGTACCCTTCAGGAACAAATAGGATGGATGACAAATAATC
        ::::::::::::::::::::::::::::::::::::::::::::::::::::::::::::
Licuw,  GTGACATAGCAGGAACTACTAGTACCCTTCAGGAACAAATAGGATGGATGACAAATAATC
        1500      1510      1520      1530      1540      1550
```

TABLE II-continued (BH 5 and 8 v. LUCIW)
89.8% identity

```
            1370      1380      1390      1400      1410      1420
BH 5    CACCTATCCCAGTAGGAGAAATTTATAAAAGATGGATAATCCTGGGATTAAATAAAATAG
        ::::::::::::::::::::::::: :::::::::::::::::::::::::::::::::
Licuw,  CACCTATCCCAGTAGGAGAAATCTATAAAAGATGGATAATCCTGGGATTAAATAAAATAG
            1560      1570      1580      1590      1600      1610

1430      1440      1450      1460      1470      1480
BH 5    TAAGGATGTATAGTCCTACCAGCATTCTGGACATAAGACAAGGACCAAAGGAACCCTTTA
        :::: :::::::: :::::::::::::::::::::::::::::::::::::::::::::
Licuw,  TAAGAATGTATAGCCCTACCAGCATTCTGGACATAAGACAAGGACCAAAGGAACCCTTTA
            1620      1630      1640      1650      1660      1670

1490      1500      1510      1520      1530      1540
BH 5    GAGACTATGTAGACCGGTTCTATAAAACTCTAAGAGCCGAGCAAGCTTCACAGGAAGTAA
        :::: ::::::::::::::::::::::::::::::::::: ::::::::::::: ::::
Licuw,  GAGATTATGTAGACCGGTTCTATAAAACTCTAAGAGCCGAACAAGCTTCACAGGATGTAA
            1680      1690      1700      1710      1720      1730

1550      1560      1570      1580      1590      1600
BH 5    AAAATTGGATGACAGAAACCTTGTTGGTCCAAAATGCGAACCCAGATTGTAAGACTATTT
        :::::::::::::::::::::::::::::::::::::: :::::::::::::::::::::
Licuw,  AAAATTGGATGACAGAAACCTTGTTGGTCCAAAATGCAAACCCAGATTGTAAGACTATTT
            1740      1750      1760      1770      1780      1790

1610      1620      1630      1640      1650      1660
BH 5    TAAAAGCATTGGGACCAGCAGCTACTCTAGAAGAAATGATGACAGCATGTCAGGGAGTGG
        ::::::::::::::::::::::::::: ::::::::::::::::::::::::::::::::
Licuw,  TAAAAGCATTGGGACCAGCAGCTACACTAGAAGAAATGATGACAGCATGTCAGGGAGTGG
            1800      1810      1820      1830      1840      1850

1670      1680      1690      1700      1710      1720
BH 5    GAGGACCCGGCCATAAAGCAAGAGTTTTGGCTGAAGCAATGAGCCAAGTAACAAATTCAA
        : :::::::::::::::::::::::::::::::::::: :::::::::::::::::: ::
Licuw,  GGGGACCCGGCCATAAAGCAAGAGTTTTGGCTGAAGCCATGAGCCAAGTAACAAATCCAG
            1860      1870      1880      1890      1900      1910

1730      1740      1750      1760      1770      1780
BH 5    CTACCATAATGATGCAAAGAGGCAATTTTAGGAACCAAAGAAAGATTGTTAAGTGTTTCA
        ::: ::::::::::::: ::::::::::::::::::::::::::: ::::::::::::::
Licuw,  CTAACATAATGATGCAGAGAGGCAATTTTAGGAACCAAAGAAAGACTGTTAAGTGTTTCA
            1920      1930      1940      1950      1960      1970

1790      1800      1810      1820      1830      1840
BH 5    ATTGTGGCAAAGAAGGGCACATAGCAAGAAATTGCAAGGCCCCTAGAAAAAGAGGCTGTT
        ::::::::::::::::  :::::::::: :::::::::: :::::::::  ::: :::
Licuw,  ATTGTGGCAAAGAAGG-CACATAGCCAAAAATTGCAGGGCCCCTAGGAAAA-AGG--GTT
            1980      1990      2000      2010      2020      2030

1850      1860      1870      1880      1890      1900
BH 5    GGAAATGTGGAAAGGAAGGACACCAAATGAAAGATTGTACTGAGAGACAGGCTAATTTTT
        :  : ::::::::::::::::::::::::::::::::: ::::::::::::::::::::
Licuw,  TGGAGTGTGGAAGGGAAGGACACCAAATGAAAGATTGCACTGAGAGACAGGCTAATTTTT
            2040      2050      2060      2070      2080      2090

1910      1920      1930      1940      1950      1960
BH 5    TAGGGAAGATCTGGCCTTCCTACAAGGGAAGGCCAGGGAATTTTCTTCAGAGCAGACCAG
        :::::::::::::::::::::::::::::::::::::::::::::::::::::::::::
Licuw,  TAGGGAAGATCTGGCCTTCCTACAAGGGAAGGCCAGGGAATTTTCTTCAGAGCAGACCAG
            2100      2110      2120      2130      2140      2150

1970      1980      1990      2000      2010      2020
BH 5    AGCCAACAGCCCCACCATTTCTTCAGAGCAGACCAGAGCCAACAGCCCCACCAGAAGAGA
        ::::::::::::::::::                                  :::::::
Licuw,  AGCCAACAGCCCCACCA-----------------------------------GAAGAGA
            2160      2170

2030      2040      2050      2060      2070      2080
BH 5    GCTTCAGGTCTGGGGTAGAGACAACAACTCCCTCTCAGAAGCAGGAGCCGATAGACAAGG
        :::::::::: ::::: ::: :::::::::::::::::::::::::::::::::::::::
Licuw,  GCTTCAGGTTTGGGGAGGAGAAAACAACTCCCTCTCAGAAGCAGGAGCCGATAGACAAGG
            2180      2190      2200      2210      2220      2230

2090      2100      2110      2120      2130      2140
BH 5    AACTGTATCCTTTAACTTCCCTCAGATCACTCTTTGGCAACGACCCCTCGTCACAATAAA
        :::::::::::::::::::::::::::::::::::::::::::::::::::::::: ::
Licuw,  AACTGTATCCTTTAACTTCCCTCAGATCACTCTTTGGCAACGACCCCTCGTCACAATTAA
            2240      2250      2260      2270      2280      2290
```

TABLE II-continued (BH 5 and 8 v. LUCIW)
89.8% identity

```
              2150      2160      2170      2180      2190      2200
BH 5    G-ATAGGGGGCAACTAAAGGAAGCTCTATTAGATACAGGAGCAGATGATACAGTATTAG
        : ::::::::::::::::::::::::::::::::::::::::::::::::::::::::
Licuw,  GGATAGGGGGCAACTAAAGGAAGCTCTATTAGATACAGGAGCAGATGATACAGTATTAG
           2300      2310      2320      2330      2340      2350

2210      2220      2230      2240      2250      2260
BH 5    AAGAAATGAGTTTGCCAGGAAGATGGAAACCAAAAATGATAGGGGGAATTGGAGGTTTTA
        :::::::::: :::::::::::: ::::::::::::::::::::::::::::::::::
Licuw,  AAGAAATGAATTTGCCAGGAAAATGGAAACCAAAAATGATAGGGGGAATTGGAGGTTTTA
           2360      2370      2380      2390      2400      2410

2270      2280      2290      2300      2310      2320
BH 5    TCAAAGTAAGACAGTATGATCAGATACTCATAGAAATCTGTGGACATAAAGCTATAGGTA
        ::::::::::::::::: :::::::::: :::::::::::::::::::::::::::::
Licuw,  TCAAAGTAAGACAGTACGATCAGATACCTGTAGAAATCTGTGGACATAAAGCTATAGGTA
           2420      2430      2440      2450      2460      2470

2330      2340      2350      2360      2370      2380
BH 5    CAGTATTAGTAGGACCTACACCTGTCAACATAATTGGAAGAAATCTGTTGACTCAGATTG
        ::::::::::::::::::::::::::::::::::::::::::::::::::::::::::
Licuw,  CAGTATTAGTAGGACCTACACCTGTCAACATAATTGGAAGAAATCTGTTGACTCAGATTG
           2480      2490      2500      2510      2520      2530

2390      2400      2410      2420      2430      2440
BH 5    GTTGCACTTTAAATTTTCCCATTAGTCCTATTGAAACTGTACCAGTAAAATTAAAGCCAG
        :::: :::::::::: ::::::::::::::::::::::::::::::::::::::::::
Licuw,  GTTGTACTTTAAATTTCCCCATTAGTCCTATTGAAACTGTACCAGTAAAATTAAAGCCAG
           2540      2550      2560      2570      2580      2590

2450      2460      2470      2480      2490      2500
BH 5    GAATGGATGGCCCAAAAGTTAAACAATGGCCATTGACAGAAGAAAAAATAAAAGCATTAG
        :::::::::::::::::::::: :::::::::::::::::::::::::::::::::::
Licuw,  GAATGGATGGCCCAAAAGTTAAGCAATGGCCATTGACAGAAGAAAAAATAAAAGCATTAG
           2600      2610      2620      2630      2640      2650

2510      2520      2530      2540      2550      2560
BH 5    TAGAAATTTGTACAGAAATGGAAAAGGAAGGGAAAATTTCAAAAATTGGGCCTGAAAATC
        ::::  :: :::::::::::::::::::::::::::::::::::::::::::::::::
Licuw,  TAGAGATATGTACAGAAATGGAAAAGGAAGGGAAAATTTCAAAAATTGGGCCTGAAAATC
           2660      2670      2680      2690      2700      2710

2570      2580      2590      2600      2610      2620
BH 5    CATACAATACTCCAGTATTTGCCATAAAGAAAAAAGACAGTACTAAATGGAGAAAATTAG
        :::::::::::::::::::::: :::::::::::::::::::::::::::::::: :::
Licuw,  CATACAATACTCCAGTATTTGCTATAAAGAAAAAAGACAGTACTAAATGGAGAAAACTAG
           2720      2730      2740      2750      2760      2770

2630      2640      2650      2660      2670      2680
BH 5    TAGATTTCAGAGAACTTAATAGGAGAACTCAAGACTTCTGGGAAGTTCAATTGGGAATAC
        :::::::::::::::::::: :::::::::::::::::::::::::: :: ::::::::
Licuw,  TAGATTTCAGAGAACTTAATAAAAGAACTCAAGACTTCTGGGAAGTTCAGTTAGGAATAC
           2780      2790      2800      2810      2820      2830

2690      2700      2710      2720      2730      2740
BH 5    CACATCCCGCAGGGTTAAAAAA-GAAAAAATCAGTAACAGTACTGGATGTGGGTGATGCA
        :::: ::::::::::::::::: ::::::::::::::::::::: :::::::::::::
Licuw,  CACA-CCCGCAGGGTTAAAAAAAGAAAAAATCAGTAACAGTATTGGATGTGGGTGATGCA
           2840      2850      2860      2870      2880      2890

2750      2760      2770      2780      2790      2800
BH 5    TATTTTTCAGTTCCCTTAGATGAAGACTTCAGGAAGTATACTGCATTTACCATACCTAGT
        :: :::::::::::::::::: :::::::: :: ::::::::::::::::::::::::
Licuw,  TACTTTTCAGTTCCCTTAGATAAAGACTTTAGAAAGTATACTGCATTTACCATACCTAGT
           2900      2910      2920      2930      2940      2950

2810      2820      2830      2840      2850      2860
BH 5    ATAAATAATGAGACACCAGGGATTAGATATCAGTACAATGTG-CTTCCACAGGGATGGAA
        ::::: ::::::::::::::::::::::::::::::::::: :: ::::::::::::::
Licuw,  ATAAACAATGAGACACCAGGGATTAGATATCAGTACAATGTGGCTGCCACAGGGATGGAA
           2960      2970      2980      2990      3000      3010
```

TABLE II-continued (BH 5 and 8 v. LUCIW)
89.8% identity

```
              2870      2880      2890      2900      2910      2920
BH 5    AGGATCACCAGCAATATTCCAAAGTAGCATGACAAAAATCTTAGAGCCTTTTAGAAAACA
        ::::::::::::::::::::::::::::::::::::::::::::::::::::::::::::
Licuw,  AGGATCACCAGCAATATTCCAAAGTAGCATGACAAAAATCTTAGAGCCTTTTAGAAAACA
              3020      3030      3040      3050      3060      3070

2930      2940      2950      2960      2970      2980
BH 5    AAATCCAGACATAGTTATCTATCAATACATGGATGATTTGTATGTAGGATCTGACTTAGA
         :::::::::::::::::::::::::::::::::::::::::::::::::::::::::::
Licuw,  GAATCCAGACATAGTTATCTATCAATACATGGATGATTTGTATGTAGGATCTGACTTAGA
              3080      3090      3100      3110      3120      3130

2990      3000      3010      3020      3030      3040
BH 5    AATAGGGCAGCATAGAACAAAAATAGAGGAGCTGAGACAACATCTGTTGAGGTGGGGATT
        :::::::::::::::::::::::::::::::::::      ::::::::::::::::::
Licuw,  AATAGGGCAGCATAGAACAAAAATAGAGGAACTGAGACAGCATCTGTTGAGGTGGGGATT
              3140      3150      3160      3170      3180      3190

3050      3060      3070      3080      3090      3100
BH 5    TACCACACCAGACAAAAAACATCAGAAAGAACCTCCATTCCTTTGGATGGGTTATGAACT
        ::::::::::::::::::::::::::::::::::::::::::::::::::::::::::::
Licuw,  TACCACACCAGACAAAAAACATCAGAAAGAACCTCCATTCCTTTGGATGGGTTATGAACT
              3200      3210      3220      3230      3240      3250

3110      3120      3130      3140      3150      3160
BH 5    CCATCCTGATAAATGGACAGTACAGCCTATAGTGCTGCCAGAAAAAGACAGCTGGACTGT
        ::::::::::::::::::::::::::::::::::: ::::::::::::::::::::::::
Licuw,  CCATCCTGATAAATGGACAGTACAGCCTATAATGCTGCCAGAAAAAGACAGCTGGACTGT
              3260      3270      3280      3290      3300      3310

3170      3180      3190      3200      3210      3220
BH 5    CAATGACATACAGAAGTTAGTGGGAAAATTGAATTGGGCAAGTCAGATTTATCCAGGGAT
        :::::::::::::::::::::::::::::::::::::::::::::::::::  :::::::
Licuw,  CAATGACATACAGAAGTTAGTGGGAAAATTGAATTGGGCAAGTCAGATTTATGCAGGGAT
              3320      3330      3340      3350      3360      3370

3230      3240      3250      3260      3270      3280
BH 5    TAAAGTAAGGCAATTATGTAAACTCCTTAGAGGAACCAAAGCACTAACAGAAGTAATACC
        ::::::: :::  ::::::::::::::::::::::::::::::::::::::::::::::
Licuw,  TAAAGTAAAGCAGTTATGTAAACTCCTTAGAGGAACCAAAGCACTAACAGAAGTAATACC
              3380      3390      3400      3410      3420      3430

3290      3300      3310      3320      3330      3340
BH 5    ACTAACAGAAGAAGCAGAGCTAGAACTGGCAGAAAACAGAGAGATTCTAAAAGAACCAGT
        :::::::::::::::::::::::::::::::::::::::  :::::::::::::::::::
Licuw,  ACTAACAGAAGAAGCAGAGCTAGAACTGGCAGAAAACAGGGAGATTCTAAAAGAACCAGT
              3440      3450      3460      3470      3480      3490

3350      3360      3370      3380      3390      3400
BH 5    ACATGGAGTGTATTATGACCCATCAAAAGACTTAATAGCAGAAATACAGAAGCAGGGGCA
        ::::: ::: :::::::::::::::::::::::::: :::::::::::::::::::::::
Licuw,  ACATGAAGTATATTATGACCCATCAAAAGACTTAGTAGCAGAAATACAGAAGCAGGGGCA
              3500      3510      3520      3530      3540      3550

3410      3420      3430      3440      3450      3460
BH 5    AGGCCAATGGACATATCAAATTTATCAAGAGCCATTTAAAAATCTGAAAACAGGAAAATA
        ::::::::::::::::::::::::::::::::::::::::::::::::::::::::::
Licuw,  AGGCCAATGGACATATCAAATTTATCAAGAGCCATTTAAAAATCTGAAAACAGGAAAGTA
              3560      3570      3580      3590      3600      3610

3470      3480      3490      3500      3510      3520
BH 5    TGCAAGAATGAGGGGTGCCCACACTAATGATGTAAAACAATTAACAGAGGCAGTGCAAAA
        ::::::  :::::::::::::::::::::::::::::: :::::::::::::::::::::
Licuw,  TGCAAGGATGAGGGGTGCCCACACTAATGATGTAAAACAGTTAACAGAGGCAGTGCAAAA
              3620      3630      3640      3650      3660      3670

3530      3540      3550      3560      3570      3580
BH 5    AATAACCACAGAAAGCATAGTAATATGGGGAAAGACTCCTAAATTTAAACTACCCATACA
        :  :::::::::::::::::::::::::::::::: ::::::::: ::::::::::::::
Licuw,  AGTATCCACAGAAAGCATAGTAATATGGGGAAAGATTCCTAAATTTAAACTACCCATACA
              3680      3690      3700      3710      3720      3730

3590      3600      3610      3620      3630      3640
BH 5    AAAAGAAACATGGGAAACATGGTGGACAGAGTATTGGCAAGCCACCTGGATTCCTGAGTG
        :::  :::::::::::: :::::::::: :::::::::::::::: ::::::::::::::
Licuw,  AAAGGAAACATGGGAAGCATGGTGGATGGAGTATTGGCAAGCTACCTGGATTCCTGAGTG
              3740      3750      3760      3770      3780      3790
```

TABLE II-continued (BH 5 and 8 v. LUCIW)
89.8% identity

```
            3650       3660       3670       3680       3690       3700
BH 5     GGAGTTTGTTAATACCCCTCCTTTAGTGAAATTATGGTACCAGTTAGAGAAAGAACCCAT
         :::::::::: :::::::::::: :::::::::::::::::::::::::::::::::::
Licuw,   GGAGTTTGTCAATACCCCTCCCTTAGTGAAATTATGGTACCAGTTAGAGAAAGAACCCAT
            3800       3810       3820       3830       3840       3850

3710       3720       3730       3740       3750       3760
BH 5     AGTAGGAGCAGAAACCTTCTATGTAGATGGGGCAGCTAGCAGGGAGACTAAATTAGGAAA
         ::::::::::::::::: ::::::::::::::::::::: ::::::::::::::::::::
Licuw,   AGTAGGAGCAGAAACTTTCTATGTAGATGGGGCAGCTAATAGGGAGACTAAATTAGGAAA
            3860       3870       3880       3890       3900       3910

3770       3780       3790       3800       3810       3820
BH 5     AGCAGGATATGTTACTAATAGAGGAAGACAAAAAGTTGTCACCCTAACTGACACAACAAA
         :::::::::::::::::: : :::::::::::::::::::: :: :::::::::::::::
Licuw,   AGCAGGATATGTTACTGACAGAGGAAGACAAAAAGTTGTCTCCATAGCTGACACAACAAA
            3920       3930       3940       3950       3960       3970

3830       3840       3850       3860       3870       3880
BH 5     TCAGAAGACTGAATTACAAGCAATTCATCTAGCTTTGCAGGATTCGGGATTAGAAGTAAA
         ::::::::::::::::::::::::::::::::::::::::::::::::::::::::::::
Licuw,   TCAGAAGACTGAATTACAAGCAATTCATCTAGCTTTGCAGGATTCGGGATTAGAAGTAAA
            3980       3990       4000       4010       4020       4030

3890       3900       3910       3920       3930       3940
BH 5     TATAGTAACAGACTCACAATATGCATTAGGAATCATTCAAGCACAACCAGATAAAAGTGA
          :::::::::::::::::::::::::::::::::::::::::::::::::::::: :::::
Licuw,   CATAGTAACAGACTCACAATATGCATTAGGAATCATTCAAGCACAACCAGATAAGAGTGA
            4040       4050       4060       4070       4080       4090

3950       3960       3970       3980       3990       4000
BH 5     ATCAGAGTTAGTCAATCAAATAATAGAGCAGTTAATAAAAAAGGAAAAGGTCTATCTGGC
         :::::::::::::: ::::::::::::::::::::::::::::::::::::::: :::::
Licuw,   ATCAGAGTTAGTCAGTCAAATAATAGAGCAGTTAATAAAAAAGGAAAAGGTCTACCTGGC
            4100       4110       4120       4130       4140       4150

4010       4020       4030       4040       4050       4060
BH 5     ATGGGTACCAGCACACAAAGGAATTGGAGGAAATGAACAAGTAGATAAATTAGTCAGTGC
         ::::::::::::::::::::::::::::::::::::::::::::::::::::::::::::
Licuw,   ATGGGTACCAGCACACAAAGGAATTGGAGGAAATGAACAAGTAGATAAATTAGTCAGTGC
            4160       4170       4180       4190       4200       4210

4070       4080       4090       4100       4110       4120
BH 5     TGGAATCAGGAAAATACTATTTTTAGATGGAATAGATAAGGCCCAAGAAGAACATGAGAA
         ::::::::::::: :::::::::: :::::::::::::::::::::::::::::::::::
Licuw,   TGGAATCAGGAAAGTACTATTTTTGAATGGAATAGATAAGGCCCAAGAAGAACATGAGAA
            4220       4230       4240       4250       4260       4270

4130       4140       4150       4160       4170       4180
BH 5     ATATCACAATAATTGGAGAGCAATGGCTAGTGATTTTAACCTGCCACCTGTAGTAGCAAA
         :::::::: :::::::::::::::::::::::::::::::::::::::::::::::::::
Licuw,   ATATCACAGTAATTGGAGAGCAATGGCTAGTGATTTTAACCTGCCACCTGTAGTAGCAAA
            4280       4290       4300       4310       4320       4330

4190       4200       4210       4220       4230       4240
BH 5     AGAAATAGTAGCCAGCTGTGATAAATGTCAGCTAAAAGGAGAAGCCATGCATGGACAAGT
         ::::::::::::::::::::::::::::::::::::::::::::::::::::::::::::
Licuw,   AGAAATAGTAGCCAGCTGTGATAAATGTCAGCTAAAAGGAGAAGCCATGCATGGACAAGT
            4340       4350       4360       4370       4380       4390

4250       4260       4270       4280       4290       4300
BH 5/8   AGACTGTAGTCCAGGAATATGGCAACTAGATTGTACACATTTAGAAGGAAAAGTTATCCT
         :::::::::::::::::::::::::::::::::::::::::: :::::::::: ::::::
Licuw,   AGACTGTAGTCCAGGAATATGGCAACTAGATTGTACACATCTAGAAGGAAAAATTATCCT
            4400       4410       4420       4430       4440       4450

4310       4320       4330       4340       4350       4360
BH 5     GGTAGCAGTTCATGTAGCCAGTGGATATATAGAAGCAGAAGTTATTCCAGCAGAAACAGG
         ::::::::::::::::::::::::::::::::::::::::::::::::::::::: :::::
Licuw,   GGTAGCAGTTCATGTAGCCAGTGGATATATAGAAGCAGAAGTTATTCCAGCAGAGACAGG
            4460       4470       4480       4490       4500       4510
```

TABLE II-continued (BH 5 and 8 v. LUCIW)
89.8% identity

```
           4370      4380      4390      4400      4410      4420
BH 5   GCAGGAAACAGCATATTTTCTTTTAAAATTAGCAGGAAGATGGCCAGTAAAAACAATACA
       ::::::::::::::::::::::::: :::::::::::::::::::::::::::::::::
Licuw, GCAGGAAACAGCATATTTTCTCTTAAAATTAGCAGGAAGATGGCCAGTAAAAACAATACA
           4520      4530      4540      4550      4560      4570

4430      4440      4450      4460      4470      4480
BH 5   TACAGACAATGGCAGCAATTTCACCAGTGCTACGGTTAAGGCCCGCCTGTTGGTGGGCGGG
       ::::::::::::::::::::::::::: ::::::::::::::::::::::::::::: :
Licuw, TACAGACAATGGCAGCAATTTCACCAGTACTACGGTTAAGGCCCGCCTGTTGGTGGGCAGG
           4580      4590      4600      4610      4620      4630

4490      4500      4510      4520      4530      4540
BH 5   AATCAAGCAGGAATTTGGAATTCCCTACAATCCCCAAAGTCAAGGAGTAGTAGAATCTAT
         ::::::::::::::: ::: ::::::::::::::::::::::::::::::::::::::
Licuw, GATCAAGCAGGAATTTGGCATTCCCTACAATCCCCAAAGTCAAGGAGTAGTAGAATCTAT
           4640      4650      4660      4670      4680      4690

4550      4560      4570      4580      4590      4600
BH 5   GAATAAAGAATTAAAGAAAATTATAGGACAGGTAAGAGATCAGGCTGAACATCTTAAGAC
       ::::: ::::::::::::::::::::::::::::::::::::::::::::: ::::::::
Licuw, GAATAATGAATTAAAGAAAATTATAGGACAGGTAAGAGATCAGGCTGAACACCTTAAGAC
           4700      4710      4720      4730      4740      4750

4610      4620      4630      4640      4650      4660
BH 5   AGCAGTACAAATGGCAGTATTCATCCACAATTTTAAAAGAAAAGGGGGGATTGGGGGGTA
       ::::::::::::::::::::::::::::::::::::::::::::::::::::::::: :
Licuw, AGCAGTACAAATGGCAGTATTCATCCACAATTTTAAAAGAAAAGGGGGGATTGGGGGATA
           4760      4770      4780      4790      4800      4810

4670      4680      4690      4700      4710      4720
BH 5   CAGTGCAGGGGAAAGAATAGTAGACATAATAGCAACAGACATACAAACTAAAGAATTACA
       :::::::::::::::::::::::::::::::::::::::::::::::::::::: ::::
Licuw, CAGTGCAGGGGAAAGAATAGTAGACATAATAGCAACAGACATACAAACTAAAGAACTACA
           4820      4830      4840      4850      4860      4870

4730      4740      4750      4760      4770      4780
BH 5   AAAACAAATTACAAAAATTCAAAATTTTCGGGTTTATTACAGGGACAGCAGAAATCCACT
       :::::::::::::::::::::::::::::::::::::::::::::: :: :::: :::::
Licuw, AAAGCAAATTACAAAAATTCAAAATTTTCGGGTTTATTACAGGGACAACAAAGATCCCCT
           4880      4890      4900      4910      4920      4930

4790      4800      4810      4820      4830      4840
BH 5   TTGGAAAGGACCAGCAAAGCTCCTCTGGAAAGGTGAAGGGGCAGTAGTAATACAAGATAA
       ::::::::::::::::::::: ::::: ::::::::::::::::::::::::::::::::
Licuw, TTGGAAAGGACCAGCAAAGCTTCTCTGCAAAGGTGAAGGGGCAGTAGTAATACAAGATAA
           4940      4950      4960      4970      4980      4990

4850      4860      4870      4880      4890      4900
BH 5   TAGTGACATAAAAGTAGTGCCAAGAAGAAAAGCAAAGATCATTAGGGATTATGGAAAACA
       :::::::::::::::::::::::::::::::::::::: :::::::: ::::::::::::
Licuw, TAGTGACATAAAAGTAGTGCCAAGAAGAAAAGCAAAAATCATTAGGGATTATGGAAAACA
           5000      5010      5020      5030      5040      5050

4910      4920      4930      4940      4950      4960
BH 5   GATGGCAGGTGATGATTGTGTGGCAAGTAGACAGGATGAGGATTAGAACATGGAAAAGTT
       ::::::::::::::::::::         :::::::::::::::::::::::::::::::
Licuw, GATGGCAGGTGATGATTGTGT---AAGTAGACAGGATGAGGATTAGAACATGGAAAAGTT
           5060      5070      5080      5090      5100      5110

4970      4980      4990      5000      5010      5020
BH 5   TAGTAAAACACCATATGTATGTTTCAGGGAAAGCTAGGGGATGGTTTTATAGACATCACT
       ::::::::::::::::::::: ::::: :::::::: :::::::::::: ::: :::::::
Licuw, TAGTAAAACACCATATGTATATTTCAAAGAAAGCTAAAGGATGGTTTT-TAG-CATCACT
           5120      5130      5140      5150      5160      5170

5030      5040      5050      5060      5070      5080
BH 5   ATGAAAGCCCTCATCCAAGAATAAGTTCAGAAGTACACATCCCACTAGGGGATGCTAGAT
       ::::::  :::::::::::::: :::::::::::::::::::: :::::::::::::::
Licuw, -TGAAAGTACTCATCCAAGAGTAAGTTCAGAAGTACACATCCCCCTAGGGGATGCTAAAT
           5180      5190      5200      5210      5220      5230

5090      5100      5110      5120      5130      5140
BH 5   TGGTAATAACAACATATTGGGGTCTGCATACA-GGAGAAAGAGACTGGCATTTGGGTCAG
       ::::::::::::::::::::::::::::::::  :::::::::::: ::::::::: :::
Licuw, TGGTAATAACAACATATTGGGGTCTGCATACAAGGAGAAAGAGAATGGCATTTGGG-CAG
           5240      5250      5260      5270      5280
```

TABLE II-continued (BH 5 and 8 v. LUCIW)
89.8% identity

```
              5150      5160      5170      5180      5190      5200
BH 5    GGAGTCTCCATAGAATGGAGGAAAAGGAGATATAGCACACAAGTAGACCCTGAACTAGCA
        ::  :::  :::::::::::  :::       ::  :::::::::::::::::  ::::::
Licuw,  GG-GTCGCCATAGAATGGAGAAAA----GAATTAGCACACAAGTAGACCCTGGCCTAGCA
           5290      5300      5310      5320      5330      5340

5210      5220      5230      5240      5250      5260
BH 5    GACCAACTAATTCATCTGTATTACTTTGATTGTTTTTCAGACTCTGCTATAAGAAAGGCC
        ::::::::::::::::::::  ::::  ::::  :::::::::  :::::::  :::  :::
Licuw,  GACCAACTAATTCATCTGCATTATTTTGATTGTTTTTCAGAATCTGCTATAAAAAATGCC
           5350      5360      5370      5380      5390      5400

5270      5280      5290      5300      5310      5320
BH 5    TTATTAGGACACATAGTTAGCCCTAGGTGTGAATATCAAGCAGGACATAACAAGGTAGGA
        ::::::::  :  :  ::::::  :::::  ::::  :::::::::::::::::::::::::
Licuw,  ATATTAGGATATAGAGTTAGTCCTAGCTGTGAATATCAAGCAGGACATAACAAGGTAGGA
           5410      5420      5430      5440      5450      5460

5330      5340      5350      5360      5370      5380
BH 5    TCTCTACAATACTTGGCACTAGCAGCATTAATAACACCAAAAAAGGGAAAGCCACCTTTG
        :::::::::::::::::::::::::::::::::::::::::::::::   :::::::::::
Licuw,  TCTCTACAATACTTGGCACTAGCAGCATTAATAACACCAAAAAAGACAAAGCCACCTTTG
           5470      5480      5490      5500      5510      5520

5390      5400      5410      5420      5430      5440
BH 5    CCTAGTGTTACGAAACTGACAGAGGATAGATGGAACAAGCCCCAGAAGACCAAGGGCCAC
        ::::::::::  ::::::::::::::::::::::::::::::::::::::::::::::::
Licuw,  CCTAGTGTTAAGAAACTGACAGAGGATAGATGGAACAAGCCCCAGAAGACCAAGGGCCAC
           5530      5540      5550      5560      5570      5580

5450      5460      5470      5480      5490      5500
BH 5    AGAGGGAGCCACACAATGAATGGACACTAGAGCTTTTAGAGGAGCTTAAGAATGAAGCTG
        ::::::::::  ::::::::::::::::::::::::::::::::::::::::  :::::::
Licuw,  AGAGGGAGCCATACAATGAATGGACACTAGAGCTTTTAGAGGAGCTTAAGAGAGAAGCTG
           5590      5600      5610      5620      5630      5640

5510      5520      5530      5540      5550      5560
BH 5    TTAGACATTTTCCTAGGATTTGGCTCCATGGCTTAGGGCAACATATCTATGAAACTTATG
        ::::::::::::::::::  :::::::::  :::::::  :::  :::::::::::::::
Licuw,  TTAGACATTTTCCTAGGCCATGGCTCCATAGCTTAGGACAATATATCTATGAAACTTATG
           5650      5660      5670      5680      5690      5700

5570      5580      5590      5600      5610      5620
BH 5    GGGATACTTGGGCAGGAGTGGAAGCCATAATAAGAATTCTGCAACAACTGCTGTTTATCC
        :::::::::::::::::::::::::::::::::::::::::::::::::::::::::::  :
Licuw,  GGGATACTTGGGCAGGAGTGGAAGCCATAATAAGAATTCTGCAACAACTGCTGTTTATTC
           5710      5720      5730      5740      5750      5760

5630      5640      5650      5660      5670      5680
BH 5    ATTTTCAGAATTGGGTGTCGACATAGCAGAATAGGCGTTACTCAACGAGGGAGAGCAAGA
        ::::  :::::::::::::::  :::::::::::::::::  :::  :::::::::::::::
Licuw,  ATTT-CAGAATTGGGTGTCAACATAGCAGAATAGGCGTTATTCAACAGAGGAGAGCAAGA
           5770      5780      5790      5800      5810      5820

5690      5700      5710      5720      5730
BH 5    A---ATGGAGCCAGTAGATCCTAGACTAGAGCCCTGGAAGCATCCAGGAAGTCAGCCTAA
        :   :::::::::::::::::::::  :::::::::::::::::::::::::::::::::
Licuw,  AGAAATGGAGCCAGTAGATCCTAATCTAGAGCCCTGGAAGCATCCAGGAAGTCAGCCTAG
           5830      5840      5850      5860      5870      5880

5740      5750      5760      5770      5780      5790
BH 5    AACTGCTTGTACCACTTGCTATTGTAAAAAGTGTTGCTTTCATTGCCAAGTTTGTTTCAT
        ::::::::::::  ::  ::::::::::::::::::::::::::::::::   :  :::::::
Licuw,  GACTGCTTGTAACAATTGCTATTGTAAAAAGTGTTGCTTTCATTGCTACGCGTGTTTCAC
           5890      5900      5910      5920      5930      5940

5800      5810      5820      5830      5840      5850
BH 5    AACAAAAGCCTTAGGCATCTCCTATGGCAGGAAGAAGCGGAGACAGCGACGAAGAGCTC
        ::  :::::::::::::::::::::::::::::::::::::::::::::::::::::::
Licuw,  AAGAAAAGGCTTAGGCATCTCCTATGGCAGGAAGAAGCGGAGACAGCGACGAAGAGCTC
           5950      5960      5970      5980      5990      6000
```

TABLE II-continued (BH 5 and 8 v. LUCIW)
89.8% identity

```
        5860      5870      5880      5890      5900      5910
BH 8    GAGCTCATCGAAGCAGTCAGACTCATCAAGTTTCTCTATCAAAGCAGTAAGTAGTACATGT
        ::::  ::  ::::::::::::::::::::  ::::::::::::::::::::::  ::::
Licuw,  ---CTCAG-GA--CAGTCAGACTCATCAAGCTTCTCTATCAAAGCAGTAAGTAGTAAATGT
                  6010      6020      6030      6040      6050

5920      5930      5940      5950      5960      5970
BH 8    AATGCAACCTATACAATA---GCAATAGTAGCATTAGTAGTAGCAATAATAATAGCAAT
        ::::::::  ::  ::::::::   :::::::::  :::::::::  ::::::::::::::
Licuw,  AATGCAATCTTTACAAATATTAGCAATAGTATCATTAGTAGTAGTAGCAATAATAATAGCAAT
        6060      6070      6080      6090      6100      6110

5980      5990      6000      6010      6020      6030
BH 8    AGTTGTGTGGTCCATAGTAATCATAGAATATAGGAAAATATTAAGACAAAGAAAAATAGA
        :::::::::  ::::::::  ::::::::::::::::::::::::::::::::::  ::::
Licuw,  AGTTGTGTGGACCATAGTACTCATAGAATATAGGAAAATATTAAGACAAAGAAAA-TAGA
        6120      6130      6140      6150      6160      6170

6040      6050      6060      6070      6080      6090
BH 8    CAGGTTAATTGATAGACTAATAGAAAGAGCAGAAGACAGTGGCAATGAGAGTGAAGGAGA
        :::  ::::::::::::: :::  :::::  :::::::::::::::::::  :::::::: ::
Licuw,  CAGATTAATTGATAGAATAAGAGAAAAAGCAGAAGACAGTGGCAATGAAAGTGAAGGGGA
        6180      6190      6200      6210      6220      6230

6100      6110      6120      6130      6140
BH 8    ---------AATATCAGCACTTGTGGAGATGGGGGTGGAGATGGGGCACCATGCTCCTTG
                 :  :::::::::::::::::::::::::            :::::  :::::::::
Licuw,  CCAGGAGGAATTATCAGCACTTGTGGAGATGGG------------GCACCTTGCTCCTTG
        6240      6250      6260                  6270      6280

6150      6160      6170      6180      6190      6200
BH 8    GGATGTTGATGATCTGTAGTGCTACAGAAAAATTGTGGGTCACAGTCTATTTAGGGGTAC
        ::::::::::::::::::::::::::::::::::::::::::::::::  ::::  ::  ::::
Licuw,  GGATGTTGATGATCTGTAGTGCTACAGAAAAATTGTGGGTCACAGTTTATTATGGAGTAC
        6290      6300      6310      6320      6330      6340

6210      6220      6230      6240      6250      6260
BH 8    CTGTGTGGAAGGAAGCAACCACCACTCTATTTTGTGCATCAGATGCTAAAGCATATGATA
        ::::::::::  :::::::::  ::  :::::::::::::::::::::::  ::  ::::::::::
Licuw,  CTGTGTGGAAAGAAGCAACTACCACTCTATTTTGTGCATCAGATGCTAGAGCATATGATA
        6350      6360      6370      6380      6390      6400

6270      6280      6290      6300      6310      6320
BH 8    CAGAGGTACATAATGTTTGGGCCACACATGCCTGTGTACCCACAGACCCCAACCCACAAG
        ::::::::::::::::::::::::::::::::::::::::::::::::::::::::::::
Licuw,  CAGAGGTACATAATGTTTGGGCCACACATGCCTGTGTACCCACAGACCCCAACCCACAAG
        6410      6420      6430      6440      6450      6460

6330      6340      6350      6360      6370      6380
BH 8    AAGTAGTATTGGTAAATGTGACAGAAAATTTTAACATGTGGAAAAATGACATGGTAGAAC
        :::::::::::::  :::::::::::::::::::::::::::::::::::  :::::::::::
Licuw,  AAGTAGTATTGGGAAATGTGACAGAAAATTTTAACATGTGGAAAAATAACATGGTAGAAC
        6470      6480      6490      6500      6510      6520

6390      6400      6410      6420      6430      6440
BH 8    AGATGCATGAGGATATAATCAGTTTATGGGATCAAAGCCTAAAGCCATGTGTAAAATTAA
        ::::::::  ::::::::::::::::::::::::::::::::::::::::::::::::::
Licuw,  AGATGCAGGAGGATATAATCAGTTTATGGGATCAAAGCCTAAAGCCATGTGTAAAATTAA
        6530      6540      6550      6560      6570      6580

6450      6460      6470      6480      6490      6500
BH 8    CCCCACTCTGTGTTAGTTTAAAGTGCACTGATTTGAAGAATGATACTAATACCAATAGTA
        ::::::::::::::  ::::::  :::::::::::::  :::  ::::::::::::::::::
Licuw,  CCCCACTCTGTGTTACTTTAAATTGCACTGATTTGGGGAAGGCTACTAATACCAATAGTA
        6590      6600      6610      6620      6630      6640

6510      6520      6530      6540      6550      6560
BH 8    GTAGCGGGAGAATGATAATGGAGAAAGGAGAGATAAAAAACTGCTCTTTCAATATCAGCA
        :::  :::  :    :::      ::::::::  ::::::::::::::::::::::::  ::
Licuw,  GTAATTGGAAAGAAGAAATA---AAAGGAGAAATAAAAAACTGCTCTTTCAATATCACCA
        6650      6660          6670      6680      6690      6700

6570      6580      6590      6600      6610      6620
BH 8    CAAGCAAAAGAGGTAAGGTGCAGAAAGAATATGCATTTTTTTATAAACTTGATATAATAC
        :::::  :::::  ::::  :  ::::::::::  :::::  :::::   ::  ::::::  :::
Licuw,  CAAGCATAAGAGATAAGATTCAGAAAGAAAATGCACTTTTTCGTAACCTTGATGTAGTAC
        6710      6720      6730      6740      6750      6760
```

TABLE II-continued (BH 5 and 8 v. LUCIW)
89.8% identity

```
            6630      6640      6650      6660      6670
BH 8   CAATAGATAATGATA------CTACCAGCTATAC---------GTTGACAAGTTGTAACA
       ::::::::::::: ::      :::::: ::::::         ::::: : :::::::::
Licuw, CAATAGATAATGCTAGTACTACTACCAACTATACCAACTATAGGTTGATACATTGTAACA
            6770      6780      6790      6800      6810      6820

6680      6690      6700      6710      6720      6730
BH 8   CCTCAGTCATTACACAGGCCTGTCCAAAGGTATCCTTTGAGCCAATTCCCATACATTATT
        ::::::::::::::::::::::::::::::::::: :::::::::::::::::::::::
Licuw, GATCAGTCATTACACAGGCCTGTCCAAAGGTATCATTTGAGCCAATTCCCATACATTATT
            6830      6840      6850      6860      6870      6880

6740      6750      6760      6770      6780      6790
BH 8   GTGCCCCGGCTGGTTTTGCGATTCTAAAATGTAATAATAAGACGTTCAATGGAACAGGAC
       :: :::::::::::::::::::::::::: ::::::::::: :::::::::::: :::::
Licuw, GTACCCCGGCTGGTTTTGCGATTCTAAAGTGTAATAATAAAACGTTCAATGGAAAAGGAC
            6890      6900      6910      6920      6930      6940

6800      6810      6820      6830      6840      6850
BH 8   CATGTACAAATGTCAGCACAGTACAATGTACACATGGAATTAGGCCAGTAGTATCAACTC
       ::::::::::::::::::::::::::::::::::::::::::::::::: :::: ::::::
Licuw, CATGTACAAATGTCAGCACAGTACAATGTACACATGGAATTAGGCCAATAGTGTCAACTC
            6950      6960      6970      6980      6990      7000

6860      6870      6880      6890      6900
BH 8   AACTG-CTGTTAAATGGCAGTCTAGCAGAAGAAGAGGTAGTAATTAGATCTGTCAATTTC
       ::::: ::::::::::::::::::::::::::::::::::::::::::::::: ::::::
Licuw, AACTGTCTGTTAAATGGCAGTCTAGCAGAAGAAGAGGTAGTAATTAGATCTGACAATTTC
            7010      7020      7030      7040      7050      7060

6910      6920      6930      6940      6950      6960
BH 8   ACGGACAATGCTAAAACCATAATAGTACAGCTGAACACATCTGTAGAAATTAATTGTACA
       :::  :::::::::::::::::::::::::::::::  :::::::: :::::: ::::::
Licuw, ACGAACAATGCTAAAACCATAATAGTACAGCTGAATGAATCTGTAGCAATTAACTGTACA
            7070      7080      7090      7100      7110      7120

6970      6980      6990      7000      7010      7020
BH 8   AGACCCAACAACAATACAAGAAAAAGTATCCAAATCCAGAGGGGACCAGGGAGAGCATTT
       ::::::::::::::::::::::::::::::: ::         ::::::::::::::::::
Licuw, AGACCCAACAACAATACAAGAAAAAGTATCTATATA------GGACCAGGGAGAGCATTT
            7130      7140      7150      7160      7170

7030      7040      7050      7060      7070      7080
BH 8   GTTACAATAGGAAAAATA---GGAAATATGAGACAAGCACATTGTAACATTAGTAGAGCA
       ::::: ::::: ::::     :::  ::: :::::::::::::::::::::::::::::::
Licuw, CATACAACAGGAAGAATAATAGGAGATATAAGAAAAGCACATTGTAACATTAGTAGAGCA
            7180      7190      7200      7210      7220      7230

7090      7100      7110      7120      7130      7140
BH 8   AAATGGAATGCCACTTTAAAACAGATAGATAGCAAATTAAGAGAACAATTTGGAAATAAT
        :::::::: :::::::: ::::::::::: ::::: :::::::::: :::::::::::
Licuw, CAATGGAATAACACTTTAGAACAGATAGTTAAAAAATTAAGAGAACAGTTTGGGAATAAT
            7240      7250      7260      7270      7280      7290

7150      7160      7170      7180      7190      7200
BH 8   AAAACAATAATCTTTAAGCAGTCCTCAGGAGGGGACCCAGAAATTGTAACGCACAGTTTT
       :::::::: :::::: :: :::::::::::::::::::::::::::::::: ::::::::
Licuw, AAAACAATAGTCTTTAATCAATCCTCAGGAGGGGACCCAGAAATTGTAATGCACAGTTTT
            7300      7310      7320      7330      7340      7350

7210      7220      7230      7240      7250      7260
BH 8   AATTGTGGAGGGGAATTTTTCTACTGTAATTCAACACAACTGTTTAATAGTACTTGGAGT
       :::::: :::::::::::::::::::::::::: ::::::::::::::::: ::::::::
Licuw, AATTGTAGAGGGGAATTTTTCTACTGTAATACAACACAACTGTTTAATAATACATGGAG-
            7360      7370      7380      7390      7400      7410

7270      7280      7290      7300      7310
BH 8   ACTAAAGGGTCAAATAACACTGAAGGAAGT---------GACACAATCACCCTCCCATGC
        :: :::: :::::::::: :         ::::::::::: :::::::
Licuw, --------GTTAAATCACACTGAAGGAACTAAAGGAAATGACACAATCATACTCCCATGT
            7420      7430      7440      7450      7460
```

TABLE II-continued (BH 5 and 8 v. LUCIW)
89.8% identity

```
        7320      7330      7340      7350      7360      7370
BH 8   AGAATAAAACAAATTATAAACATGTGGCAGGAAGTAGGAAAAGCAATGTATGCCCCTCCC
       ::::::::::::::::::::::::::::::::::::::::::::::::::::::::::::
Licuw, AGAATAAAACAAATTATAAACATGTGGCAGGAAGTAGGAAAAGCAATGTATGCCCCTCCC
        7470      7480      7490      7500      7510      7520

7380      7390      7400      7410      7420      7430
BH 8   ATCAGTGGACAAATTAGATGTTCATCAAATATTACAGGGCTGCTATTAACAAGAGATGGT
       ::  : :::::::::::: ::::::::::::::::::::::::::::::::::::::::
Licuw, ATTGGAGGACAAATTAGTTGTTCATCAAATATTACAGGGCTGCTATTAACAAGAGATGGT
        7530      7540      7550      7560      7570      7580

7440      7450      7460      7470      7480      7490
BH 8   GGTAATA--GCAAC-AATGAGTCCGAGATCTTCAGACCTGGAGGAGGAGATATGAGGGAC
       ::::  :  : :::  ::::: :::::  :::::::::::::::::::::::::::::::
Licuw, GGTACAAATGTAACTAATGACACCGAGGTCTTCAGACCTGGAGGAGGAGATATGAGGGAC
        7590      7600      7610      7620      7630      7640

7500      7510      7520      7530      7540      7550
BH 8   AATTGGAGAAGTGAATTATATAAATATAAAGTAGTAAAAATTGAACCATTAGGAGTAGCA
       :::::::::::::::::::::::::::::::::::: ::::::::::::::::: :::::
Licuw, AATTGGAGAAGTGAATTATATAAATATAAAGTAATAAAAATTGAACCATTAGGAATAGCA
        7650      7660      7670      7680      7690      7700

7560      7570      7580      7590      7600      7610
BH 8    CCCACCAAGGCAAAGAGAAGAGTGGTGCAGAGAGAAAAAAGAGCAGTGGGAATAG---GA
       :::::::::::::::::::::::::::::::::::::::::::::::::::::::   ::
Licuw, CCCACCAAGGCAAAGAGAAGAGTGGTGCAGAGAGAAAAAAGAGCAGTGGGAATAGTAGGA
        7710      7720      7730      7740      7750      7760

7620      7630      7640      7650      7660      7670
BH 8   GCTTTGTTCCTTGGGTTCTTGGGAGCAGCAGGAAGCACTATGGGCGCAGCGTCAATGACG
       :::  :::::::::::::::::::::::::::::::::::::::::  ::::  :::::
Licuw, GCTATGTTCCTTGGGTTCTTGGGAGCAGCAGGAAGCACTATGGGGCGCAGTGTCATTGACG
        7770      7780      7790      7800      7810      7820

7680      7690      7700      7710      7720      7730
BH 8   CTGACGGTACAGGCCAGACAATTATTGTCTGGTATAGTGCAGCAGCAGAACAATTTGCTG
       :::::::::::::::::::::::::::::::::::::::::: ::::::::::::::::
Licuw, CTGACGGTACAGGCCAGACAATTATTGTCTGGTATAGTGCAACAGCAGAACAATTTGCTG
        7830      7840      7850      7860      7870      7880

7740      7750      7760      7770      7780      7790
BH 8   AGGGCTATTGAGGGCCAACAGCATCTGTTGCAACTCACAGTCTGGGGCATCA-GCAGCTC
       ::::::::::::: ::::::::::::::::::::::::::::::::::::   :::::::
Licuw, AGGGCTATTGAGGCGCAACAACATCTGTTGCAACTCACAGTCTGGGGCATCAAGCAGCTC
        7890      7900      7910      7920      7930      7940

7800      7810      7820      7830      7840      7850
BH 8   CAGGCAAGAATCCTGGCTGTGGAAAGATACCTAAAGGATCAACAGCTCCTGGGGATTTGG
       :::::::: :::::::::::::::::::::::::: :::::::::::::::  ::::::
Licuw, CAGGCAAGAGTCCTGGCTGTGGAAAGATACCTAAAGGGATCAACAGCTCCTA--GATTTGG
        7950      7960      7970      7980      7990      8000

7860      7870      7880      7890      7900      7910
BH 8   GGTTGCTCTGGAAAACTCATTTGCACCACTGCTGTGCCTTGGAATGCTAGTTGGAGTAAT
       :::  :::::::::  :::::::::::::::::::::::::::::::::::::::::::
Licuw, GGT-GCTCTGGAAA-CTCATTTGCACCACTGCTGTGCCTTGGAATGCTAGTTGGAGTAAT
         8010      8020      8030      8040      8050      8060

7920      7930      7940      7950      7960      7970
BH 8   AAATCTCTGGAACAGATTTGGAATAACATGACCTGGATGGAGTGGGACAGAGAAATTAAC
       :::::::::::: : ::::::::::::::::::::: ::: ::::::::::::::::::: ::
Licuw, AAATCTCTGGAAGACATTTGGGATAACATGACCTG-ATGCAGTGGGAAGAGAAATTGAC
         8070      8080      8090      8100      8110      8120

7980      7990      8000      8010      8020      8030
BH 8   AATTACACAAGCTTAATACACTCCTTAATTGAAGAATCGCAAAACCAGCAAGAAAAGAAT
       ::::::::::   : ::::  :: ::::::: :::::::::::::   ::::::::::::
Licuw, AATTACACAAACACAATATACACCTTACTTGAAGAATCGCAGAACCAACAAGAAAAGAAT
         8130      8140      8150      8160      8170      8180

8040      8050      8060      8070      8080      8090
BH 8   GAACAAGAATTATTGGAATTAGATAAATGGGCAAGTTTGTGGAATTGGTTTAACATAACA
       ::::::::::::::: :::::::::::  ::::::::::::::::::::::::: :::::::
Licuw, GAACAAGAATTATTAGAATTGGATAAGTGGGCAAGTTTGTGGAATTGGTTTAGCATAACA
         8190      8200      8210      8220      8230      8240
```

TABLE II-continued (BH 5 and 8 v. LUCIW)
89.8% identity

```
              8100      8110      8120      8130      8140      8150
BH 8    AATTGGCTGTGGTATATAAAATTATTCATAATGATAGTAGGAGGCTTGGTAGGTTTAAGA
        ::  ::::::::::::::::::  ::::::::::::::::::::::::::::::::::::
Licuw,  AACTGGCTGTGGTATATAAAGATATTCATAATGATAGTAGGAGGCTTGGTAGGTTTAAGA
              8250      8260      8270      8280      8290      8300

8160      8170      8180      8190      8200      8210
BH 8    ATAGTTTTTGCTGTACTTTCTATAGTGAATAGAGTTAGGCAGGGATATTCACCATTATCG
        :::::::::::::::: :::::::::::::::::::::::::::::: ::::::: ::
Licuw,  ATAGTTTTTGCTGTGCTTTCTATAGTGAATAGAGTTAGGCAGGGATACTCACCATTGTCA
              8310      8320      8330      8340      8350      8360

8220      8230      8240      8250      8260      8270
BH 8    TTTCAGACCCACCTCCCAAACCCGAGGGGACCCGACAGGCCCGAAGGAATAGAAGAAGAA
        :::::::::: ::  :::::   :::::::   :::::::: :::::::: ::::::::
Licuw,  TTTCAGACCCGGCTCCCAGTGCCGAG---ACCCGACAG-CCCGACGGAATCGAAGAAGAA
              8370      8380      8390      8400      8410

8280      8290      8300      8310      8320      8330
BH 8    GGTGGAGAGAGAGACAGAGACAGATCCATTCGATTAGTGAACGGATCCTTAGCACTTATC
        :: :::::::::::::::::::::::::::: ::::::::::: ::::  :::::::::
Licuw,  GG-GGAGAGAGAGACAGAGACAGATCCGTTCGATTAGTGGATGGATTCTTAGCACTTATC
        8420      8430      8440      8450      8460      8470

8340      8350      8360      8370      8380      8390
BH 8    TGGGACGATCTGCGGAGCCTGTGCCTCTTCAGCTACCACCGCTTGAGAGACTTACTCTTG
        ::::: :::::::::::::::::::::::::::::::::  :: ::::::::::::::::
Licuw,  TGGGAAGATCTGCGGAGCCTGTGCCTCTTCAGCTACCGGCGGTTGAGAGACTTACTCTTG
        8480      8490      8500      8510      8520      8530

8400      8410      8420      8430      8440      8450
BH 8    ATTGTAACGAGGATTGTGGAACTTCTGGGACGCAGGGGGTGGGAAGCCCTCAAATATTGG
        :::: : ::::: :::::::: :::::::  :::::::::::::::   :::::::::::
Licuw,  ATTGCAGCGAGGACTGTGGAAATTCTGGGGCACAGGGGGTGGGAA---CTCAAATATTGG
        8540      8550      8560      8570      8580      8590

8460      8470      8480      8490      8500      8510
BH 8    TGGAATCTCCTACAGTATTGGAGTCAGGAACTAAAGAATAGTGCTGTTAACTTGCTCAAT
        :::: :::::: :::::::::: ::::::::::::::::::::::::::: :: ::::::
Licuw,  TGGAGTCTCCTGCAGTATTGGATTCAGGAACTAAAGAATAGTGCTGTTAGCTGGCTCAAC
        8600      8610      8620      8630      8640      8650

8520      8530      8540      8550      8560      8570
BH 8    GCCACAGCCATAGCAGTAGCTGAGGGGACAGATAGGGTTATAGAAGTATTACAAGCAGCT
        ::::::::: ::::::::: :::::::::::::::::::::::::::  :::: ::::::
Licuw,  GCCACAGCTATAGCAGTAACTGAGGGGACAGATAGGGTTATAGAAGTAGCACAAAGAGCT
        8660      8670      8680      8690      8700      8710

8580      8590      8600      8610      8620      8630
BH 8    TATAGAGCCATTCGCCACATACCTAGAAGAATAAGACAGGGCTTGGAAAGGATTTTGCTA
        :::::::: :::: :::::::::: :::::::: :::::   ::::::::::::::::::
Licuw,  TATAGAGCTATTCTCCACATACATAGAAGAATTAGACA---CTTGGAAAGGCTTTTGCTA
        8720      8730      8740      8750      8760      8770

8640      8650      8660      8670      8680      8690
BH 8    TAAGATGGGTGGCAAGTGGTCAAAAAGTAGTGTGGTTGGATGGCCTGCTGTAAGGGAAAG
        :::::::::::   :::::::::: : :::::::::   ::::::  ::: ::::::::
Licuw,  TAAGATGGGGG---AGTGGTCAAAACG-AGTATGGG-GGATGGTCTGCTATAAGGGAAAG
              8780      8790      8800      8810      8820

8700      8710      8720      8730
BH 8    AATGAGACGAGCTGAGCCA-----------GCAGCAGATGGGTGGGAGCAGTATCTCG
        :::::::::::::::::::           :::::::::: ::::  :::::::::::
Licuw,  AATGAGACGAGCTGAGCCACGAGCTGAGCCAGCAGCAGATGGG-TGGGA-CAGTATCTCG
              8830      8840      8850      8860      8870      8880

8740      8750      8760      8770      8780      8790
BH 8    AGACCTAGAAAAACATGGAGCAATCACAAGTAGCAATACAGCAGCTACCAATGCTGATTG
        ::::: ::::::::::::::  :::::::::::::::::::::::::: :::::::::::
Licuw,  AGACCTGGAAAAACATGGA--AATCACAAGTAGCAATACAGCAGCTACTAATGCTGATTG
              8890      8900      8910      8920      8930      8940
```

TABLE II-continued (BH 5 and 8 v. LUCIW)
89.8% identity

```
          8800      8810      8820      8830      8840      8850
BH 8    TGCTTGGCTAGAAGCACAAGAGGAGGAGGAGGTGGGTTTTCCAGTCACACCTCAGGTACC
        ::::  :::::::::::::::::::::::::  ::::::::::::::::  ::::::::::::
Licuw,  TGCCTGGCTAGAAGCACAAGAGGAGGAAGAGGTGGGTTTTCCAGTCAGACCTCAGGTACC
          8950      8960      8970      8980      8990      9000

8860      8870      8880      8890      8900      8910
BH 8    TTTAAGACCAATGACTTACAAGGCAGCTGTAGATCTTAGCCACTTTTTAAAAGAAAAGGG
        :::::::::::::::::::::::::::::::  :::::  :::::::::::::::::::::::
Licuw,  TTTAAGACCAATGACTTACAAGGCAGCTTTAGATATTAGCCACTTTTTAAAAGAAAAGGG
          9010      9020      9030      9040      9050      9060

8920      8930      8940      8950      8960      8970
BH 8    GGGACTGGAAGGGCTAATTCACTCCCAACGAAGACAAGATATCCTTGATCTGTGGATCCA
        :::::::::::::::::::  :::::::  ::::::::::  :::::::::::::::::::: :
Licuw,  GGGACTGGAAGGGCTAATTTGGTCCCAAAGAAGACAAGAGATCCTTGATCTGTGGATCTA
          9070      9080      9090      9100      9110      9120

8980      8990      9000      9010      9020      9030
BH 8    CCACACACAAGGCTACTTCCCTGATTGGCAGAACTACACACCAGGGCCAGGGATCAGATA
        ::::::::::::::::::::::::::::::::::::::  :::::::::::::::::::::::::
Licuw,  CCACACACAAGGCTACTTCCCTGATTGGCAGAATTACACACCAGGGCCAGGGATCAGATA
          9130      9140      9150      9160      9170      9180

9040      9050      9060      9070      9080      9090
BH 8    TCCACTGACCTTTGGATGGTGCTACAAGCTAGTACCAGTTGAGCCAGAGAAGATAGAAGA
        :::::::::::::::::::::::::  ::::::::::::::::::::::::::::::  ::::::
Licuw,  TCCACTGACCTTTGGATGGTGCTTCAAGCTAGTACCAGTTGAGCCAGAGAAGGTAGAAGA
          9190      9200      9210      9220      9230      9240

9100      9110      9120      9130      9140      9150
BH 8    AGCCAATAAAGGAGAGAACACCAGCTTGTTACACCCTGTGAGCCTGCATGGGATGGATGA
        ::::::  ::::::::::::::::  :::::::::::::::  ::::::::::::::::::: ::
Licuw,  GGCCAATGAAGGAGAGAACAA-AGCTTGTTACACCCTATGAGCCTGCATGGGATGGAGGA
          9250      9260      9270      9280      9290      9300

9160      9170      9180      9190      9200      9210
BH 8    CCCTGAGAGAGAAGTGTTAGAGTGGAGGTTTGACAGCCGCCTAGCATTTCATCACATGGC
        :  :  ::::  :::::::::::::::  :::::::::::::::  ::::::::::::::::::::
Licuw,  CGCGGAGAAAGAAGTGTTAGTGTGGAGGTTTGACAGCAAACTAGCATTTCATCACATGGC
          9310      9320      9330      9340      9350      9360

9220      9230      9240      9250      9260      9270
BH 8    CCGAGAGCTGCATCCGGAGTACTTCAAGAACTGCTGACATCGAGCTTGCTACAAGGGACT
        ::::::::::::::::::::::::::  :::  ::::::::::::::::::::::  ::::::::::
Licuw,  CCGAGAGCTGCATCCGGAGTACTACAAAGACTGCTGACATCGAGCTTTCTACAAGGGACT
          9370      9380      9390      9400      9410      9420

9280      9290      9300      9310      9320      9330
BH 8    TTCCGCTGGGGACTTT--------GCGTGGCCTGGGCGGGACTGGGGAGTGGCGAGCCCT
        ::::::::::::::::::        :::::::::::::::::::::::::::::::  ::::
Licuw,  TTCCGCTGGGGACTTTTCCAGGGAGGCGTGGCCTGGGCGGGACTGGGGAGTGGCGT-CCCT
          9430      9440      9450      9460      9470

9340      9350      9360      9370      9380
BH 8    CAGATCCTGCATATAA--------TTTTTGCCTGTACTGGGTCTCTCTGGTTAGACCAGA
        ::::::  :::::::::           :::::::::::::::::::::::::::::::::::
Licuw,  CAGATGCTGCATATAAGCAGCTGCTTTTTGCCTGTACTGGGTCTCTCTGGTTAGACCAGA
          9480      9490      9500      9510      9520      9530

9390
BH 8    TCTGAGCCTGGGAGCTC-------------------------------------------
        :::::::::::::::::
Licuw,  TCTGAGCCTGGGAGCTCTCTGGCTAACTAGGGAACCCACTGCTTAAGCCTCAATAAAGCT
          9540      9550      9560      9570      9580      9590

------------------------------------------------------------
Licuw,  TGCCTTGAGTGCTTCAAGTAGTGTGTGCCCGTCTGTTGTGTGACTCTGGTAACTAGAGAT
          9600      9610      9620      9630      9640      9650

----------------------------------------
Licuw,  CCCTCAGACCCTTTTAGTCAGTGTGGAAAAATCTCTAGCAG
          9660      9670      9680      9690      9700
```

TABLE III (BH 10 v. LUCIW)
90.0% identity

```
              10        20        30        40        50
BH 10   -TGGAAGGGCTAATTCACTCCCAACGAAGACAAGATATCCTTGATCTGTGGATCTACCAC
         ::::::::::::::    ::::::  ::::::::::  ::::::::::::::::::::::::::
Licuw,  CTGGAAGGGCTAATTTGGTCCCAAAGAAGACAAGAGATCCTTGATCTGTGGATCTACCAC
              10        20        30        40        50        60

60        70        80        90       100       110
BH 10   ACACAAGGCTACTTCCCTGATTAGCAGAACTACACACCAGGGCCAGGGATCAGATATCCA
        ::::::::::::::::::::::::::::  :::::: :::::::::::::::::::::::::::::
Licuw,  ACACAAGGCTACTTCCCTGATTGGCAGAATTACACACCAGGGCCAGGGATCAGATATCCA
              70        80        90       100       110       120

120       130       140       150       160       170
BH 10   CTGACCTTTGGATGGTGCTACAAGCTAGTACCAGTTGAGCCAGAGAAGTTAGAAGAAGCC
        :::::::::::::::::::  ::::::::::::::::::::::::::::::  :::::::  :::
Licuw,  CTGACCTTTGGATGGTGCTTCAAGCTAGTACCAGTTGAGCCAGAGAAGGTAGAAGAGGCC
             130       140       150       160       170       180

180       190       200       210       220       230
BH 10   AACAAAGGAGAGAACACCAGCTTGTTACACCCTGTGAGCCTGCATGGAATGGATGACCCG
         ::   ::::::::::::::  ::::::::::::::::::::::::::::::::  :::  ::  ::
Licuw,  AATGAAGGAGAGAACAACAGCTTGTTACACCCTATGAGCCTGCATGGGATGGAGGACGCG
             190       200       210       220       230       240

240       250       260       270       280       290
BH 10   GAGAGAGAAGTGTTAGAGTGGAGGTTTGACAGCCGCCTAGCATTTCATCACATGGCCCGA
        ::::  :::::::::::::::  :::::::::::::::::  :::::::::::::::::::::::::
Licuw,  GAGAAAGAAGTGTTAGTGTGGAGGTTTGACAGCAAACTAGCATTTCATCACATGGCCCGA
             250       260       270       280       290       300

300       310       320       330       340       350
BH 10   GAGCTGCATCCGGAGTACTTCAAGAACTGCTGACATCGAGCTTGCTACAAGGGACTTTCC
        :::::::::::::::::::::::  ::::  ::::::::::::::::::::  ::::::::::::::::
Licuw,  GAGCTGCATCCGGAGTACTACAAAGACTGCTGACATCGAGCTTTCTACAAGGGACTTTCC
             310       320       330       340       350       360

360       370       380       390       400       410
BH 10   GCTGGGGACTTTCCAGGGAGGCGTGGCCTGGGCGGGACTGGGGAGTGGCGAGCCCTCAGA
        ::::::::::::::::::::::::::::::::::::::::::::::::::::::::::  :::::::
Licuw,  GCTGGGGACTTTCCAGGGAGGCGTGGCCTGGGCGGGACTGGGGAGTGGCGT-CCCTCAGA
             370       380       390       400       410

420       430       440       450       460       470
BH 10   TCCTGCATATAAGCAG-CTGCTTTTTGCCTGTACTGGGTCTCTCTGGTTAGACCAGATCT
         :  :::::::::::::: :::::::::::::::::::::::::::::::::::::::::::::::
Licuw,  TGCTGCATATAAGCAGACTGCTTTTTGCCTGTACTGGGTCTCTCTGGTTAGACCAGATCT
             420       430       440       450       460       470

480       490
BH 10   GAGCCTGGGAGCTC-------------------------------------------
        ::::::::::::::
Licuw,  GAGCCTGGGAGCTCTCTGGCTAACTAGGGAACCCACTGCTTAAGCCTCAATAAAGCTTGC
             480       490       500       510       520       530

Licuw,  CTTGAGTGCTTCAAGTAGTGTGTGCCCGTCTGTTGTGTGACTCTGGTAACTAGAGATCCC
             540       550       560       570       580       590

Licuw,  TCAGACCCTTTTAGTCAGTGTGGAAAAATCTCTAGCAGTGGCGCCCGAACAGGGACGCGA
             600       610       620       630       640       650

500       510       520       530
BH 10   --------------------GAGCTCTCTCGACGCAGGACTCGGCTTGCTGAAGCGCGCA
                             ::::::::::::::::::::::::::::::::::::::::::::::
Licuw,  AAGCGAAAGTAGAACCAGAGGAGCTCTCTCGACGCAGGACTCGGCTTGCTGAAGCGCGCA
             660       670       680       690       700       710

540       550       560       570       580       590
BH 10   CGGCAAGAGGCGAGGGGCGGCGACTGGTGAGTACGCCAAAAATTTTGACTAGCGGAGGCT
        :  :::::::::::::::::::::::::::::::::::::::::::  ::::::::::::::::::
Licuw,  CAGCAAGAGGCGAGGGGCGGCGACTGGTGAGTACGCCAA--TTTTTGACTAGCGGAGGCT
             720       730       740       750       760       770
```

TABLE III-continued (BH 10 v. LUCIW)
90.0% identity

```
              600       610       620       630       640       650
BH 10   AGAAGGAGAGAGA--TGGGTGCGAGAGCGTCAGTATTAAGCGGGGGAGAATTAGATCGAT
        ::::::::::::    ::::::::::::::::: :::::::::::::::::::::  ::
Licuw,  AGAAGGAGAGAGAGATGGGTGCGAGAGCGTCGGTATTAAGCGGGGGAGAATTAGATAAAT
              780       790       800       810       820       830

660       670       680       690       700       710
BH 10   GGGAAAAAATTCGGTTAAGGCCAGGGGGAAAGAAAAAATATAAATTAAAACATATAGTAT
        :::::::::::::::::::::::::::::::::::::::::::: :::::::::::::::
Licuw,  GGGAAAAAATTCGGTTAAGGCCAGGGGGAAAGAAAAAATATAAGTTAAAACATATAGTAT
              840       850       860       870       880       890

720       730       740       750       760       770
BH 10   GGGCAAGCAGGGAGCTAGAACGATTCGCAGTTAATCCTGGCCTGTTAGAAACATCAGAAG
        ::::::::::::::::::::::::::::::::: ::::::::::::::::::::::::::
Licuw,  GGGCAAGCAGGGAGCTAGAACGATTCGCAGTCAATCCTGGCCTGTTAGAAACATCAGAAG
              900       910       920       930       940       950

780       790       800       810       820       830
BH 10   GCTGTAGACAAATACTGGGACAGCTACAACCATCCCTTCAGACAGGATCAGAAGAACTTA
        :::: ::::::::::: :::::::::  ::: ::::::::::::::::::::::::::::
Licuw,  GCTGCAGACAAATATTGGGACAGCTACAGCCATCCCTTCAGACAGGATCAGAAGAACTTA
              960       970       980       990      1000      1010

840       850       860       870       880       890
BH 10   GATCATTATATAATACAGTAGCAACCCTCTATTGTGTGCATCAAAGGATAGAGATAAAAG
        ::::::::::::::::::::::::::::::::::::: ::: ::::::::::: ::::::
Licuw,  GATCATTATATAATACAGTAGCAACCCTCTATTGTGTACATCAAAGGATAGATGTAAAAG
             1020      1030      1040      1050      1060      1070

900       910       920       930       940       950
BH 10   ACACCAAGGAAGCTTTAGACAAGATAGAGGAAGAGCAAAACAAAAGTAAGAAAAAAGCAC
        :::::::::::::::::::: ::::::::::::::::::::::::::::::::::: :::
Licuw,  ACACCAAGGAAGCTTTAGAGAAGATAGAGGAAGAGCAAAACAAAAGTAAGAAAAAGGCAC
             1080      1090      1100      1110      1120      1130

960              970       980       990      1000
BH 10   AGCAAGCAGCAGCTGA------CACAGGACACAGCAGTCAGGTCAGCCAAAATTACCCTA
        :::::::::::::::       :::::: :::::: ::::::::::::::::::::::::
Licuw,  AGCAAGCAGCAGCTGCAGCTGGCACAGGAAACAGCAGCCAGGTCAGCCAAAATTACCCTA
             1140      1150      1160      1170      1180      1190

1010      1020      1030      1040      1050      1060
BH 10   TAGTGCAGAACATCCAGGGGCAAATGGTACATCAGGCCATATCACCTAGAACTTTAAATG
        :::::::::::: : :::::::::::::::::::::::::::::::::::::::::::::
Licuw,  TAGTGCAGAACCTACAGGGGCAAATGGTACATCAGGCCATATCACCTAGAACTTTAAATG
             1200      1210      1220      1230      1240      1250

1070      1080      1090      1100      1110      1120
BH 10   CATGGGTAAAAGTAGTAGAAGAGAAGGCTTTCAGCCCAGAAGTAATACCCATGTTTTCAG
        :::::::::::::::::::::::: ::::::::::::::::::::::::::::::::::
Licuw,  CATGGGTAAAAGTAGTAGAAGAAAAGGCTTTCAGCCCAGAAGTAATACCCATGTTTTCAG
             1260      1270      1280      1290      1300      1310

1130      1140      1150      1160      1170      1180
BH 10   CATTATCAGAAGGAGCCACCCCACAAGATTTAAACACCATGCTAAACACAGTGGGGGGAC
        ::::::::::::::::::::::::::::::::::::::::::::::::::::::::::::
Licuw,  CATTATCAGAAGGAGCCACCCCACAAGATTTAAACACCATGCTAAACACAGTGGGGGGAC
             1320      1330      1340      1350      1360      1370

1190      1200      1210      1220      1230      1240
BH 10   ATCAAGCAGCCATGCAAATGTTAAAAGAGACCATCAATGAGGAAGCTGCAGAATGGGATA
        ::::::::::::::::::::::::::::::::: ::::::::::::::::::::::::::
Licuw,  ATCAAGCAGCCATGCAAATGTTAAAAGAGACTATCAATGAGGAAGCTGCAGAATGGGATA
             1380      1390      1400      1410      1420      1430

1250      1260      1270      1280      1290      1300
BH 10   GAGTACATCCAGTGCATGCAGGGCCTATTGCACCAGGCCAGATGAGAGAACCAAGGGGAA
        :::: :::::::::::::::::::::::::::::::::::: ::::::::::::::::::
Licuw,  GAGTGCATCCAGTGCATGCAGGGCCTATTGCACCAGGCCAAATGAGAGAACCAAGGGGAA
             1440      1450      1460      1470      1480      1490

1310      1320      1330      1340      1350      1360
BH 10   GTGACATAGCAGGAACTACTAGTACCCTTCAGGAACAAATAGGATGGATGACAAATAATC
        ::::::::::::::::::::::::::::::::::::::::::::::::::::::::::::
Licuw,  GTGACATAGCAGGAACTACTAGTACCCTTCAGGAACAAATAGGATGGATGACAAATAATC
             1500      1510      1520      1530      1540      1550
```

TABLE III-continued (BH 10 v. LUCIW)
90.0% identity

```
              1370      1380      1390      1400      1410      1420
BH 10   CACCTATCCCAGTAGGAGAAATTTATAAAAGATGGATAATCCTGGGATTAAATAAAATAG
        ::::::::::::::::::::::::::::::: ::::::::::::::::::::::::::::
Licuw,  CACCTATCCCAGTAGGAGAAATCTATAAAAGATGGATAATCCTGGGATTAAATAAAATAG
              1560      1570      1580      1590      1600      1610

1430      1440      1450      1460      1470      1480
BH 10   TAAGAATGTATAGCCCTACCAGCATTCTGGACATAAGACAAGGACCAAAAGAACCTTTTA
        :::::::::::::::::::::::::::::::::::::::::::::: ::::: :::::::
Licuw,  TAAGAATGTATAGCCCTACCAGCATTCTGGACATAAGACAAGGACCAAAGGAACCCTTTA
              1620      1630      1640      1650      1660      1670

1490      1500      1510      1520      1530      1540
BH 10   GAGACTATGTAGACCGGTTCTATAAAACTCTAAGAGCCGAGCAAGCTTCACAGGAGGTAA
        :::: :::::::::::::::::::::::::::::::::::: ::::::::::::: :::
Licuw,  GAGATTATGTAGACCGGTTCTATAAAACTCTAAGAGCCGAACAAGCTTCACAGGATGTAA
              1680      1690      1700      1710      1720      1730

1550      1560      1570      1580      1590      1600
BH 10   AAAATTGGATGACAGAAACCTTGTTGGTCCAAAATGCGAACCCAGATTGTAAGACTATTT
        :::::::::::::::::::::::::::::::::::::::: :::::::::::::::::::
Licuw,  AAAATTGGATGACAGAAACCTTGTTGGTCCAAAATGCAAACCCAGATTGTAAGACTATTT
              1740      1750      1760      1770      1780      1790

1610      1620      1630      1640      1650      1660
BH 10   TAAAAGCATTGGGACCAGCGGCTACACTAGAAGAAATGATGACAGCATGTCAGGGAGTAG
        :::::::::::::::::::::: :::::::::::::::::::::::::::::::::::: :
Licuw,  TAAAAGCATTGGGACCAGCAGCTACACTAGAAGAAATGATGACAGCATGTCAGGGAGTGG
              1800      1810      1820      1830      1840      1850

1670      1680      1690      1700      1710      1720
BH 10   GAGGACCCGGCCATAAGGCAAGAGTTTTGGCTGAAGCAATGAGCCAAGTAACAAATACAG
        : :::::::::::::: :::::::::::::::::::: :::::::::::::::: :::
Licuw,  GGGGACCCGGCCATAAAGCAAGAGTTTTGGCTGAAGCCATGAGCCAAGTAACAAATCCAG
              1860      1870      1880      1890      1900      1910

1730      1740      1750      1760      1770      1780
BH 10   CTACCATAATGATGCAGAGAGGCAATTTTAGGAACCAAAGAAAGATGGTTAAGTGTTTCA
        ::: ::::::::::::::::::::::::::::::::::::::::::: :::::::::::
Licuw,  CTAACATAATGATGCAGAGAGGCAATTTTAGGAACCAAAGAAAGACTGTTAAGTGTTTCA
              1920      1930      1940      1950      1960      1970

1790      1800      1810      1820      1830      1840
BH 10   ATTGTGGCAAAGAAGGGCACACAGCCAGAAATTGCAGGGCCCCTAGGAAAAAGGGCTGTT
        :::::::::::::::: :::: ::::: :::::::::::::::::::::::::::   ::
Licuw,  ATTGTGGCAAAGAAGG-CACATAGCCAAAAATTGCAGGGCCCCTAGGAAAAAGGG---TT
              1980      1990      2000      2010      2020      2030

1850      1860      1870      1880      1890      1900
BH 10   GGAAATGTGGAAAGGAAGGACACCAAATGAAAGATTGTACTGAGAGACAGGCTAATTTTT
        :: : :::::::::::::::::::::::::::::::::::: ::::::::::::::::::
Licuw,  TGGAGTGTGGAAGGGAAGGACACCAAATGAAAGATTGCACTGAGAGACAGGCTAATTTTT
              2040      2050      2060      2070      2080      2090

1910      1920      1930      1940      1950      1960
BH 10   TAGGGAAGATCTGGCCTTCCTACAAGGGAAGGCCAGGGAATTTTCTTCAGAGCAGACCAG
        ::::::::::::::::::::::::::::::::::::::::::::::
Licuw,  TAGGGAAGATCTGGCCTTCCTACAAGGGAAGGCCAGGGAATTTTCT--------------
              2100      2110      2120      2130

1970      1980      1990      2000      2010      2020
BH 10   AGCCAACAGCCCCACCATTTCTTCAGAGCAGACCAGAGCCAACAGCCCCACCAGAAGAGA
                              ::::::::::::::::::::::::::::::::::::::
Licuw,  ---------------------TCAGAGCAGACCAGAGCCAACAGCCCCACCAGAAGAGA
                                  2140      2150      2160      2170

2030      2040      2050      2060      2070      2080
BH 10   GCTTCAGGTCTGGGGTAGAGACAACAACTCCCCCTCAGAAGCAGGAGCCGATAGACAAGG
        :::::::::: ::::: :::: :::::::::::: :::::::::::::::::::::::::
Licuw,  GCTTCAGGTTTGGGGAGGAGAAAACAACTCCCTCTCAGAAGCAGGAGCCGATAGACAAGG
              2180      2190      2200      2210      2220      2230
```

TABLE III-continued (BH 10 v. LUCIW)
90.0% identity

```
              2090      2100      2110      2120      2130      2140
BH 10   AACTGTATCCTTTAACTTCCCTCAGATCACTCTTTGGCAACGACCCCTCGTCACAATAAA
        ::::::::::::::::::::::::::::::::::::::::::::::::::::::::::  ::
Licuw,  AACTGTATCCTTTAACTTCCCTCAGATCACTCTTTGGCAACGACCCCTCGTCACAATTAA
              2240      2250      2260      2270      2280      2290

2150      2160      2170      2180      2190      2200
BH 10   G-ATAGGGGGCAACTAAAGGAAGCTCTATTAGATACAGGAGCAGATGATACAGTATTAG
        :  :::::::::::::::::::::::::::::::::::::::::::::::::::::::::
Licuw,  GGATAGGGGGCAACTAAAGGAAGCTCTATTAGATACAGGAGCAGATGATACAGTATTAG
              2300      2310      2320      2330      2340      2350

2210      2220      2230      2240      2250      2260
BH 10   AAGAAATGAGTTTGCCAGGAAGATGGAAACCAAAAATGATAGGGGGAATTGGAGGTTTTA
        :::::::::: :::::::::::::: :::::::::::::::::::::::::::::::::
Licuw,  AAGAAATGAATTTGCCAGGAAAATGGAAACCAAAAATGATAGGGGGAATTGGAGGTTTTA
              2360      2370      2380      2390      2400      2410

2270      2280      2290      2300      2310      2320
BH 10   TCAAAGTAAGACAGTATGATCAGATACTCATAGAAATCTGTGGACATAAAGCTATAGGTA
        :::::::::::::::: :::::::::: ::::::::::::::::::::::::::::::::
Licuw,  TCAAAGTAAGACAGTACGATCAGATACCTGTAGAAATCTGTGGACATAAAGCTATAGGTA
              2420      2430      2440      2450      2460      2470

2330      2340      2350      2360      2370      2380
BH 10   CAGTATTAGTAGGACCTACACCTGTCAACATAATTGGAAGAAATCTGTTGACTCAGATTG
        ::::::::::::::::::::::::::::::::::::::::::::::::::::::::::::
Licuw,  CAGTATTAGTAGGACCTACACCTGTCAACATAATTGGAAGAAATCTGTTGACTCAGATTG
              2480      2490      2500      2510      2520      2530

2390      2400      2410      2420      2430      2440
BH 10   GTTGCACTTTAAATTTTCCCATTAGCCCTATTGAGACTGTACCAGTAAAATTAAAGCCAG
        :::: :::::::::::: :::::::: ::::::: ::::::::::::::::::::::::
Licuw,  GTTGTACTTTAAATTTCCCCATTAGTCCTATTGAAACTGTACCAGTAAAATTAAAGCCAG
              2540      2550      2560      2570      2580      2590

2450      2460      2470      2480      2490      2500
BH 10   GAATGGATGCCCAAAAGTTAAACAATGGCCATTGACAGAAGAAAAAATAAAAGCATTAG
        :::::::::::::::::::::: ::::::::::::::::::::::::::::::::::::
Licuw,  GAATGGATGCCCAAAAGTTAAGCAATGGCCATTGACAGAAGAAAAAATAAAAGCATTAG
              2600      2610      2620      2630      2640      2650

2510      2520      2530      2540      2550      2560
BH 10   TAGAAATTTGTACAGAAATGGAAAAGGAAGGGAAAATTTCAAAAATTGGGCCTGAGAATC
        :::: :: ::::::::::::::::::::::::::::::::::::::::::::::: ::::
Licuw,  TAGAGATATGTACAGAAATGGAAAAGGAAGGGAAAATTTCAAAAATTGGGCCTGAAAATC
              2660      2670      2680      2690      2700      2710

2570      2580      2590      2600      2610      2620
BH 10   CATACAATACTCCAGTATTTGCCATAAAGAAAAAAGACAGTACTAAATGGAGAAAATTAG
        ::::::::::::::::::::: :::::::::::::::::::::::::::::::::: :::
Licuw,  CATACAATACTCCAGTATTTGCTATAAAGAAAAAAGACAGTACTAAATGGAGAAAACTAG
              2720      2730      2740      2750      2760      2770

2630      2640      2650      2660      2670      2680
BH 10   TAGATTTCAGAGAACTTAATAAGAGAACTCAAGACTTCTGGGAAGTTCAATTAGGAATAC
        :::::::::::::::::::::: :::::::::::::::::::::::::::: ::::::::
Licuw,  TAGATTTCAGAGAACTTAATAAAAGAACTCAAGACTTCTGGGAAGTTCAGTTAGGAATAC
              2780      2790      2800      2810      2820      2830

2690      2700      2710      2720      2730      2740
BH 10   CACATCCCGCAGGGTTAAAAAA-GAAAAAATCAGTAACAGTACTGGATGTGGGTGATGCA
        :::: :::::::::::::::::: :::::::::::::::::::: :::::::::::::::
Licuw,  CACA-CCCGCAGGGTTAAAAAAGAAAAAATCAGTAACAGTATTGGATGTGGGTGATGCA
              2840      2850      2860      2870      2880      2890

2750      2760      2770      2780      2790      2800
BH 10   TATTTTTCAGTTCCCTTAGATGAAGACTTCAGGAAGTATACTGCATTTACCATACCTAGT
        :: ::::::::::::::::::: :::::::: ::::::::::::::::::::::::::::
Licuw,  TACTTTTCAGTTCCCTTAGATAAAGACTTTAGAAAGTATACTGCATTTACCATACCTAGT
              2900      2910      2920      2930      2940      2950

2810      2820      2830      2840      2850      2860
BH 10   ATAAACAATGAGACACCAGGGATTAGATATCAGTACAATGTG-CTTCCACAGGGATGGAA
        :::::::::::::::::::::::::::::::::::::::::: ::: :::::::::::::
Licuw,  ATAAACAATGAGACACCAGGGATTAGATATCAGTACAATGTGGCTGCCACAGGGATGGAA
              2960      2970      2980      2990      3000      3010
```

TABLE III-continued (BH 10 v. LUCIW)
90.0% identity

```
               2870      2880      2890      2900      2910      2920
BH 10    AGGATCACCAGCAATATTCCAAAGTAGCATGACAAAAATCTTAGAGCCTTTTAAAAAACA
         ::::::::::::::::::::::::::::::::::::::::::::::::::::: ::::::
Licuw,   AGGATCACCAGCAATATTCCAAAGTAGCATGACAAAAATCTTAGAGCCTTTTAGAAAACA
               3020      3030      3040      3050      3060      3070

2930      2940      2950      2960      2970      2980
BH 10    AAATCCAGACATAGTTATCTATCAATACATGGATGATTTGTATGTAGGATCTGACTTAGA
          ::::::::::::::::::::::::::::::::::::::::::::::::::::::::::
Licuw,   GAATCCAGACATAGTTATCTATCAATACATGGATGATTTGTATGTAGGATCTGACTTAGA
               3080      3090      3100      3110      3120      3130

2990      3000      3010      3020      3030      3040
BH 10    AATAGGGCAGCATAGAACAAAAATAGAGGAGCTGAGACAACATCTGTTGAGGTGGGGACT
         :::::::::::::::::::::::::::::::: :::::::: ::::::::::::::::: :
Licuw,   AATAGGGCAGCATAGAACAAAAATAGAGGAACTGAGACAGCATCTGTTGAGGTGGGGATT
               3140      3150      3160      3170      3180      3190

3050      3060      3070      3080      3090      3100
BH 10    TACCACACCAGACAAAAAACATCAGAAAGAACCTCCATTCCTTTGGATGGGTTATGAACT
         ::::::::::::::::::::::::::::::::::::::::::::::::::::::::::::
Licuw,   TACCACACCAGACAAAAAACATCAGAAAGAACCTCCATTCCTTTGGATGGGTTATGAACT
               3200      3210      3220      3230      3240      3250

3110      3120      3130      3140      3150      3160
BH 10    CCATCCTGATAAATGGACAGTACAGCCTATAGTGCTGCCAGAAAAAGACAGCTGGACTGT
         :::::::::::::::::::::::::::::::::: :::::::::::::::::::::::::
Licuw,   CCATCCTGATAAATGGACAGTACAGCCTATAATGCTGCCAGAAAAAGACAGCTGGACTGT
               3260      3270      3280      3290      3300      3310

3170      3180      3190      3200      3210      3220
BH 10    CAATGACATACAGAAGTTAGTGGGGAAATTGAATTGGGCAAGTCAGATTTACCCAGGGAT
         :::::::::::::::::::::::::::::: ::::::::::::::::::::: :::::::
Licuw,   CAATGACATACAGAAGTTAGTGGGAAAATTGAATTGGGCAAGTCAGATTTATGCAGGGAT
               3320      3330      3340      3350      3360      3370

3230      3240      3250      3260      3270      3280
BH 10    TAAAGTAAGGCAATTATGTAAACTCCTTAGAGGAACCAAAGCACTAACAGAAGTAATACC
         ::::::: ::: :::::::::::::::::::::::::::::::::::::::::::::::
Licuw,   TAAAGTAAAGCAGTTATGTAAACTCCTTAGAGGAACCAAAGCACTAACAGAAGTAATACC
               3380      3390      3400      3410      3420      3430

3290      3300      3310      3320      3330      3340
BH 10    ACTAACAGAAGAAGCAGAGCTAGAACTGGCAGAAAACAGAGAGATTCTAAAAGAACCAGT
         :::::::::::::::::::::::::::::::::::::::: :::::::::::::::::::
Licuw,   ACTAACAGAAGAAGCAGAGCTAGAACTGGCAGAAAACAGGGAGATTCTAAAAGAACCAGT
               3440      3450      3460      3470      3480      3490

3350      3360      3370      3380      3390      3400
BH 10    ACATGGAGTGTATTATGACCCATCAAAAGACTTAATAGCAGAAATACAGAAGCAGGGGCA
         ::::: ::: ::::::::::::::::::::::: ::::::::::::::::::::::::::
Licuw,   ACATGAAGTATATTATGACCCATCAAAAGACTTAGTAGCAGAAATACAGAAGCAGGGGCA
               3500      3510      3520      3530      3540      3550

3410      3420      3430      3440      3450      3460
BH 10    AGGCCAATGGACATATCAAATTTATCAAGAGCCATTTAAAAATCTGAAAACAGGAAAATA
         ::::::::::::::::::::::::::::::::::::::::::::::::::::::::  ::
Licuw,   AGGCCAATGGACATATCAAATTTATCAAGAGCCATTTAAAAATCTGAAAACAGGAAAGTA
               3560      3570      3580      3590      3600      3610

3470      3480      3490      3500      3510      3520
BH 10    TGCAAGAATGAGGGGTGCCCACACTAATGATGTAAAACAATTAACAGAGGCAGTGCAAAA
         :::::  :::::::::::::::::::::::::::::: ::::::::::::::::::::::
Licuw,   TGCAAGGATGAGGGGTGCCCACACTAATGATGTAAAACAGTTAACAGAGGCAGTGCAAAA
               3620      3630      3640      3650      3660      3670

3530      3540      3550      3560      3570      3580
BH 10    AATAACCACAGAAAGCATAGTAATATGGGAAAGACTCCTAAATTTAAACTACCCATACA
         :  ::::::::::::::::::::::::::::::: ::::::::::::::::::::::::
Licuw,   AGTATCCACAGAAAGCATAGTAATATGGGAAAGATTCCTAAATTTAAACTACCCATACA
               3680      3690      3700      3710      3720      3730
```

TABLE III-continued (BH 10 v. LUCIW)
90.0% identity

```
              3590      3600      3610      3620      3630      3640
BH 10   AAAGGAAACATGGGAAACATGGTGGACAGAGTATTGGCAAGCCACCTGGATTCCTGAGTG
        :::::::::::::::::::  :::::::::  ::::::::::::::::  ::::::::::::::::::
Licuw,  AAAGGAAACATGGGAAGCATGGTGGATGGAGTATTGGCAAGCTACCTGGATTCCTGAGTG
              3740      3750      3760      3770      3780      3790

3650      3660      3670      3680      3690      3700
BH 10   GGAGTTTGTTAATACCCCTCCTTTAGTGAAATTATGGTACCAGTTAGAGAAAGAACCCAT
        ::::::::: :::::::: ::::::::::::::::::::::::::::::::::::::::
Licuw,  GGAGTTTGTCAATACCCCTCCCTTAGTGAAATTATGGTACCAGTTAGAGAAAGAACCCAT
              3800      3810      3820      3830      3840      3850

3710      3720      3730      3740      3750      3760
BH 10   AGTAGGAGCAGAAACCTTCTATGTAGATGGGGCAGCTAACAGGGAGACTAAATTAGGAAA
        :::::::::::::::: :::::::::::::::::::::::: :: :::::::::::::::
Licuw,  AGTAGGAGCAGAAACTTTCTATGTAGATGGGGCAGCTAATAGGGAGACTAAATTAGGAAA
              3860      3870      3880      3890      3900      3910

3770      3780      3790      3800      3810      3820
BH 10   AGCAGGATATGTTACTAACAAAGGAAGACAAAAGGTTGTCCCCCTAACTAACACAACAAA
        ::::::::::::::::: ::: ::::::::::::::: :::::  :: :: :: ::::::::::
Licuw,  AGCAGGATATGTTACTGACAGAGGAAGACAAAAAGTTGTCTCCATAGCTGACACAACAAA
              3920      3930      3940      3950      3960      3970

3830      3840      3850      3860      3870      3880
BH 10   TCAGAAAACTGAGTTACAAGCAATTTATCTAGCTTTGCAGGATTCAGGATTAGAAGTAAA
        :::::: ::::: ::::::::::::::: ::::::::::::::::: :::::::::::::::
Licuw,  TCAGAAGACTGAATTACAAGCAATTCATCTAGCTTTGCAGGATTCGGGATTAGAAGTAAA
              3980      3990      4000      4010      4020      4030

3890      3900      3910      3920      3930      3940
BH 10   CATAGTAACAGACTCACAATATGCATTAGGAATCATTCAAGCACAACCAGATAAAAGTGA
        ::::::::::::::::::::::::::::::::::::::::::::::::::::::::: :::::
Licuw,  CATAGTAACAGACTCACAATATGCATTAGGAATCATTCAAGCACAACCAGATAAGAGTGA
              4040      4050      4060      4070      4080      4090

3950      3960      3970      3980      3990      4000
BH 10   ATCAGAGTTAGTCAATCAAATAATAGAGCAGTTAATAAAAAAGGAAAAGGTCTATCTGGC
        :::::::::::::: :::::::::::::::::::::::::::::::::::::::: ::::::
Licuw,  ATCAGAGTTAGTCAGTCAAATAATAGAGCAGTTAATAAAAAAGGAAAAGGTCTACCTGGC
              4100      4110      4120      4130      4140      4150

4010      4020      4030      4040      4050      4060
BH 10   ATGGGTACCAGCACACAAAGGAATTGGAGGAAATGAACAAGTAGATAAATTAGTCAGTGC
        ::::::::::::::::::::::::::::::::::::::::::::::::::::::::::::
Licuw,  ATGGGTACCAGCACACAAAGGAATTGGAGGAAATGAACAAGTAGATAAATTAGTCAGTGC
              4160      4170      4180      4190      4200      4210

4070      4080      4090      4100      4110      4120
BH 10   TGGAATCAGGAAAATACTATTTTTAGATGGAATAGATAAGGCCCAAGATGAACATGAGAA
        ::::::::::::: :::::::::::: ::::::::::::::::::::: :::::::::::::
Licuw,  TGGAATCAGGAAAGTACTATTTTTTGAATGGAATAGATAAGGCCCAAGAAGAACATGAGAA
              4220      4230      4240      4250      4260      4270

4130      4140      4150      4160      4170      4180
BH 10   ATATCACAGTAATTGGAGAGCAATGGCTAGTGATTTTAACCTGCCACCTGTAGTAGCAAA
        ::::::::::::::::::::::::::::::::::::::::::::::::::::::::::::
Licuw,  ATATCACAGTAATTGGAGAGCAATGGCTAGTGATTTTAACCTGCCACCTGTAGTAGCAAA
              4280      4290      4300      4310      4320      4330

4190      4200      4210      4220      4230      4240
BH 10   AGAAATAGTAGCCAGCTGTGATAAATGTCAGCTAAAAGGAGAAGCCATGCATGGACAAGT
        ::::::::::::::::::::::::::::::::::::::::::::::::::::::::::::
Licuw,  AGAAATAGTAGCCAGCTGTGATAAATGTCAGCTAAAAGGAGAAGCCATGCATGGACAAGT
              4340      4350      4360      4370      4380      4390

4250      4260      4270      4280      4290      4300
BH 10   AGACTGTAGTCCAGGAATATGGCAACTAGATTGTACACATTTAGAAGGAAAAGTTATCCT
        ::::::::::::::::::::::::::::::::::::::::::::: :::::::: :::::::
Licuw,  AGACTGTAGTCCAGGAATATGGCAACTAGATTGTACACATCTAGAAGGAAAAATTATCCT
              4400      4410      4420      4430      4440      4450

4310      4320      4330      4340      4350      4360
BH 10   GGTAGCAGTTCATGTAGCCAGTGGATATATAGAAGCAGAAGTTATTCCAGCAGAAACAGG
        ::::::::::::::::::::::::::::::::::::::::::::::::::::: :::::
Licuw,  GGTAGCAGTTCATGTAGCCAGTGGATATATAGAAGCAGAAGTTATTCCAGCAGAGACAGG
              4460      4470      4480      4490      4500      4510
```

TABLE III-continued (BH 10 v. LUCIW)
90.0% identity

```
             4370      4380      4390      4400      4410      4420
BH 10   GCAGGAAACAGCATATTTTCTTTTAAAATTAGCAGGAAGATGGCCAGTAAAAACAATACA
        ::::::::::::::::::::::::: :::::::::::::::::::::::::::::::::
Licuw,  GCAGGAAACAGCATATTTTCTCTTAAAATTAGCAGGAAGATGGCCAGTAAAAACAATACA
             4520      4530      4540      4550      4560      4570

4430      4440      4450      4460      4470      4480
BH 10   TACAGACAATGGCAGCAATTTCACCAGTGCTACGGTTAAGGCCGCCTGTTGGTGGGCGGG
        :::::::::::::::::::::::::::::: :::::::::::::::::::::::::: ::
Licuw,  TACAGACAATGGCAGCAATTTCACCAGTACTACGGTTAAGGCCGCCTGTTGGTGGGCAGG
             4580      4590      4600      4610      4620      4630

4490      4500      4510      4520      4530      4540
BH 10   AATCAAGCAGGAATTTGGAATTCCCTACAATCCCCAAAGTCAAGGAGTAGTAGAATCTAT
         ::::::::::::::: :::::::::::::::::::::::::::::::::::::::::::
Licuw,  GATCAAGCAGGAATTTGGCATTCCCTACAATCCCCAAAGTCAAGGAGTAGTAGAATCTAT
             4640      4650      4660      4670      4680      4690

4550      4560      4570      4580      4590      4600
BH 10   GAATAAAGAATTAAAGAAAATTATAGGACAGGTAAGAGATCAGGCTGAACATCTTAAGAC
        ::::: ::::::::::::::::::::::::::::::::::::::::::::: ::::::::
Licuw,  GAATAATGAATTAAAGAAAATTATAGGACAGGTAAGAGATCAGGCTGAACACCTTAAGAC
             4700      4710      4720      4730      4740      4750

4610      4620      4630      4640      4650      4660
BH 10   AGCAGTACAAATGGCAGTATTCATCCACAATTTTAAAAGAAAAGGGGGGATTGGGGGGTA
        ::::::::::::::::::::: ::::::::::::::::::::::::::::::::::: ::
Licuw,  AGCAGTACAAATGGCAGTATTCATCCACAATTTTAAAAGAAAAGGGGGGATTGGGGGATA
             4760      4770      4780      4790      4800      4810

4670      4680      4690      4700      4710      4720
BH 10   CAGTGCAGGGGAAAGAATAGTAGACATAATAGCAACAGACATACAAACTAAAGAATTACA
        :::::::::::::::::::::::::::::::::::::::::::::::::::::: ::::
Licuw,  CAGTGCAGGGGAAAGAATAGTAGACATAATAGCAACAGACATACAAACTAAAGAACTACA
             4820      4830      4840      4850      4860      4870

4730      4740      4750      4760      4770      4780
BH 10   AAAACAAATTACAAAAATTCAAAATTTTCGGGTTTATTACAGGGACAGCAGAAATCCACT
        ::: :::::::::::::::::::::::::::::::::::::::::: :: : :::: ::
Licuw,  AAAGCAAATTACAAAAATTCAAAATTTTCGGGTTTATTACAGGGACAACAAAGATCCCCT
             4880      4890      4900      4910      4920      4930

4790      4800      4810      4820      4830      4840
BH 10   TTGGAAAGGACCAGCAAAGCTCCTCTGGAAAGGTGAAGGGGCAGTAGTAATACAAGATAA
        :::::::::::::::::::::: ::::: :::::::::::::::::::::::::::::::
Licuw,  TTGGAAAGGACCAGCAAAGCTTCTCTGCAAAGGTGAAGGGGCAGTAGTAATACAAGATAA
             4940      4950      4960      4970      4980      4990

4850      4860      4870      4880      4890      4900
BH 10   TAGTGACATAAAAGTAGTGCCAAGAAGAAAAGCAAAGATCATTAGGGATTATGGAAAACA
        :::::::::::::::::::::::::::::::::::::: :::::::::::::::::::::
Licuw,  TAGTGACATAAAAGTAGTGCCAAGAAGAAAAGCAAAAATCATTAGGGATTATGGAAAACA
             5000      5010      5020      5030      5040      5050

4910      4920      4930      4940      4950      4960
BH 10   GATGGCAGGTGATGATTGTGTGGCAAGTAGACAGGATGAGGATTAGAACATGGAAAAGTT
        ::::::::::::::::::::::   :::::::::::::::::::::::::::::::::::
Licuw,  GATGGCAGGTGATGATTGTGT---AAGTAGACAGGATGAGGATTAGAACATGGAAAAGTT
             5060      5070      5080      5090      5100      5110

4970      4980      4990      5000      5010      5020
BH 10   TAGTAAAACACCATATGTATGTTTCAGGGAAAGCTAGGGGATGGTTTTATAGACATCACT
        :::::::::::::::::::::: ::::: :::::::::  :::::::::: ::::::::
Licuw,  TAGTAAAACACCATATGTATATTTCAAAGAAAGCTAAAGGATGGTTTT-TAG-CATCACT
              5120      5130      5140      5150      5160      5170

5030      5040      5050      5060      5070      5080
BH 10   ATGAAAGCCCTCATCCAAGAATAAGTTCAGAAGTACACATCCCACTAGGGGATGCTAGAT
        ::::::  ::::::::::::: ::::::::::::::::::::::  ::::::::::: ::
Licuw,  -TGAAAGTACTCATCCAAGAGTAAGTTCAGAAGTACACATCCCCCTAGGGGATGCTAAAT
              5180      5190      5200      5210      5220      5230
```

TABLE III-continued (BH 10 v. LUCIW)
90.0% identity

```
            5090      5100      5110       5120      5130      5140
BH 10  TGGTAATAACAACATATTGGGGTCTGCATACA-GGAGAAAGAGACTGGCATTTGGGTCAG
       :::::::::::::::::::::::::::::::: ::::::::::: ::::::::::: :::
Licuw, TGGTAATAACAACATATTGGGGTCTGCATACAAGGAGAAAGAGAATGGCATTTGGG-CAG
             5240      5250      5260      5270      5280

5150      5160      5170      5180      5190      5200
BH 10  GGAGTCTCCATAGAATGGAGGAAAAAGAGATATAGCACACAAGTAGACCCTGAACTAGCA
       :: ::: :::::::::::::  :::::: :: ::::::::::::::::::::  ::::::
Licuw, GG-GTCGCCATAGAATGGAG--AAAAGA-AT-TAGCACACAAGTAGACCCTGGCCTAGCA
    5290       5300        5310        5320      5330      5340

5210      5220      5230      5240      5250      5260
BH 10  GACCAACTAATTCATCTGTATTACTTTGACTGTTTTTCAGACTCTGCTATAAGAAAGGCC
       :::::::::::::::::: :::: ::::: ::::::::::: :::::::::: ::: :::
Licuw, GACCAACTAATTCATCTGCATTATTTTGATTGTTTTTCAGAATCTGCTATAAAAAATGCC
         5350      5360      5370      5380      5390      5400

5270      5280      5290      5300      5310      5320
BH 10  TTATTAGGACACATAGTTAGCCCTAGGTGTGAATATCAAGCAGGACATAACAAGGTAGGA
        :::::::: : :::::: ::::: :::::::::::::::::::::::::::::::::::
Licuw, ATATTAGGATATAGAGTTAGTCCTAGCTGTGAATATCAAGCAGGACATAACAAGGTAGGA
         5410      5420      5430      5440      5450      5460

5330      5340      5350      5360      5370      5380
BH 10  TCTCTACAATACTTGGCACTAGCAGCATTAATAACACCAAAAAAGATAAAGCCACCTTTG
       :::::::::::::::::::::::::::::::::::::::::::::: :::::::::::::
Licuw, TCTCTACAATACTTGGCACTAGCAGCATTAATAACACCAAAAAAGACAAAGCCACCTTTG
         5470      5480      5490      5500      5510      5520

5390      5400      5410      5420      5430      5440
BH 10  CCTAGTGTTACGAAACTGACAGAGGATAGATGGAACAAGCCCCAGAAGACCAAGGGCCAC
       :::::::::: :::::::::::::::::::::::::::::::::::::::::::::::::
Licuw, CCTAGTGTTAAGAAACTGACAGAGGATAGATGGAACAAGCCCCAGAAGACCAAGGGCCAC
         5530      5540      5550      5560      5570      5580

5450      5460      5470      5480      5490      5500
BH 10  AGAGGGAGCCACACAATGAATGGACACTAGAGCTTTTAGAGGAGCTTAAGAATGAAGCTG
       ::::::::::: :::::::::::::::::::::::::::::::  :::::::
Licuw, AGAGGGAGCCATACAATGAATGGACACTAGAGCTTTTAGAGGAGCTTAAGAGAGAAGCTG
         5590      5600      5610      5620      5630      5640

5510      5520      5530      5540      5550      5560
BH 10  TTAGACATTTTCCTAGGATTTGGCTCCATGGCTTAGGGCAACATATCTATGAAACTTATG
       :::::::::::::::::   ::::::::: ::::::: ::: ::::::::::::::::::
Licuw, TTAGACATTTTCCTAGGCCATGGCTCCATAGCTTAGGACAATATATCTATGAAACTTATG
         5650      5660      5670      5680      5690      5700

5570      5580      5590      5600      5610      5620
BH 10  GGGATACTTGGGCAGGAGTGGAAGCCATAATAAGAATTCTGCAACAACTGCTGTTTATCC
       :::::::::::::::::::::::::::::::::::::::::::::::::::::::::: :
Licuw, GGGATACTTGGGCAGGAGTGGAAGCCATAATAAGAATTCTGCAACAACTGCTGTTTATTC
         5710      5720      5730      5740      5750      5760

5630      5640      5650      5660      5670      5680
BH 10  ATTTTCAGAATTGGGTGTCGACATAGCAGAATAGGCGTTACTCGACAGAGGAGAGCAAGA
       :::: :::::::::::::: :::::::::::::::: ::: :: ::::::::::::::::
Licuw, ATTT-CAGAATTGGGTGTCAACATAGCAGAATAGGCATTATTCAACAGAGGAGAGCAAGA
          5770      5780      5790      5800      5810      5820

5690      5700      5710      5720      5730
BH 10  A---ATGGAGCCAGTAGATCCTAGACTAGAGCCCTGGAAGCATCCAGGAAGTCAGCCTAA
       :   :::::::::::::::::::  ::::::::::::::::::::::::::::::::::
Licuw, AGAAATGGAGCCAGTAGATCCTAATCTAGAGCCCTGGAAGCATCCAGGAAGTCAGCCTAG
          5830      5840      5850      5860      5870      5880

5740      5750      5760      5770      5780      5790
BH 10  AACTGCTTGTACCAATTGCTATTGTAAAAAGTGTTGCTTTCATTGCCAAGTTTGTTTCAT
        :::::::::: :::::::::::::::::::::::::::::::::: : :  :::::::
Licuw, GACTGCTTGTAACAATTGCTATTGTAAAAAGTGTTGCTTTCATTGCTACGCGTGTTTCAC
          5890      5900      5910      5920      5930      5940

5800      5810      5820      5830      5840      5850
BH 10  AACAAAAGCCTTAGGCATCTCCTATGGCAGGAAGAAGCGGAGACAGCGACGAAGACCTCC
       :: ::::: :::::::::::::::::::::::::::::::::::::::::::::: ::::
Licuw, AAGAAAAGGCTTAGGCATCTCCTATGGCAGGAAGAAGCGGAGACAGCGACGAAGAGCTCC
          5950      5960      5970      5980      5990      6000
```

TABLE III-continued (BH 10 v. LUCIW)
90.0% identity

```
              5860      5870      5880      5890      5900      5910
BH 10   TCAAGGCAGTCAGACTCATCAAGTTTCTCTATCAAAGCAGTAAGTAGTACATGTAATGCA
        ::: : :::::::::::::::::: :::::::::::::::::::::::: ::::::::::
Licuw,  TCAGGACAGTCAGACTCATCAAGCTTCTCTATCAAAGCAGTAAGTAGTAAATGTAATGCA
              6010      6020      6030      6040      6050      6060

5920      5930      5940      5950      5960      5970
BH 10   ACCTATACAAATA---GCAATAGTAGCATTAGTAGTAGCAATAATAATAGCAATAGTTGT
        : :: :::::::::     :::::::::: :::::::::: : :::::::::::::::::
Licuw,  ATCTTTACAAATATTAGCAATAGTATCATTAGTAGTAGTAGCAATAATAGCAATAGTTGT
              6070      6080      6090      6100      6110      6120

5980      5990      6000      6010      6020      6030
BH 10   GTGGTCCATAGTAATCATAGAATATAGGAAAATATTAAGACAAAGAAAAATAGACAGGTT
        :::: :::::::: :::::::::::::::::::::::::::::::::::: :::::: ::
Licuw,  GTGGACCATAGTACTCATAGAATATAGGAAAATATTAAGACAAAGAAAA-TAGACAGATT
              6130      6140      6150      6160      6170      6180

6040      6050      6060      6070      6080
BH 10   AATTGATAGACTAATAGAAAGAGCAGAAGACAGTGGCAATGAGAGTGAAGGAGA------
        :::::::::: ::: ::::: ::::::::::::::::::::::::: :::::: ::
Licuw,  AATTGATAGAATAAGAGAAAAAGCAGAAGACAGTGGCAATGAAAGTGAAGGGGACCAGGA
              6190      6200      6210      6220      6230      6240

6090      6100      6110      6120      6130      6140
BH 10   ---AATATCAGCACTTGTGGAGATGGGGGTGGAGATGGGGCACCATGCTCCTTGGGATGT
           : ::::::::::::::::::::::::                :::: :::::::::::::
Licuw,  GGAATTATCAGCACTTGTGGAGATGGGG------------CACCTTGCTCCTTGGGATGT
              6250      6260      6270                6280      6290

6150      6160      6170      6180      6190      6200
BH 10   TGATGATCTGTAGTGCTACAGAAAAATTGTGGGTCACAGTCTATTATGGGGTACCTGTGT
        :::::::::::::::::::::::::::::::::::::::::: :::::::: ::::::::
Licuw,  TGATGATCTGTAGTGCTACAGAAAAATTGTGGGTCACAGTTTATTATGGAGTACCTGTGT
              6300      6310      6320      6330      6340      6350

6210      6220      6230      6240      6250      6260
BH 10   GGAAGGAAGCAACCACCACTCTATTTTGTGCATCAGATGCTAAAGCATATGATACAGAGG
        :::: :::::::: :::::::::::::::::::::::::: :::::::::::::::::::
Licuw,  GGAAAGAAGCAACTACCACTCTATTTTGTGCATCAGATGCTAGAGCATATGATACAGAGG
              6360      6370      6380      6390      6400      6410

6270      6280      6290      6300      6310      6320
BH 10   TACATAATGTTTGGGCCACACATGCCTGTGTACCCACAGACCCCAACCCACAAGAAGTAG
        ::::::::::::::::::::::::::::::::::::::::::::::::::::::::::::
Licuw,  TACATAATGTTTGGGCCACACATGCCTGTGTACCCACAGACCCCAACCCACAAGAAGTAG
              6420      6430      6440      6450      6460      6470

6330      6340      6350      6360      6370      6380
BH 10   TATTGGTAAATGTGACAGAAAATTTTAACATGTGGAAAAATGACATGGTAGAACAGATGC
        ::::::: ::::::::::::::::::::::::::::::::::: ::::::::::::::::
Licuw,  TATTGGGAAATGTGACAGAAAATTTTAACATGTGGAAAAATAACATGGTAGAACAGATGC
              6480      6490      6500      6510      6520      6530

6390      6400      6410      6420      6430      6440
BH 10   ATGAGGATATAATCAGTTTATGGGATCAAAGCCTAAAGCCATGTGTAAAATTAACCCCAC
        : :::::::::::::::::::::::::::::::::::::::::::::::::::::::::
Licuw,  AGGAGGATATAATCAGTTTATGGGATCAAAGCCTAAAGCCATGTGTAAAATTAACCCCAC
              6540      6550      6560      6570      6580      6590

6450      6460      6470      6480      6490      6500
BH 10   TCTGTGTTAGTTTAAAGTGCACTGATTTGAAGAATGATACTAATACCAATAGTAGTAGCG
        ::::::::: :::::: ::::::::::: :::   : :::::::::::::::::::::
Licuw,  TCTGTGTTACTTTAAATTGCACTGATTTGGGGAAGGCTACTAATACCAATAGTAGTAATT
              6600      6610      6620      6630      6640      6650

6510      6520      6530      6540      6550      6560
BH 10   GGAGA-ATGATAATGGAGAAAGGAGAGATAAAAAACTGCTCTTTCAATATCAGCACAAGC
        ::: : : :: :::       ::::::::: :::::::::::::::::::::: :::::
Licuw,  GGAAAGAAGA-AATA---AAAGGAGAAATAAAAAACTGCTCTTTCAATATCACCACAAGC
              6660      6670      6680      6690      6700
```

TABLE III-continued (BH 10 v. LUCIW)
90.0% identity

```
           6570      6580      6590      6600      6610      6620
BH 10  ATAAGAGGTAAGGTGCAGAAAGAATATGCATTTTTTTATAAACTTGATATAATACCAATA
       :::::::  ::::  :  :::::::::  ::::: ::::  :::  :::::: :: ::::::::
Licuw, ATAAGAGATAAGATTCAGAAAGAAAATGCACTTTTTCGTAACCTTGATGTAGTACCAATA
           6710      6720      6730      6740      6750      6760

6630      6640      6650      6660
BH 10  GATAATGATA------CTACCAGCTATAC---------GTTGACAAGTTGTAACACCTCA
       :::::::: ::      ::::::  ::::::         ::::: :  :::::::::  :::
Licuw, GATAATGCTAGTACTACTACCAACTATACCAACTATAGGTTGATACATTGTAACAGATCA
           6770      6780      6790      6800      6810      6820

6670      6680      6690      6700      6710      6720
BH 10  GTCATTACACAGGCCTGTCCAAAGGTATCCTTTGAGCCAATTCCCATACATTATTGTGCC
       :::::::::::::::::::::::::::::::::: :::::::::::::::::::::::::::: ::
Licuw, GTCATTACACAGGCCTGTCCAAAGGTATCATTTGAGCCAATTCCCATACATTATTGTACC
           6830      6840      6850      6860      6870      6880

6730      6740      6750      6760      6770      6780
BH 10  CCGGCTGGTTTTGCGATTCTAAAATGTAATAATAAGACGTTCAATGGAACAGGACCATGT
       ::::::::::::: :::::::::::::::    ::::::::::::::::  ::::: ::::::::::::::::
Licuw, CCGGCTGGTTTTGCGATTCTAAAGTGTAATAATAAAACGTTCAATGGAAAAGGACCATGT
           6890      6900      6910      6920      6930      6940

6790      6800      6810      6820      6830      6840
BH 10  ACAAATGTCAGCACAGTACAATGTACACATGGAATTAGGCCAGTAGTATCAACTCAACTG
       :::::::::::::::::::::::::::::::::::::::::::::  ::::::  :::::::::::::
Licuw, ACAAATGTCAGCACAGTACAATGTACACATGGAATTAGGCCAATAGTGTCAACTCAACTG
           6950      6960      6970      6980      6990      7000

6850      6860      6870      6880      6890      6900
BH 10  -CTGTTAAATGGCAGTCTAGCAGAAGAAGAGGTAGTAATTAGATCTGCCAATTTCACAGA
        :::::::::::::::::::::::::::::::::::::::::::::::::::: ::::::::::  :
Licuw, TCTGTTAAATGGCAGTCTAGCAGAAGAAGAGGTAGTAATTAGATCTGACAATTTCACGAA
           7010      7020      7030      7040      7050      7060

6910      6920      6930      6940      6950      6960
BH 10  CAATGCTAAAACCATAATAGTACAGCTGAACCAATCTGTAGAAATTAATTGTACAAGACC
       ::::::::::::::::::::::::::::::: :::::::::::  ::::::::: ::::::::::::
Licuw, CAATGCTAAAACCATAATAGTACAGCTGAATGAATCTGTAGCAATTAACTGTACAAGACC
           7070      7080      7090      7100      7110      7120

6970      6980      6990      7000      7010      7020
BH 10  CAACAACAATACAAGAAAAAGTATCCGTATCCAGAGAGGACCAGGGAGAGCATTTGTTAC
       ::::::::::::::::::::::::::::::::::: :::         ::::::::::::::::::::  :::
Licuw, CAACAACAATACAAGAAAAAGTATCTATAT------AGGACCAGGGAGAGCATTTCATAC
           7130      7140      7150              7160      7170      7180

7030      7040      7050      7060      7070      7080
BH 10  AATAGGAAAAATA---GGAAATATGAGACAAGCACATTGTAACATTAGTAGAGCAAAATG
       ::  :::::  ::::     :::  ::::::::::::::::::::::::::::::::::::::::::::
Licuw, AACAGGAAGAATAATAGGAGATATAAGAAAAGCACATTGTAACATTAGTAGAGCACAATG
                 7190      7200      7210      7220      7230      7240

7090      7100      7110      7120      7130      7140
BH 10  GAATAACACTTTAAAACAGATAGATAGCAAATTAAGAGAACAATTTGGAAATAATAAAAC
       ::::::::::::: :::::::::::::::: ::  ::::::::::::::::  :::::::::::: ::::::::::
Licuw, GAATAACACTTTAGAACAGATAGTTAAAAAATTAAGAGAACAGTTTGGGAATAATAAAAC
            7250      7260      7270      7280      7290      7300

7150      7160      7170      7180      7190      7200
BH 10  AATAATCTTTAAGCAGTCCTCAGGAGGGGACCCAGAAATTGTAACGCACAGTTTTAATTG
       :::: :::::::::  :::::::::::::::::::::::::::::::::::::  ::::::::::::::::::
Licuw, AATAGTCTTTAATCAATCCTCAGGAGGGGACCCAGAAATTGTAATGCACAGTTTTAATTG
           7310      7320      7330      7340      7350      7360

7210      7220      7230      7240      7250      7260
BH 10  TGGAGGGGAATTTTTCTACTGTAATTCAACACAACTGTTTAATAGTACTTGGT--TTAAT
       : :::::::::::::::::::::::::::  :::::::::::::::::::::::::  :::: :::::
Licuw, TAGAGGGGAATTTTTCTACTGTAATACAACACAACTGTTTAATAATACATGGAGGTTAA-
                7370      7380      7390      7400      7410

7270      7280      7290      7300      7310      7320
BH 10  AGTACTTGGAGTACTAAAGGGTCAAATAACACTGAAGGAAGTGACACAATCACCCCTCCCA
       :  :::     ::: ::::            :::  ::::::  ::::::::::::  ::::::
Licuw, ATCAC-------ACTGAAGGA---------ACTAAAGGAAATGACACAATCATACTCCCA
           7420          7430                7440      7450      7460
```

TABLE III-continued (BH 10 v. LUCIW)
90.0% identity

```
            7330      7340      7350      7360      7370      7380
BH 10   TGCAGAATAAAACAAATTATAAACATGTGGCAGGAAGTAGGAAAAGCAATGTATGCCCCT
        ::  ::::::::::::::::::::::::::::::::::::::::::::::::::::::::
Licuw,  TGTAGAATAAAACAAATTATAAACATGTGGCAGGAAGTAGGAAAAGCAATGTATGCCCCT
            7470      7480      7490      7500      7510      7520

7390      7400      7410      7420      7430      7440
BH 10   CCCATCAGTGGACAAATTAGATGTTCATCAAATATTACAGGGCTGCTATTAACAAGAGAT
        :::::  : :::::::::::: :::::::::::::::::::::::::::::::::::::
Licuw,  CCCATTGGAGGACAAATTAGTTGTTCATCAAATATTACAGGGCTGCTATTAACAAGAGAT
            7530      7540      7550      7560      7570      7580

7450      7460      7470      7480      7490      7500
BH 10   GGTGGTAATA--GCAAC-AATGAGTCCGAGATCTTCAGACCTGGAGGAGGAGATATGAGG
        :::::::  :  : ::: ::::: ::::: ::::::::::::::::::::::::::::::
Licuw,  GGTGGTACAAATGTAACTAATGACACCGAGGTCTTCAGACCTGGAGGAGGAGATATGAGG
            7590      7600      7610      7620      7630      7640

7510      7520      7530      7540      7550      7560
BH 10   GACAATTGGAGAAGTGAATTATATAAATATAAAGTAGTAAAAATTGAACCATTAGGAGTA
        ::::::::::::::::::::::::::::::::::::: ::::::::::::::::::: ::
Licuw,  GACAATTGGAGAAGTGAATTATATAAATATAAAGTAATAAAAATTGAACCATTAGGAATA
            7650      7660      7670      7680      7690      7700

7570      7580      7590      7600      7610
BH 10   GCACCCACCAAGGCAAAGAGAAGAGTGGTGCAGAGAGAAAAAAGAGCAGTGGGAATAG--
        ::::::::::::::::::::::::::::::::::::::::::::::::::::::::::
Licuw,  GCACCCACCAAGGCAAAGAGAAGAGTGGTGCAGAGAGAAAAAAGAGCAGTGGGAATAGTA
            7710      7720      7730      7740      7750      7760

7620      7630      7640      7650      7660      7670
BH 10   -GAGCTTTGTTCCTTGGGTTCTTGGGAGCAGCAGGAAGCACTATGGGCGCAGCGTCAATG
         :::: : :::::::::::::::::::::::::::::::::::::::::  :::: :: ::
Licuw,  GGAGCTATGTTCCTTGGGTTCTTGGGAGCAGCAGGAAGCACTATGGGGCGCAGTGTCATTG
            7770      7780      7790      7800      7810      7820

7680      7690      7700      7710      7720      7730
BH 10   ACGCTGACGGTACAGGCCAGACAATTATTGTCTGGTATAGTGCAGCAGCAGAACAATTTG
        ::::::::::::::::::::::::::::::::::::::::::: :::::::::::::::
Licuw,  ACGCTGACGGTACAGGCCAGACAATTATTGTCTGGTATAGTGCAACAGCAGAACAATTTG
            7830      7840      7850      7860      7870      7880

7740      7750      7760      7770      7780      7790
BH 10   CTGAGGGCTATTGAGGCGCAACAGCATCTGTTGCAACTCACAGTCTGGGGCATCAAGCAG
        :::::::::::::::::::::::: :::::::::::::::::::::::::::::::::::
Licuw,  CTGAGGGCTATTGAGGCGCAACAACATCTGTTGCAACTCACAGTCTGGGGCATCAAGCAG
            7890      7900      7910      7920      7930      7940

7800      7810      7820      7830      7840      7850
BH 10   CTCCAGGCAAGAATCCTGGCTGTGGAAAGATACCTAAAGGATCAACAGCTCCTGGGGATT
        :::::::::::: ::::::::::::::::::::::::: ::::::::::::::  :::
Licuw,  CTCCAGGCAAGAGTCCTGGCTGTGGAAAGATACCTAAGGGATCAACAGCTCCTAG--ATT
            7950      7960      7970      7980      7990      8000

7860      7870      7880      7890      7900      7910
BH 10   TGGGGTTGCTCTGGAAAACTCATTTGCACCACTGCTGTGCCTTGGAATGCTAGTTGGAGT
        ::::::  :::::::::: :::::::::::::::::::::::::::::::::::::::
Licuw,  TGGGGT-GCTCTGGAAA-CTCATTTGCACCACTGCTGTGCCTTGGAATGCTAGTTGGAGT
                8010      8020      8030      8040      8050

7920      7930      7940      7950      7960      7970
BH 10   AATAAATCTCTGGAACAGATTTGGAATAACATGACCTGGATGGAGTGGGACAGAGAAATT
        :::::::::::::::: : :::::: ::::::::::::::: ::: ::::::: ::::::
Licuw,  AATAAATCTCTGGAAGACATTTGGGATAACATGACCTG-ATGCAGTGGGAAAGAGAAATT
             8060      8070      8080      8090      8100      8110

7980      7990      8000      8010      8020      8030
BH 10   AACAATTACACAAGCTTAATACACTCCTTAATTGAAGAATCGCAAAACCAGCAAGAAAAG
        :::::::::: : :::: :: :: ::::::: :::::::::::: ::::: ::::::::
Licuw,  GACAATTACACAAACACAATATACACCTTACTTGAAGAATCGCAGAACCAACAAGAAAAG
             8120      8130      8140      8150      8160      8170
```

TABLE III-continued (BH 10 v. LUCIW)
90.0% identity

```
           8040      8050      8060      8070      8080      8090
BH 10  AATGAACAAGAATTATTGGAATTAGATAAATGGGCAAGTTTGTGGAATTGGTTTAACATA
       ::::::::::::::::::::: ::::: :::::  :::::::::::::::::::::: ::::
Licuw, AATGAACAAGAATTATTAGAATTGGATAAGTGGGCAAGTTTGTGGAATTGGTTTAGCATA
           8180      8190      8200      8210      8220      8230

8100      8110      8120      8130      8140      8150
BH 10  ACAAATTGGCTGTGGTATATAAAATTATTCATAATGATAGTAGGAGGCTTGGTAGGTTTA
       ::::: :::::::::::::::: ::::::::::::::::::::::::::::::::::::::
Licuw, ACAAACTGGCTGTGGTATATAAAGATATTCATAATGATAGTAGGAGGCTTGGTAGGTTTA
           8240      8250      8260      8270      8280      8290

8160      8170      8180      8190      8200      8210
BH 10  AGAATAGTTTTTGCTGTACTTTCTGTAGTGAATAGAGTTAGGCAGGGATATTCACCATTA
       :::::::::::::::::: ::::: ::::::::::::::::::::::::::: ::::::::
Licuw, AGAATAGTTTTTGCTGTGCTTTCTATAGTGAATAGAGTTAGGCAGGGATACTCACCATTG
           8300      8310      8320      8330      8340      8350

8220      8230      8240      8250      8260      8270
BH 10  TCGTTTCAGACCCACCTCCCAATCCCGAGGGGACCCGACAGGCCCGAAGGAATAGAAGAA
       ::  :::::::::: ::::: : ::::    :::::::: ::::: ::::: ::::::
Licuw, TCATTTCAGACCCGGCTCCCAGTGCCGAG---ACCCGACAG-CCCGACGGAATCGAAGAA
           8360      8370      8380      8390      8400      8410

8280      8290      8300      8310      8320      8330
BH 10  GAAGGGGAGAGAGAGACAGAGACAGATCCATTCGATTAGTGAACGGATCCTTAGCACTTA
       :::::::::::::::::::::::::::::: :::::::::: :::: ::::::::::::
Licuw, GAAGGGGAGAGAGAGACAGAGACAGATCCGTTCGATTAGTGGATGGATTCTTAGCACTTA
           8420      8430      8440      8450      8460      8470

8340      8350      8360      8370      8380      8390
BH 10  TCTGGGACGATCTGCGGAGCCTGTGCCTCTTCAGCTACCACCGCTTGAGAGACTTACTCT
       ::::::: :::::::::::::::::::::::::::::::::  :: :::::::::::::::
Licuw, TCTGGGAAGATCTGCGGAGCCTGTGCCTCTTCAGCTACCGGCGGTTGAGAGACTTACTCT
           8480      8490      8500      8510      8520      8530

8400      8410      8420      8430      8440      8450
BH 10  TGATTGTAACGAGGATTGTGGAACTTCTGGGACGCAGGGGGTGGGAAGCCCTCAAATATT
       :::::: : :::::  ::::::: :::::::: ::::::::::::::   ::::::::::
Licuw, TGATTGCAGCGAGGACTGTGGAAATTCTGGGGCACAGGGGGTGGGAA---CTCAAATATT
           8540      8550      8560      8570      8580      8590

8460      8470      8480      8490      8500      8510
BH 10  GGTGGAATCTCCTACAGTATTGGAGTCAGGAGCTAAAGAATAGTGCTGTTAGCTTGCTCA
       :::::: ::::::: ::::::::: ::::: :::::::::::::::::::::::: ::::
Licuw, GGTGGAGTCTCCTGCAGTATTGGATTCAGGAACTAAAGAATAGTGCTGTTAGCTGGCTCA
           8600      8610      8620      8630      8640      8650

8520      8530      8540      8550      8560      8570
BH 10  ATGCCACAGCTATAGCAGTAGCTGAGGGGACAGATAGGGTTATAGAAGTAGTACAAGGAG
       : ::::::::::::::::::::: ::::::::::::::::::::::::::: :: :::::
Licuw, ACGCCACAGCTATAGCAGTAACTGAGGGGACAGATAGGGTTATAGAAGTAGCACAAAGAG
           8660      8670      8680      8690      8700      8710

8580      8590      8600      8610      8620      8630
BH 10  CTTATAGAGCTATTCGCCACATACCTAGAAGAATAAGACAGGGCTTGGAAAGGATTTTGC
       :::::::::::::::: ::::::::: :: :::::::::    :::::::::: ::::::
Licuw, CTTATAGAGCTATTCTCCACATACATAGAAGAATTAGACA---CTTGGAAAGGCTTTTGC
           8720      8730      8740      8750      8760

8640      8650      8660      8670      8680      8690
BH 10  TATAAGATGGGTGGCAAGTGGTCAAAAAGTAGTGTGGTTGGATGGCCTGCTGTAAGGGAA
       ::::::::::::  :   :::::::::: ::   ::: ::::: :::::  :::::::::
Licuw, TATAAGATGGGGG---AGTGGTCAAAACG-AGTATGGG-GGATGGTCTGCTATAAGGGAA
           8770      8780      8790      8800      8810      8820

8700      8710                8720      8730      8740
BH 10  AGAATGAGACGAGCTGAGCCA------------GCAGCAGATGGGGTGGGAGCAGCATCT
       :::::::::::::::::::::::           :::::::::::: :::  ::: ::::
Licuw, AGAATGAGACGAGCTGAGCCACGAGCTGAGCCAGCAGCAGATGGG-TGGGA-CAGTATCT
           8830      8840      8850      8860      8870      8880

8750      8760      8770      8780      8790      8800
BH 10  CGAGACCTAGAAAAACATGGAGCAATCACAAGTAGCAACACAGCAGCTAACAATGCTGAT
       :::::::: :::::::::::   ::::::::::::::::::: ::::: ::::::::::
Licuw, CGAGACCTGGAAAAACATGGA--AATCACAAGTAGCAATACAGCAGCTACTAATGCTGAT
           8890      8900      8910      8920      8930
```

TABLE III-continued (BH 10 v. LUCIW)
90.0% identity

```
              8810      8820      8830      8840      8850      8860
BH 10   TGTGCCTGGCTAGAAGCACAAGAGGAGGAGGAGGTGGGTTTTCCAGTCACACCTCAGGTA
        ::::::::::::::::::::::::::::::::::: :::::::::::::::: :::::::::
Licuw,  TGTGCCTGGCTAGAAGCACAAGAGGAGGAAGAGGTGGGTTTTCCAGTCAGACCTCAGGTA
              8940      8950      8960      8970      8980      8990

8870      8880      8890      8900      8910      8920
BH 10   CCTTTAAGACCAATGACTTACAAGGCAGCTGTAGATCTTAGCCACTTTTTAAAAGAAAAG
        ::::::::::::::::::::::::::::::::: :::::  :::: ::::::::::::::::
Licuw,  CCTTTAAGACCAATGACTTACAAGGCAGCTTTAGATATTAGCCACTTTTTAAAAGAAAAG
              9000      9010      9020      9030      9040      9050

8930      8940      8950      8960      8970      8980
BH 10   GGGGGACTGGAAGGGCTAATTCACTCCCAACGAAGACAAGATATCCTTGATCTGTGGATC
        :::::::::::::::::::::: :::::: :::::::::::::::: :::::::::::::::
Licuw,  GGGGGACTGGAAGGGCTAATTTGGTCCCAAAGAAGACAAGAGATCCTTGATCTGTGGATC
              9060      9070      9080      9090      9100      9110

8990      9000      9010      9020      9030      9040
BH 10   TACCACACACAAGGCTACTTCCCTGATTAGCAGAACTACACACCAGGGCCAGGGATCAGA
        :::::::::::::::::::::::::::::::: :::::: ::::::::::::::::::::::
Licuw,  TACCACACACAAGGCTACTTCCCTGATTGGCAGAATTACACACCAGGGCCAGGGATCAGA
              9120      9130      9140      9150      9160      9170

9050      9060      9070      9080      9090      9100
BH 10   TATCCACTGACCTTTGGATGGTGCTACAAGCTAGTACCAGTTGAGCCAGAGAAGTTAGAA
        :::::::::::::::::::::::::: :::::::::::::::::::::::::::::: :::::
Licuw,  TATCCACTGACCTTTGGATGGTGCTTCAAGCTAGTACCAGTTGAGCCAGAGAAGGTAGAA
              9180      9190      9200      9210      9220      9230

9110      9120      9130      9140      9150      9160
BH 10   GAAGCCAACAAAGGAGAGAACACCAGCTTGTTACACCCTGTGAGCCTGCATGGAATGGAT
        ::  :::::  :::::::::::::: ::::::::::::::: :::::::::::::::::  ::::
Licuw,  GAGGCCAATGAAGGAGAGAACAA-AGCTTGTTACACCCTATGAGCCTGCATGGGATGGAG
              9240      9250      9260      9270      9280      9290

9170      9180      9190      9200      9210      9220
BH 10   GACCCGGAGAGAGAAGTGTTAGAGTGGAGGTTTGACAGCCGCCTAGCATTTCATCACATG
        :::  ::::::  ::::::::::::: ::::::::::::::::  :::::::::::::::::::
Licuw,  GACGCGGAGAAAGAAGTGTTAGTGTGGAGGTTTGACAGCAAACTAGCATTTCATCACATG
              9300      9310      9320      9330      9340      9350

9230      9240      9250      9260      9270      9280
BH 10   GCCCGAGAGCTGCATCCGGAGTACTTCAAGAACTGCTGACATCGAGCTTGCTACAAGGGA
        :::::::::::::::::::::::::::::  :::  ::::::::::::::::: :::::::::::
Licuw,  GCCCGAGAGCTGCATCCGGAGTACTACAAAGACTGCTGACATCGAGCTTTCTACAAGGGA
              9360      9370      9380      9390      9400      9410

9290      9300      9310      9320      9330      9340
BH 10   CTTTCCGCTGGGGACTTTCCAGG-AGGCGTGGCCTGGGCGGGACTGGGGAGTGGCGAGCC
        :::::::::::::::::::::::: :::::::::::::::::::::::::::::::::::  ::
Licuw,  CTTTCCGCTGGGGACTTTCCAGGGAGGCGTGGCCTGGGCGGGACTGGGGAGTGGCGT-CC
              9420      9430      9440      9450      9460      9470

9350      9360      9370      9380      9390      9400
BH 10   CTCAGATCCTGCATATAAGGAGCTGCTTTTTGCCTGTACTGGGTCTCTCTGGTTAGACCA
        ::::::  ::::::::::::::  :::::::::::::::::::::::::::::::::::::::
Licuw,  CTCAGATGCTGCATATAAGCAGCTGCTTTTTGCCTGTACTGGGTCTCTCTGGTTAGACCA
              9480      9490      9500      9510      9520      9530

9410      9420
BH 10   GATCTGAGCCTGGGAGCTC-----------------------------------------
        :::::::::::::::::::
Licuw,  GATCTGAGCCTGGGAGCTCTCTGGCTAACTAGGGAACCCACTGCTTAAGCCTCAATAAAG
              9540      9550      9560      9570      9580      9590

BH 10   ------------------------------------------------------------

Licuw,  CTTGCCTTGAGTGCTTCAAGTAGTGTGTGCCCGTCTGTTGTGTGACTCTGGTAACTAGAG
              9600      9610      9620      9630      9640      9650

BH 10   ----------------------------------------

Licuw,  ATCCCTCAGACCCTTTTAGTCAGTGTGGAAAAATCTCTAGCAG
              9660      9670      9680      9690      9700
```

What we claim is:

1. A composition comprising a duplex formed between a Human Immunodeficiency Virus Type-1 (HIV-1) nucleic acid and a single-stranded nucleic acid of at least 18 contiguous nucleotides comprising a nucleotide sequence selected from the group consisting of:
   (i) a nucleotide sequence of either strand of viral DNA from lambda bacteriophage λ-HXB$_2$ having ATCC Accession No. 40231;
   (ii) a nucleotide sequence of either strand of viral DNA from lambda bacteriophage λ-HXB$_3$ having ATCC Accession No. 40232;
   (iii) a nucleotide sequence of either strand of viral DNA from clone BH10 having ATCC Accession No. 40125;
   (iv) a nucleotide sequence of either strand of viral DNA from clone BH5 having ATCC Accession No. 40126;
   (v) a nucleotide sequence of either strand of viral DNA from clone BH8 having ATCC Accession No. 40127;
   (vi) a nucleotide sequence of either strand of viral DNA from clone pHXB3 having ATCC Accession No. 67081;
   (vii) a nucleotide sequence of either strand of viral DNA from clone pHXB-2D having ATCC Accession No. 67082;
   (viii) a nucleotide sequence of either strand of viral DNA from *E. coli* clone X10-1 having ATCC Accession No. 67083; and
   (ix) an HIV-1 nucleotide sequence from the H9/HTLV-III cell line having ATCC Accession No. CRL 8543;
   wherein the single-stranded nucleic acid does not form a duplex with HTLV-I and HTLV-II nucleic acids under conditions of stringency for hybridization under which the single-stranded nucleic acid forms a duplex with the HIV-1 nucleic acid;
   wherein the duplex is outside of a mammalian cell and outside of an HIV-1 particle;
   wherein the duplex comprises a double-stranded region of at least 18 contiguous nucleotides and a single-stranded region on either side of the double-stranded region that is longer than the double-stranded region; and
   wherein the single-stranded nucleic acid comprises a label.

2. The composition of claim 1, wherein the single-stranded nucleic acid comprises a nucleotide sequence which is part of an HIV-1 gag open reading frame, an HIV-1 pol open reading frame, an HIV-1 env open reading frame or part of an HIV-1 long terminal repeat region.

3. The composition of claim 1, wherein the single-stranded nucleic acid is selected from the group consisting of:
   (i) a single-stranded nucleic acid consisting of from 18 to 103 nucleotides comprising a nucleotide sequence of at least 18 contiguous nucleotides from an HIV-1 gag open reading frame, an HIV-1 env open reading frame, an HIV-1 pol open reading frame or from an HIV-1 long terminal repeat region;
   (ii) a single-stranded nucleic acid consisting of from 32 to 103 nucleotides comprising a nucleotide sequence of at least 32 contiguous nucleotides from an HIV-1 gag open reading frame, an HIV-1 env open reading frame, an HIV-1 pol open reading frame or from an HIV-1 long terminal repeat region;
   (iii) a single-stranded nucleic acid consisting of from 20 to 100 nucleotides comprising a nucleotide sequence of at least 20 contiguous nucleotides from an HIV-1 gag open reading frame, an HIV-1 env open reading frame, an HIV-1 pol open reading frame or from an HIV-1 long terminal repeat region;
   (iv) a single-stranded nucleic acid comprising a nucleotide sequence of at least about 32 contiguous nucleotides from an HIV-1 gag open reading frame, an HIV-1 env open reading frame, an HIV-1 pol open reading frame or from an HIV-1 long terminal repeat region; and
   (v) a single-stranded nucleic acid comprising a nucleotide sequence of at least about 20 contiguous nucleotides from an HIV-1 gag open reading frame, an HIV-1 env open reading frame, an HIV-1 pol open reading frame or from an HIV-1 long terminal repeat region.

4. The composition of claim 1, wherein the duplex is bound to a solid support.

5. The composition of claim 1, wherein the single-stranded nucleic acid is randomly generated from an HIV-1 nucleic acid.

6. The composition of claim 1, wherein the single-stranded nucleic acid comprises DNA.

7. The composition of claim 1, wherein the single-stranded nucleic acid comprises RNA.

8. The composition of claim 1, wherein single-stranded nucleic acid is a cDNA.

9. The composition of claim 1, wherein the label is attached to the single-stranded nucleic acid and wherein the label is not an additional nucleic acid.

10. The composition of claim 1, wherein the single-stranded nucleic acid comprises a non-HIV-1 nucleotide sequence.

11. The composition of claim 1, wherein the single-stranded nucleic acid is chemically made at least in part.

12. The composition of claim 1, wherein the HIV-1 nucleic acid is a full-length HIV-1 nucleic acid.

13. The composition of claim 1, wherein the HIV-1 nucleic acid is not a full-length HIV-1 nucleic acid.

14. A method for preparing a DNA construct specific for Human Immunodeficiency Virus Type-1 (HIV-1) comprising the step of inserting into a vector a nucleic acid of at least 18 contiguous nucleotides comprising a nucleotide sequence selected from the group consisting of
   (i) a nucleotide sequence of either strand of viral DNA from lambda bacteriophage λ-HXB$_2$ having ATCC Accession No. 40231;
   (ii) a nucleotide sequence of either strand of viral DNA from lambda bacteriophage λ-HXB$_3$ having ATCC Accession No. 40232;
   (iii) a nucleotide sequence of either strand of viral DNA from clone BH10 having ATCC Accession No. 40125;
   (iv) a nucleotide sequence of either strand of viral DNA from clone BH5 having ATCC Accession No. 40126;
   (v) a nucleotide sequence of either strand of viral DNA from clone BH8 having ATCC Accession No. 40127;
   (vi) a nucleotide sequence of either strand of viral DNA from clone pHXB3 having ATCC Accession No. 67081;
   (vii) a nucleotide sequence of either strand of viral DNA from clone pHXB-2D having ATCC Accession No. 67082;
   (viii) a nucleotide sequence of either strand of viral DNA from *E. coli* clone X10-1 having ATCC Accession No. 67083; and
   (ix) an HIV-1 nucleotide sequence from the H9/HTLV-III cell line having ATCC Accession No. CRL 8543;
   whereby a DNA construct comprising an inserted nucleic acid is obtained.

15. The method according to claim 14, wherein the DNA construct permits making an RNA transcript of the inserted nucleic acid.

16. A method for replicating DNA specific for HIV-1 comprising the step of growing a cell containing the DNA construct of claim 14 under conditions whereby the inserted nucleic acid is replicated.

17. A method for producing a recombinant HIV-1 polypeptide comprising the step of growing a cell containing the DNA construct of claim 14 under conditions whereby the inserted nucleic acid is expressed to allow production of the recombinant HIV-1 polypeptide in the cell.

18. A nucleic acid of at least 18 contiguous nucleotides comprising a nucleotide sequence selected from the group consisting of
  (i) a nucleotide sequence of either strand of viral DNA from lambda bacteriophage λ-HXB$_2$ having ATCC Accession No. 40231;
  (ii) a nucleotide sequence of either strand of viral DNA from lambda bacteriophage λ-HXB$_3$ having ATCC Accession No. 40232;
  (iii) a nucleotide sequence of either strand of viral DNA from clone BH10 having ATCC Accession No. 40125;
  (iv) a nucleotide sequence of either strand of viral DNA from clone BH5 having ATCC Accession No. 40126;
  (v) a nucleotide sequence of either strand of viral DNA from clone BH8 having ATCC Accession No. 40127;
  (vi) a nucleotide sequence of either strand of viral DNA from clone pHXB3 having ATCC Accession No. 67081;
  (vii) a nucleotide sequence of either strand of viral DNA from clone pHXB-2D having ATCC Accession No. 67082;
  (viii) a nucleotide sequence of either strand of viral DNA from *E. coli* clone X10-1 having ATCC Accession No. 67083; and
  (ix) a Human Immunodeficiency Virus Type-1 (HIV-1) nucleotide sequence from the H9/HTLV-III cell line having ATCC Accession No. CRL 8543;
  wherein the nucleic acid does not form a duplex with HTLV-I and HTLV-II nucleic acids under conditions of stringency for hybridization under which the nucleic acid forms a duplex with an HIV-1 nucleic acid; and
  wherein the nucleic acid is covalently attached to a solid support.

19. The nucleic acid of claim 18, wherein the nucleic acid comprises a nucleotide sequence which is part of an HIV-1 gag open reading frame, an HIV-1 pol open reading frame, an HIV-1 env open reading frame or part of an HIV-1 long terminal repeat region.

20. The nucleic acid of claim 18, wherein the nucleic acid is selected from the group consisting of
  (i) a nucleic acid consisting of from 18 to 103 nucleotides comprising a nucleotide sequence of at least 18 contiguous nucleotides from an HIV-1 gag open reading frame, an HIV-1 pol open reading frame, an HIV-1 env open reading frame or from an HIV-1 long terminal repeat region;
  (ii) a nucleic acid consisting of from 32 to 103 nucleotides comprising a sequence of at least 32 contiguous nucleotides from an HIV-1 gag open reading frame, an HIV-1 pol open reading frame, an HIV-1 env open reading frame or from an HIV-1 long terminal repeat region;
  (iii) a nucleic acid consisting of from 20 to 100 nucleotides comprising a sequence of at least 20 contiguous nucleotides from an HIV-1 gag open reading frame, an HIV-1 pol open reading frame, an HIV-1 env open reading frame or from an HIV-1 long terminal repeat region;
  (iv) a nucleic acid comprising a sequence of at least about 32 contiguous nucleotides from an HIV-1 gag open reading frame, an HIV-1 pol open reading frame, an HIV-1 env open reading frame or from an HIV-1 long terminal repeat region; and
  (v) a nucleic acid comprising a sequence of at least about 20 contiguous nucleotides from an HIV-1 gag open reading frame, an HIV-1 pol open reading frame, an HIV-1 env open reading frame or from an HIV-1 long terminal repeat region.

21. The nucleic acid of claim 18, wherein the nucleic acid is a restriction fragment from an HIV-1 nucleic acid.

22. The nucleic acid of claim 18, wherein the nucleic acid is randomly generated from an HIV-1 nucleic acid.

23. The nucleic acid of claim 18, wherein the nucleic acid comprises DNA.

24. The nucleic acid of claim 18, wherein the nucleic acid comprises RNA.

25. The nucleic acid of claim 18, wherein the nucleic acid is a cDNA.

26. The nucleic acid of claim 18, wherein the nucleic acid comprises a label.

27. The nucleic acid of claim 18, wherein the nucleic acid comprises a non-HIV-1 nucleotide sequence.

28. The nucleic acid of claim 18, wherein the nucleic acid is chemically made at least in part.

29. The nucleic acid of claim 18, wherein the nucleic acid is a double-stranded nucleic acid.

30. The nucleic acid of claim 18, wherein the nucleic acid is a single-stranded nucleic acid.

31. A single-stranded nucleic acid of at least 18 contiguous nucleotides comprising a nucleotide sequence selected from the group consisting of
  (i) a nucleotide sequence of either strand of viral DNA from lambda bacteriophage λ-HXB$_2$ having ATCC Accession No. 40231;
  (ii) a nucleotide sequence of either strand of viral DNA from lambda bacteriophage λ-HXB$_3$ having ATCC Accession No. 40232;
  (iii) a nucleotide sequence of either strand of viral DNA from clone BH10 having ATCC Accession No. 40125;
  (iv) a nucleotide sequence of either strand of viral DNA from clone BH5 having ATCC Accession No. 40126;
  (v) a nucleotide sequence of either strand of viral DNA from clone BH8 having ATCC Accession No. 40127;
  (vi) a nucleotide sequence of either strand of viral DNA from clone pHXB3 having ATCC Accession No. 67081;
  (vii) a nucleotide sequence of either strand of viral DNA from clone pHXB-2D having ATCC Accession No. 67082;
  (viii) a nucleotide sequence of either strand of viral DNA from *E. coli* clone X10-1 having ATCC Accession No. 67083; and
  (ix) a Human Immunodeficiency Virus Type-1 (HIV-1) nucleotide sequence from the H9/HTLV-III cell line having ATCC Accession No. CRL 8543;
  wherein the single-stranded nucleic acid does not form a duplex with HTLV-I and HTLV-II nucleic acids under conditions of stringency for hybridization under which the single-stranded nucleic acid forms a duplex with an HIV-1 nucleic acid;
  wherein the single-stranded nucleic acid is within a duplex comprising the HIV-1 nucleic acid; and
  wherein the duplex is covalently attached to a solid support.

32. The single-stranded nucleic acid of claim 31, wherein the single-stranded nucleic acid is complementary to a sequence which is part of an HIV-1 gag open reading frame, an HIV-1 pol open reading frame, an HIV-1 env open reading frame or part of an HIV-1 long terminal repeat region.

33. The single-stranded nucleic acid of claim 31, wherein the single-stranded nucleic acid is selected from the group consisting of
   (i) a single-stranded nucleic acid consisting of from 18 to 103 nucleotides comprising a sequence of at least 18 contiguous nucleotides from an HIV-1 gag open reading frame, an HIV-1 pol open reading frame, an HIV-1 env open reading frame or from an HIV-1 long terminal repeat region;
   (ii) a single-stranded nucleic acid consisting of from 32 to 103 nucleotides comprising a sequence of at least 32 contiguous nucleotides from an HIV-1 gag open reading frame, an HIV-1 pol open reading frame, an HIV-1 env open reading frame or from an HIV-1 long terminal repeat region;
   (iii) a single-stranded nucleic acid consisting of from 20 to 100 nucleotides comprising a sequence of at least 20 contiguous nucleotides from an HIV-1 gag open reading frame, an HIV-1 pol open reading frame, an HIV-1 env open reading frame or from an HIV-1 long terminal repeat region;
   (iv) a single-stranded nucleic acid comprising a sequence of at least about 32 contiguous nucleotides from an HIV-1 gag open reading frame, an HIV-1 pol open reading frame, an HIV-1 env open reading frame or from an HIV-1 long terminal repeat region; and
   (v) a single-stranded nucleic acid comprising a sequence of at least about 20 contiguous nucleotides from an HIV-1 gag open reading frame, an HIV-1 pol open reading frame, an HIV-1 env open reading frame or from an HIV-1 long terminal repeat region.

34. The single-stranded nucleic acid of claim 31, wherein the HIV-1 nucleic acid is bound to a solid support.

35. The single-stranded nucleic acid of claim 31, wherein the single-stranded nucleic acid is randomly generated from an HIV-1 nucleic acid.

36. The single-stranded nucleic acid of claim 31, wherein the single-stranded nucleic acid comprises DNA.

37. The single-stranded nucleic acid of claim 31, wherein the single-stranded nucleic acid comprises RNA.

38. The single-stranded nucleic acid of claim 31, wherein the single-stranded nucleic acid is a cDNA.

39. The single-stranded nucleic acid of claim 31, wherein the single-stranded nucleic acid comprises a label.

40. The single-stranded nucleic acid of claim 31, wherein the single-stranded nucleic acid comprises a non-HIV-1 nucleotide sequence.

41. The single-stranded nucleic acid of claim 31, wherein the single-stranded nucleic acid is chemically made at least in part.

42. The single-stranded nucleic acid of claim 31, wherein the HIV-1 nucleic acid is a full-length HIV-1 nucleic acid.

43. The single-stranded nucleic acid of claim 31, wherein the HIV-1 nucleic acid is not a full-length HIV-1 nucleic acid.

44. A nucleic acid of at least 18 contiguous nucleotides comprising a nucleotide sequence selected from the group consisting of
   (i) a nucleotide sequence of either strand of viral DNA from lambda bacteriophage λ-HXB$_2$ having ATCC Accession No. 40231;
   (ii) a nucleotide sequence of either strand of viral DNA from lambda bacteriophage λ-HXB$_3$ having ATCC Accession No. 40232;
   (iii) a nucleotide sequence of either strand of viral DNA from clone BH10 having ATCC Accession No. 40125;
   (iv) a nucleotide sequence of either strand of viral DNA from clone BH5 having ATCC Accession No. 40126;
   (v) a nucleotide sequence of either strand of viral DNA from clone BH8 having ATCC Accession No. 40127;
   (vi) a nucleotide sequence of either strand of viral DNA from clone pHXB3 having ATCC Accession No. 67081;
   (vii) a nucleotide sequence of either strand of viral DNA from clone pHXB-2D having ATCC Accession No. 67082;
   (viii) a nucleotide sequence of either strand of viral DNA from *E. coli* clone X10-1 having ATCC Accession No. 67083; and
   (ix) a Human Immunodeficiency Virus Type-1 (HIV-1) nucleotide sequence from the H9/HTLV-III cell line having ATCC Accession No. CRL 8543;
   wherein the nucleic acid does not form a duplex with HTLV-I and HTLV-II nucleic acids under conditions of stringency for hybridization under which the nucleic acid forms a duplex with an HIV-1 nucleic acid;
   wherein the nucleic acid comprises a detectable label covalently attached to the nucleic acid; and
   wherein the detectable label is not an additional nucleic acid.

45. The nucleic acid of claim 44, wherein the nucleic acid comprises a nucleotide sequence which is part of an HIV-1 gag open reading frame, an HIV-1 pol open reading frame, an HIV-1 env open reading frame or part of an HIV-1 long terminal repeat region.

46. The nucleic acid of claim 44, wherein the nucleic acid is selected from the group consisting of
   (i) a nucleic acid consisting of from 18 to 103 nucleotides comprising a sequence of at least 18 contiguous nucleotides from an HIV-1 gag open reading frame, an HIV-1 pol open reading frame, an HIV-1 env open reading frame or from an HIV-1 long terminal repeat region;
   (ii) a nucleic acid consisting of from 32 to 103 nucleotides comprising a sequence of at least 32 contiguous nucleotides from an HIV-1 gag open reading frame, an HIV-1 pol open reading frame, an HIV-1 env open reading frame or from an HIV-1 long terminal repeat region;
   (iii) a nucleic acid consisting of from 20 to 100 nucleotides comprising a sequence of at least 20 contiguous nucleotides from an HIV-1 gag open reading frame, an HIV-1 pol open reading frame, an HIV-1 env open reading frame or from an HIV-1 long terminal repeat region;
   (iv) a nucleic acid comprising a sequence of at least about 32 contiguous nucleotides from an HIV-1 gag open reading frame, an HIV-1 pol open reading frame, an HIV-1 env open reading frame or from an HIV-1 long terminal repeat region n; and
   (v) a nucleic acid comprising a sequence of at least about 20 contiguous nucleotides from an HIV-1 gag open reading frame, an HIV-1 pol open reading frame, an HIV-1 env open reading frame or from an HIV-1 long terminal repeat region.

47. The nucleic acid of claim 44, wherein the nucleic acid is a restriction fragment from an HIV-1 nucleic acid.

48. The nucleic acid of claim 44, wherein the nucleic acid is randomly generated from an HIV-1 nucleic acid.

49. The nucleic acid of claim 44, wherein the nucleic acid comprises DNA.

50. The nucleic acid of claim 44, wherein the nucleic acid comprises RNA.

51. The nucleic acid of claim 44, wherein the nucleic acid is a cDNA.

52. The nucleic acid of claim 44, wherein the nucleic acid comprises a non-HIV-1 nucleotide sequence.

53. The nucleic acid of claim 44, wherein the nucleic acid is chemically made at least in part.

54. The nucleic acid of claim 44, wherein the nucleic acid is a double-stranded nucleic acid.

55. The nucleic acid of claim 44, wherein the nucleic acid is a single-stranded nucleic acid.

56. A nucleic acid of at least 18 contiguous nucleotides comprising a nucleotide sequence selected from the group consisting of
 (i) a nucleotide sequence of either strand of viral DNA from lambda bacteriophage λ-HXB$_2$ having ATCC Accession No. 40231;
 (ii) a nucleotide sequence of either strand of viral DNA from lambda bacteriophage λ-HXB$_3$ having ATCC Accession No. 40232;
 (iii) a nucleotide sequence of either strand of viral DNA from clone BH10 having ATCC Accession No. 40125;
 (iv) a nucleotide sequence of either strand of viral DNA from clone BH5 having ATCC Accession No. 40126;
 (v) a nucleotide sequence of either strand of viral DNA from clone BH8 having ATCC Accession No. 40127;
 (vi) a nucleotide sequence of either strand of viral DNA from clone pHXB3 having ATCC Accession No. 67081;
 (vii) a nucleotide sequence of either strand of viral DNA from clone pHXB-2D having ATCC Accession No. 67082;
 (viii) a nucleotide sequence of either strand of viral DNA from *E. coli* clone X10-1 having ATCC Accession No. 67083; and
 (ix) a Human Immunodeficiency Virus Type-1 (HIV-1) nucleotide sequence from the H9/HTLV-III cell line having ATCC Accession No. CRL 8543;
 wherein the nucleic acid does not form a duplex with HTLV-I and HTLV-II nucleic acids under conditions of stringency for hybridization under which the nucleic acid forms a duplex with an HIV-1 nucleic acid;
 wherein the nucleic acid is outside of a mammalian cell and outside of a viral particle; and
 wherein the nucleic acid is attached to a non-HIV-1 nucleic acid through a covalent bond.

57. The nucleic acid of claim 56, wherein the nucleic acid is complementary to a sequence which is part of an HIV-1 gag open reading frame, an HIV-1 pol open reading frame, an HIV-1 env open reading frame or part of an HIV-1 long terminal repeat region.

58. The nucleic acid of claim 56, wherein the nucleic acid is selected from the group consisting of
 (i) a nucleic acid consisting of from 18 to 103 nucleotides comprising a sequence of at least 18 contiguous nucleotides from an HIV-1 gag open reading frame, an HIV-1 pol open reading frame, an HIV-1 env open reading frame or from an HIV-1 long terminal repeat region;
 (ii) a nucleic acid consisting of from 32 to 103 nucleotides comprising a sequence of at least 32 contiguous nucleotides from an HIV-1 gag open reading frame, an HIV-1 pol open reading frame, an HIV-1 env open reading frame or from an HIV-1 long terminal repeat region;
 (iii) a nucleic acid consisting of from 20 to 100 nucleotides comprising a sequence of at least 20 contiguous nucleotides from an HIV-1 gag open reading frame, an HIV-1 pol open reading frame, an HIV-1 env open reading frame or from an HIV-1 long terminal repeat region;
 (iv) a nucleic acid comprising a sequence of at least about 32 contiguous nucleotides from an HIV-1 gag open reading frame, an HIV-1 pol open reading frame, an HIV-1 env open reading frame or from an HIV-1 long terminal repeat region; and
 (v) a nucleic acid comprising a sequence of at least about 20 contiguous nucleotides from an HIV-1 gag open reading frame, an HIV-1 pol open reading frame, an HIV-1 env open reading frame or from an HIV-1 long terminal repeat region.

59. The nucleic acid of claim 56, wherein the nucleic acid is a restriction fragment from an HIV-1 nucleic acid.

60. The nucleic acid of claim 56, wherein the nucleic acid is randomly generated from an HIV-1 nucleic acid.

61. The nucleic acid of claim 56, wherein the nucleic acid comprises DNA.

62. The nucleic acid of claim 56, wherein the nucleic acid comprises RNA.

63. The nucleic acid of claim 56, wherein the nucleic acid is a cDNA.

64. The nucleic acid of claim 56, wherein the nucleic acid comprises a label.

65. The nucleic acid of claim 56, wherein the nucleic acid is chemically made at least in part.

66. The nucleic acid of claim 56, wherein the nucleic acid is a double-stranded nucleic acid.

67. The nucleic acid of claim 56, wherein the nucleic acid is a single-stranded nucleic acid.

68. A composition comprising a duplex formed between:
 (A) a single-stranded nucleic acid of between 18 and 103 contiguous nucleotides and comprising a nucleotide sequence selected from the group consisting of:
  (i) a nucleotide sequence of either strand of viral DNA from lambda bacteriophage λ-HXB$_2$ having ATCC Accession No. 40231;
  (ii) a nucleotide sequence of either strand of viral DNA from lambda bacteriophage λ-HXB$_3$ having ATCC Accession No. 40232;
  (iii) a nucleotide sequence of either strand of viral DNA from clone BH10 having ATCC Accession No. 40125;
  (iv) a nucleotide sequence of either strand of viral DNA from clone BH5 having ATCC Accession No. 40126;
  (v) a nucleotide sequence of either strand of viral DNA from clone BH8 having ATCC Accession No. 40127;
  (vi) a nucleotide sequence of either strand of viral DNA from clone pHXB3 having ATCC Accession No. 67081;
  (vii) a nucleotide sequence of either strand of viral DNA from clone pHXB-2D having ATCC Accession No. 67082;
  (viii) a nucleotide sequence of either strand of viral DNA from *E. coli* clone X10-1 having ATCC Accession No. 67083; and
  (ix) a Human Immunodeficiency Virus Type-1 (HIV-1) nucleotide sequence from the H9/HTLV-III cell line having ATCC Accession No. CRL 8543; and
 (B) an HIV-1 nucleic acid selected from the group consisting of:
  (a) an HIV-1 nucleic acid comprising a nucleotide sequence encoding a full-length gag polypeptide or its complement;
  (b) an HIV-1 nucleic acid comprising a nucleotide sequence encoding a full-length pol polypeptide or its complement;
  (c) an HIV-1 nucleic acid comprising a nucleotide sequence encoding a full-length env polypeptide or its complement; and
  (d) an HIV-1 nucleic acid comprising a nucleotide sequence for a long terminal repeat region comprising R and U$_3$ regions or their complements;
 wherein the single-stranded nucleic acid of (A) does not form a duplex with HTLV-I and HTLV-II nucleic acids under conditions of stringency for hybridization under which the nucleic acid of (A) forms a duplex with the HIV-1 nucleic acid of (B);

wherein the duplex is outside of a mammalian cell and outside of a viral particle;

wherein the duplex comprises a double-stranded region of between 18 and 103 contiguous nucleotides and a single-stranded region on either side of the double-stranded region that is longer than the double-stranded region; and wherein the single-stranded nucleic acid comprises a label.

69. The composition of claim 68, wherein the single-stranded nucleic acid comprises a nucleotide sequence which is part of an HIV-1 gag open reading frame, an HIV-1 pol open reading frame, an HIV-1 env open reading frame or part of an HIV-1 long terminal repeat region.

70. The composition of claim 68, wherein the single-stranded nucleic acid is selected from the group consisting of
  (i) a single-stranded nucleic acid consisting of from 18 to 103 nucleotides comprising a sequence of at least 18 contiguous nucleotides from an HIV-1 gag open reading frame, an HIV-1 pol open reading frame, an HIV-1 env open reading frame or from an HIV-1 long terminal repeat region;
  (ii) a single-stranded nucleic acid consisting of from 32 to 103 nucleotides comprising a sequence of at least 32 contiguous nucleotides from an HIV-1 gag open reading frame, an HIV-1 pol open reading frame, an HIV-1 env open reading frame or from an HIV-1 long terminal repeat region;
  (iii) a single-stranded nucleic acid consisting of from 20 to 100 nucleotides comprising a sequence of at least 20 contiguous nucleotides from an HIV-1 gag open reading frame, an HIV-1 pol open reading frame, an HIV-1 env open reading frame or from an HIV-1 long terminal repeat region;
  (iv) a single-stranded nucleic acid comprising a sequence of at least about 32 contiguous nucleotides from an HIV-1 gag open reading frame, an HIV-1 pol open reading frame, an HIV-1 env open reading frame or from an HIV-1 long terminal repeat region; and
  (v) a single-stranded nucleic acid comprising a sequence of at least about 20 contiguous nucleotides from an HIV-1 gag open reading frame, an HIV-1 pol open reading frame, an HIV-1 env open reading frame or from an HIV-1 long terminal repeat region.

71. The composition of claim 68, wherein the single-stranded nucleic acid is randomly generated from an HIV-1 nucleic acid.

72. The composition of claim 68, wherein the single-stranded nucleic acid comprises DNA.

73. The composition of claim 68, wherein the single-stranded nucleic acid comprises RNA.

74. The composition of claim 68, wherein the single-stranded nucleic acid is a cDNA.

75. The composition of claim 68, wherein the label is attached to the single-stranded nucleic acid and wherein the label is not an additional nucleic acid.

76. The composition of claim 68, wherein the single-stranded nucleic acid comprises a non-HIV-1 nucleotide sequence.

77. The composition of claim 68, wherein the single-stranded nucleic acid is chemically made at least in part.

78. The composition of claim 68, wherein the single-stranded nucleic acid is bound to a solid support.

79. The composition of claim 68, wherein the duplex is bound to a solid support.

80. The composition of claim 68, wherein the HIV-1 nucleic acid is a full-length HIV-1 nucleic acid.

81. The composition of claim 68, wherein the HIV-1 nucleic acid is not a full-length HIV-1 nucleic acid.

82. A composition comprising:
  (A) a duplex; and
  (B) a compound selected from the group consisting of sodium saline citrate, formamide, and dextran sulfate;
    wherein the duplex comprises a Human Immunodeficiency Virus Type-1 (HIV-1) nucleic acid having a length of at least 300 nucleotides hybridized to a single-stranded nucleic acid of between 18 and 103 contiguous nucleotides and comprising a nucleotide sequence selected from the group consisting of:
  (i) a nucleotide sequence of either strand of viral DNA from lambda bacteriophage $\lambda$-HXB$_2$ having ATCC Accession No. 40231;
  (ii) a nucleotide sequence of either strand of viral DNA from lambda bacteriophage $\lambda$-HXB$_3$ having ATCC Accession No. 40232;
  (iii) a nucleotide sequence of either strand of viral DNA from clone BH10 having ATCC Accession No. 40125;
  (iv) a nucleotide sequence of either strand of viral DNA from clone BH5 having ATCC Accession No. 40126;
  (v) a nucleotide sequence of either strand of viral DNA from clone BH8 having ATCC Accession No. 40127;
  (vi) a nucleotide sequence of either strand of viral DNA from clone pHXB3 having ATCC Accession No. 67081;
  (vii) a nucleotide sequence of either strand of viral DNA from clone pHXB-2D having ATCC Accession No. 67082;
  (viii) a nucleotide sequence of either strand of viral DNA from *E. coli* clone X10-1 having ATCC Accession No. 67083; and
  (ix) a Human Immunodeficiency Virus Type-1 (HIV-1) nucleotide sequence from the H9/HTLV-III cell line having ATCC Accession No. CRL 8543;
  wherein the single-stranded nucleic acid does not form a duplex with HTLV-I and HTLV-II nucleic acids under conditions of stringency for hybridization under which the single-stranded nucleic acid forms a duplex with the HIV-1 nucleic acid; and
  wherein the duplex comprises a double-stranded region and a single-stranded region that is longer than the double-stranded region.

83. The composition of claim 82, wherein the single-stranded nucleic acid comprises a sequence which is part of an HIV-1 gag open reading frame, an HIV-1 pol open reading frame, an HIV-1 env open reading frame or part of an HIV-1 long terminal repeat region.

84. The composition of claim 82, wherein the single-stranded nucleic acid is selected from the group consisting of
  (i) a single-stranded nucleic acid consisting of from 18 to 103 nucleotides comprising a sequence of at least 18 contiguous nucleotides from an HIV-1 gag open reading frame, an HIV-1 pol open reading frame, an HIV-1 env open reading frame or from an HIV-1 long terminal repeat region;
  (ii) a single-stranded nucleic acid consisting of from 32 to 103 nucleotides comprising a sequence of at least 32 contiguous nucleotides from an HIV-1 gag open reading frame, an HIV-1 pol open reading frame, an HIV-1 env open reading frame or from an HIV-1 long terminal repeat region;
  (iii) a single-stranded nucleic acid consisting of from 20 to 100 nucleotides comprising a sequence of at least 20 contiguous nucleotides from an HIV-1 gag open reading frame, an HIV-1 pol open reading frame, an HIV-1 env open reading frame or from an HIV-1 long terminal repeat region;
(iv) a single-stranded nucleic acid comprising a sequence of at least about 32 contiguous nucleotides from an HIV-1 gag open reading frame, an HIV-1 pol open reading frame, an HIV-1 env open reading frame or from an HIV-1 long terminal repeat region; and
(v) a single-stranded nucleic acid comprising a sequence of at least about 20 contiguous nucleotides from an HIV-1 gag open reading frame, an HIV-1 pol open reading frame, an HIV-1 env open reading frame or from an HIV-1 long terminal repeat region.

85. The composition of claim 82, wherein the single-stranded nucleic acid is randomly generated from an HIV-1 nucleic acid.

86. The composition of claim 82, wherein the single-stranded nucleic acid comprises DNA.

87. The composition of claim 82, wherein the single-stranded nucleic acid comprises RNA.

88. The composition of claim 82, wherein the single-stranded nucleic acid is a cDNA.

89. The composition of claim 82, wherein the single-stranded nucleic acid comprises a label.

90. The composition of claim 82, wherein the single-stranded nucleic acid comprises a non-HIV-1 nucleotide sequence.

91. The composition of claim 82, wherein the single-stranded nucleic acid is chemically made at least in part.

92. The composition of claim 82, wherein the single-stranded nucleic acid is bound to a solid support.

93. The composition of claim 82, wherein the duplex is bound to a solid support.

94. The composition of claim 82, wherein the HIV-1 nucleic acid is a full-length HIV-1 nucleic acid.

95. The composition of claim 82, wherein the HIV-1 nucleic acid is not a full-length HIV-1 nucleic acid.

96. A composition comprising a duplex formed between a Human Immunodeficiency Virus Type-1 (HIV-1) nucleic acid and a single-stranded nucleic acid of at least 18 contiguous nucleotides and comprising a nucleotide sequence selected from the group consisting of:
(i) a nucleotide sequence of either strand of viral DNA from lambda bacteriophage λ-HXB$_2$ having ATCC Accession No. 40231;
(ii) a nucleotide sequence of either strand of viral DNA from lambda bacteriophage λ-HXB$_3$ having ATCC Accession No. 40232;
(iii) a nucleotide sequence of either strand of viral DNA from clone BH10 having ATCC Accession No. 40125;
(iv) a nucleotide sequence of either strand of viral DNA from clone BH5 having ATCC Accession No. 40126;
(v) a nucleotide sequence of either strand of viral DNA from clone BH8 having ATCC Accession No. 40127;
(vi) a nucleotide sequence of either strand of viral DNA from clone pHXB3 having ATCC Accession No. 67081;
(vii) a nucleotide sequence of either strand of viral DNA from clone pHXB-2D having ATCC Accession No. 67082;
(viii) a nucleotide sequence of either strand of viral DNA from *E. coli* clone X10-1 having ATCC Accession No. 67083; and
(ix) an HIV-1 nucleotide sequence from the H9/HTLV-III cell line having ATCC Accession No. CRL 8543;
wherein the single-stranded nucleic acid does not form a duplex with HTLV-I and HTLV-II nucleic acids under conditions of stringency for hybridization under which the single-stranded nucleic acid forms a duplex with the HIV-1 nucleic acid;
wherein the single-stranded nucleic acid consists of DNA;
wherein the duplex is outside of a mammalian cell;
wherein the duplex comprises a double-stranded region of at least 18 contiguous nucleotides and a single-stranded region on either side of the double-stranded region that is longer than the double-stranded region; and
wherein the duplex is bound to a solid support.

97. The composition of claim 96, wherein the single-stranded nucleic acid comprises a nucleotide sequence which is part of an HIV-1 gag open reading frame, an HIV-1 pol open reading frame, an HIV-1 env open reading frame or part of an HIV-1 long terminal repeat region.

98. The composition of claim 96, wherein the single-stranded nucleic acid is selected from the group consisting of:
(i) a single-stranded nucleic acid consisting of from 18 to 103 nucleotides comprising a nucleotide sequence of at least 18 contiguous nucleotides from an HIV-1 gag open reading frame, an HIV-1 env open reading frame, an HIV-1 pol open reading frame or from an HIV-1 long terminal repeat region;
(ii) a single-stranded nucleic acid consisting of from 32 to 103 nucleotides comprising a nucleotide sequence of at least 32 contiguous nucleotides from an HIV-1 gag open reading frame, an HIV-1 env open reading frame, an HIV-1 pol open reading frame or from an HIV-1 long terminal repeat region;
(iii) a single-stranded nucleic acid consisting of from 20 to 100 nucleotides comprising a nucleotide sequence of at least 20 contiguous nucleotides from an HIV-1 gag open reading frame, an HIV-1 env open reading frame, an HIV-1 pol open reading frame or from an HIV-1 long terminal repeat region;
(iv) a single-stranded nucleic acid comprising a nucleotide sequence of at least about 32 contiguous nucleotides from an HIV-1 gag open reading frame, an HIV-1 env open reading frame, an HIV-1 pol open reading frame or from an HIV-1 long terminal repeat region; and
(v) a single-stranded nucleic acid comprising a nucleotide sequence of at least about 20 contiguous nucleotides from an HIV-1 gag open reading frame, an HIV-1 env open reading frame, an HIV-1 pol open reading frame or from an HIV-1 long terminal repeat region.

99. The composition of claim 96, further comprising a compound selected from the group consisting of sodium saline citrate, formamide, and dextran sulfate.

100. The composition of claim 96, wherein the single-stranded nucleic acid is randomly generated from an HIV-1 nucleic acid.

101. The composition of claim 96, wherein the single-stranded nucleic acid comprises a label.

102. The composition of claim 96, wherein the single-stranded nucleic acid comprises a non-HIV-1 DNA nucleotide sequence.

103. The composition of claim 96, wherein the single-stranded nucleic acid is chemically made at least in part.

104. The composition of claim 96, wherein the HIV-1 nucleic acid is a full-length HIV-1 nucleic acid.

105. The composition of claim 96, wherein the HIV-1 nucleic acid is not a full-length HIV-1 nucleic acid.

106. A single-stranded nucleic acid of at least 18 contiguous nucleotides comprising a nucleotide sequence selected from the group consisting of:

(i) a nucleotide sequence of either strand of viral DNA from lambda bacteriophage λ-HXB$_2$ having ATCC Accession No. 40231;
(ii) a nucleotide sequence of either strand of viral DNA from lambda bacteriophage λ-HXB$_3$ having ATCC Accession No. 40232;
(iii) a nucleotide sequence of either strand of viral DNA from clone BH10 having ATCC Accession No. 40125;
(iv) a nucleotide sequence of either strand of viral DNA from clone BH5 having ATCC Accession No. 40126;
(v) a nucleotide sequence of either strand of viral DNA from clone BH8 having ATCC Accession No. 40127;
(vi) a nucleotide sequence of either strand of viral DNA from clone pHXB3 having ATCC Accession No. 67081;
(vii) a nucleotide sequence of either strand of viral DNA from clone pHXB-2D having ATCC Accession No. 67082;
(viii) a nucleotide sequence of either strand of viral DNA from *E. coli* clone X10-1 having ATCC Accession No. 67083; and
(ix) a Human Immunodeficiency Virus Type-1 (HIV-1) nucleotide sequence from the H9/HTLV-III cell line having ATCC Accession No. CRL 8543;
wherein the single-stranded nucleic acid does not form a duplex with HTLV-I and HTLV-II nucleic acids under conditions of stringency for hybridization under which the single-stranded nucleic acid forms a duplex with an HIV-1 nucleic acid;
wherein the single-stranded nucleic acid is outside of a mammalian cell and outside of a viral particle;
wherein the single-stranded nucleic acid consists of DNA; and
wherein the single-stranded nucleic acid is attached to a non-HIV-1 DNA nucleic acid through a covalent bond.

107. The single-stranded nucleic acid of claim 106, wherein the nucleic acid is complementary to a sequence which is part of an HIV-1 gag open reading frame, an HIV-1 pol open reading frame, an HIV-1 env open reading frame or part of an HIV-1 long terminal repeat region.

108. The single-stranded nucleic acid of claim 106, wherein the single-stranded nucleic acid is selected from the group consisting of
(i) a single-stranded nucleic acid consisting of from 18 to 103 nucleotides comprising a sequence of at least 18 contiguous nucleotides from an HIV-1 gag open reading frame, an HIV-1 pol open reading frame, an HIV-1 env open reading frame or from an HIV-1 long terminal repeat region;
(ii) a single-stranded nucleic acid consisting of from 32 to 103 nucleotides comprising a sequence of at least 32 contiguous nucleotides from an HIV-1 gag open reading frame, an HIV-1 pol open reading frame, an HIV-1 env open reading frame or from an HIV-1 long terminal repeat region;
(iii) a single-stranded nucleic acid consisting of from 20 to 100 nucleotides comprising a sequence of at least 20 contiguous nucleotides from an HIV-1 gag open reading frame, an HIV-1 pol open reading frame, an HIV-1 env open reading frame or from an HIV-1 long terminal repeat region;
(iv) a single-stranded nucleic acid comprising a sequence of at least about 32 contiguous nucleotides from an HIV-1 gag open reading frame, an HIV-1 pol open reading frame, an HIV-1 env open reading frame or from an HIV-1 long terminal repeat region; and
(v) a single-stranded nucleic acid comprising a sequence of at least about 20 contiguous nucleotides from an HIV-1 gag open reading frame, an HIV-1 pol open reading frame, an HIV-1 env open reading frame or from an HIV-1 long terminal repeat region.

109. The single-stranded nucleic acid of claim 106, wherein the single-stranded nucleic acid is randomly generated from an HIV-1 nucleic acid.

110. The single-stranded nucleic acid of claim 106, wherein the single-stranded nucleic acid comprises a label.

111. The single-stranded nucleic acid of claim 106, wherein the single-stranded nucleic acid is chemically made at least in part.

112. A composition comprising a duplex formed between:
(A) a single-stranded nucleic acid of between 18 and 103 contiguous nucleotides and comprising a nucleotide sequence selected from the group consisting of:
(i) a nucleotide sequence of either strand of viral DNA from lambda bacteriophage λ-HXB$_2$ having ATCC Accession No. 40231;
(ii) a nucleotide sequence of either strand of viral DNA from lambda bacteriophage λ-HXB$_3$ having ATCC Accession No. 40232;
(iii) a nucleotide sequence of either strand of viral DNA from clone BH10 having ATCC Accession No. 40125;
(iv) a nucleotide sequence of either strand of viral DNA from clone BH5 having ATCC Accession No. 40126;
(v) a nucleotide sequence of either strand of viral DNA from clone BH8 having ATCC Accession No. 40127;
(vi) a nucleotide sequence of either strand of viral DNA from clone pHXB3 having ATCC Accession No. 67081;
(vii) a nucleotide sequence of either strand of viral DNA from clone pHXB-2D having ATCC Accession No. 67082;
(viii) a nucleotide sequence of either strand of viral DNA from *E. coli* clone X10-1 having ATCC Accession No. 67083; and
(ix) a Human Immunodeficiency Virus Type-1 (HIV-1) nucleotide sequence from the H9/HTLV-III cell line having ATCC Accession No. CRL 8543; and
(B) an HIV-1 nucleic acid selected from the group consisting of:
(a) an HIV-1 nucleic acid comprising a nucleotide sequence encoding a full-length gag polypeptide or its complement;
(b) an HIV-1 nucleic acid comprising a nucleotide sequence encoding a full-length pol polypeptide or its complement;
(c) an HIV-1 nucleic acid comprising a nucleotide sequence encoding a full-length env polypeptide or its complement; and
(d) an HIV-1 nucleic acid comprising a nucleotide sequence for a long terminal repeat region comprising R and U$_3$ regions or their complements;
wherein the single-stranded nucleic acid of (A) does not form a duplex with HTLV-I and HTLV-II nucleic acids under conditions of stringency for hybridization under which the single-stranded nucleic acid of (A) forms a duplex with the HIV-1 nucleic acid of (B);
wherein the single-stranded nucleic acid of (A) consists of DNA;
wherein the duplex is outside of a mammalian cell and outside of a viral particle;
wherein the duplex comprises a double-stranded region of between 18 and 103 contiguous nucleotides and a single-stranded region on either side of the double-stranded region that is longer than the double-stranded region; and wherein either the single-stranded nucleic acid or the duplex is bound to a solid support.

113. The composition of claim 112, wherein the single-stranded nucleic acid comprises a nucleotide sequence which is part of an HIV-1 gag open reading frame, an HIV-1 pol open reading frame, an HIV-1 env open reading frame or part of an HIV-1 long terminal repeat region.

114. The composition of claim 112, wherein the single-stranded nucleic acid is selected from the group consisting of
   (i) a single-stranded nucleic acid consisting of from 18 to 103 nucleotides comprising a sequence of at least 18 contiguous nucleotides from an HIV-1 gag open reading frame, an HIV-1 pol open reading frame, an HIV-1 env open reading frame or from an HIV-1 long terminal repeat region;
   (ii) a single-stranded nucleic acid consisting of from 32 to 103 nucleotides comprising a sequence of at least 32 contiguous nucleotides from an HIV-1 gag open reading frame, an HIV-1 pol open reading frame, an HIV-1 env open reading frame or from an HIV-1 long terminal repeat region;
   (iii) a single-stranded nucleic acid consisting of from 20 to 100 nucleotides comprising a sequence of at least 20 contiguous nucleotides from an HIV-1 gag open reading frame, an HIV-1 pol open reading frame, an HIV-1 env open reading frame or from an HIV-1 long terminal repeat region;
   (iv) a single-stranded nucleic acid comprising a sequence of at least about 32 contiguous nucleotides from an HIV-1 gag open reading frame, an HIV-1 pol open reading frame, an HIV-1 env open reading frame or from an HIV-1 long terminal repeat region; and
   (v) a single-stranded nucleic acid comprising a sequence of at least about 20 contiguous nucleotides from an HIV-1 gag open reading frame, an HIV-1 pol open reading frame, an HIV-1 env open reading frame or from an HIV-1 long terminal repeat region.

115. The composition of claim 112, wherein the single-stranded nucleic acid is randomly generated from an HIV-1 nucleic acid.

116. The composition of claim 112, wherein the single-stranded nucleic acid comprises a label.

117. The composition of claim 112, wherein the single-stranded nucleic acid comprises a non-HIV-1 DNA nucleotide sequence.

118. The composition of claim 112, wherein the single-stranded nucleic acid is chemically made at least in part.

119. The composition of claim 112, wherein the single-stranded nucleic acid is bound to the solid support.

120. The composition of claim 112, wherein the duplex is bound to the solid support.

121. The composition of claim 112, wherein the HIV-1 nucleic acid is a full-length HIV-1 nucleic acid.

122. The composition of claim 112, wherein the HIV-1 nucleic acid is not a full-length HIV-1 nucleic acid.

123. A composition comprising:
   (A) a single-stranded nucleic acid of between 18 and 103 contiguous nucleotides and comprising a nucleotide sequence selected from the group consisting of:
      (i) a nucleotide sequence of either strand of viral DNA from lambda bacteriophage λ-HXB$_2$ having ATCC Accession No. 40231;
      (ii) a nucleotide sequence of either strand of viral DNA from lambda bacteriophage λ-HXB$_3$ having ATCC Accession No. 40232;
      (iii) a nucleotide sequence of either strand of viral DNA from clone BH10 having ATCC Accession No. 40125;
      (iv) a nucleotide sequence of either strand of viral DNA from clone BH5 having ATCC Accession No. 40126;
      (v) a nucleotide sequence of either strand of viral DNA from clone BH8 having ATCC Accession No. 40127;
      (vi) a nucleotide sequence of either strand of viral DNA from clone pHXB3 having ATCC Accession No. 67081;
      (vii) a nucleotide sequence of either strand of viral DNA from clone pHXB-2D having ATCC Accession No. 67082;
      (viii) a nucleotide sequence of either strand of viral DNA from *E. coli* clone X10-1 having ATCC Accession No. 67083; and
      (ix) a Human Immunodeficiency Virus Type-1 (HIV-1) nucleotide sequence from the H9/HTLV-III cell line having ATCC Accession No. CRL 8543; and
   (B) a compound selected from the group consisting of sodium saline citrate, formamide, and dextran sulfate;
   wherein the single-stranded nucleic acid does not form a duplex with HTLV-I and HTLV-II nucleic acids under conditions of stringency for hybridization under which the single-stranded nucleic acid forms a duplex with an HIV-1 nucleic acid.

124. The composition of claim 123, wherein the single-stranded nucleic acid comprises a sequence which is part of an HIV-1 gag open reading frame, an HIV-1 pol open reading frame, an HIV-1 env open reading frame or part of an HIV-1 long terminal repeat region.

125. The composition of claim 123, wherein the single-stranded nucleic acid is selected from the group consisting of:
   (i) a single-stranded nucleic acid consisting of from 18 to 103 nucleotides comprising a sequence of at least 18 contiguous nucleotides from an HIV-1 gag open reading frame, an HIV-1 pol open reading frame, an HIV-1 env open reading frame or from an HIV-1 long terminal repeat region;
   (ii) a single-stranded nucleic acid consisting of from 32 to 103 nucleotides comprising a sequence of at least 32 contiguous nucleotides from an HIV-1 gag open reading frame, an HIV-1 pol open reading frame, an HIV-1 env open reading frame or from an HIV-1 long terminal repeat region;
   (iii) a single-stranded nucleic acid consisting of from 20 to 100 nucleotides comprising a sequence of at least 20 contiguous nucleotides from an HIV-1 gag open reading frame, an HIV-1 pol open reading frame, an HIV-1 env open reading frame or from an HIV-1 long terminal repeat region;
   (iv) a single-stranded nucleic acid comprising a sequence of at least about 32 contiguous nucleotides from an HIV-1 gag open reading frame, an HIV-1 pol open reading frame, an HIV-1 env open reading frame or from an HIV-1 long terminal repeat region; and
   (v) a single-stranded nucleic acid comprising a sequence of at least about 20 contiguous nucleotides from an HIV-1 gag open reading frame, an HIV-1 pol open reading frame, an HIV-1 env open reading frame or from an HIV-1 long terminal repeat region.

126. The composition of claim 123, wherein the single-stranded nucleic acid is randomly generated from an HIV-1 nucleic acid.

127. The composition of claim 123, wherein the single-stranded nucleic acid comprises DNA.

128. The composition of claim 123, wherein the single-stranded nucleic acid comprises RNA.

129. The composition of claim 123, wherein the single-stranded nucleic acid is a cDNA.

130. The composition of claim 123, wherein the single-stranded nucleic acid comprises a label.

131. The composition of claim 123, wherein the single-stranded nucleic acid comprises a non-HIV-1 nucleotide sequence.

132. The composition of claim 123, wherein the single-stranded nucleic acid is chemically made at least in part.

133. The composition of claim 123, wherein the single-stranded nucleic acid is bound to a solid support.

134. A composition comprising a duplex formed between a Human Immunodeficiency Virus Type-1 (HIV-1) nucleic acid and a single-stranded nucleic acid comprising a nucleotide sequence selected from the group consisting of:
   (i) a nucleotide sequence of either strand of viral DNA from lambda bacteriophage λ-HXB$_2$ having ATCC Accession No. 40231;
   (ii) a nucleotide sequence of either strand of viral DNA from lambda bacteriophage λ-HXB$_3$ having ATCC Accession No. 40232;
   (iii) a nucleotide sequence of either strand of viral DNA from clone BH10 having ATCC Accession No. 40125;
   (iv) a nucleotide sequence of either strand of viral DNA from clone BH5 having ATCC Accession No. 40126;
   (v) a nucleotide sequence of either strand of viral DNA from clone BH8 having ATCC Accession No. 40127;
   (vi) a nucleotide sequence of either strand of viral DNA from clone pHXB3 having ATCC Accession No. 67081;
   (vii) a nucleotide sequence of either strand of viral DNA from clone pHXB-2D having ATCC Accession No. 67082;
   (viii) a nucleotide sequence of either strand of viral DNA from *E. coli* clone X10-1 having ATCC Accession No. 67083; and
   (ix) an HIV-1 nucleotide sequence from the H9/HTLV-III cell line having ATCC Accession No. CRL 8543;
      wherein the single-stranded nucleic acid does not form a duplex with HTLV-I and HTLV-II nucleic acids under conditions of stringency for hybridization under which the single-stranded nucleic acid forms a duplex with the HIV-1 nucleic acid;
      wherein the duplex is outside of a mammalian cell and outside of an HIV-1 particle;
      wherein the duplex comprises a double-stranded region and a single-stranded region on either side of the double-stranded region that is longer than the double-stranded region; and
      wherein the single-stranded nucleic acid comprises a label.

135. The composition of claim 134, wherein the single-stranded nucleic acid comprises a nucleotide sequence which is part of an HIV-1 gag open reading frame, an HIV-1 pol open reading frame, an HIV-1 env open reading frame or part of an HIV-1 long terminal repeat region.

136. The composition of claim 134, wherein the single-stranded nucleic acid comprises DNA.

137. The composition of claim 134, wherein the single-stranded nucleic acid comprises RNA.

138. A composition comprising a duplex formed between a Human Immunodeficiency Virus Type-1 (HIV-1) nucleic acid and a single-stranded nucleic acid comprising a nucleotide sequence selected from the group consisting of:
   (i) a nucleotide sequence of either strand of viral DNA from lambda bacteriophage λ-HXB$_2$ having ATCC Accession No. 40231;
   (ii) a nucleotide sequence of either strand of viral DNA from lambda bacteriophage λ-HXB$_3$ having ATCC Accession No. 40232;
   (iii) a nucleotide sequence of either strand of viral DNA from clone BH10 having ATCC Accession No. 40125;
   (iv) a nucleotide sequence of either strand of viral DNA from clone BH5 having ATCC Accession No. 40126;
   (v) a nucleotide sequence of either strand of viral DNA from clone BH8 having ATCC Accession No. 40127;
   (vi) a nucleotide sequence of either strand of viral DNA from clone pHXB3 having ATCC Accession No. 67081;
   (vii) a nucleotide sequence of either strand of viral DNA from clone pHXB-2D having ATCC Accession No. 67082;
   (viii) a nucleotide sequence of either strand of viral DNA from *E. coli* clone X10-1 having ATCC Accession No. 67083; and
   (ix) an HIV-1 nucleotide sequence from the H9/HTLV-III cell line having ATCC Accession No. CRL 8543;
      wherein the single-stranded nucleic acid does not form a duplex with HTLV-I and HTLV-II nucleic acids under conditions of stringency for hybridization under which the single-stranded nucleic acid forms a duplex with the HIV-1 nucleic acid;
      wherein the duplex is outside of a mammalian cell and outside of an HIV-1 particle;
      wherein the duplex comprises a double-stranded region and a single-stranded region on either side of the double-stranded region that is longer than the double-stranded region; and
      wherein either the duplex or the single-stranded nucleic acid is bound to a solid support.

139. The composition of claim 138, wherein the single-stranded nucleic acid comprises a nucleotide sequence which is part of an HIV-1 gag open reading frame, an HIV-1 pol open reading frame, an HIV-1 env open reading frame or part of an HIV-1 long terminal repeat region.

140. The composition of claim 138, wherein the single-stranded nucleic acid comprises DNA.

141. The composition of claim 138, wherein the single-stranded nucleic acid comprises RNA.

142. A composition comprising:
   a compound selected from the group consisting of sodium saline citrate, formamide, and dextran sulfate; and
   a duplex formed between a Human Immunodeficiency Virus Type-1 (HIV-1) nucleic acid and a single-stranded nucleic acid comprising a nucleotide sequence selected from the group consisting of:
   (i) a nucleotide sequence of either strand of viral DNA from lambda bacteriophage λ-HXB$_2$ having ATCC Accession No. 40231;
   (ii) a nucleotide sequence of either strand of viral DNA from lambda bacteriophage λ-HXB$_3$ having ATCC Accession No. 40232;
   (iii) a nucleotide sequence of either strand of viral DNA from clone BH10 having ATCC Accession No. 40125;
   (iv) a nucleotide sequence of either strand of viral DNA from clone BH5 having ATCC Accession No. 40126;
   (v) a nucleotide sequence of either strand of viral DNA from clone BH8 having ATCC Accession No. 40127;
   (vi) a nucleotide sequence of either strand of viral DNA from clone pHXB3 having ATCC Accession No. 67081;
   (vii) a nucleotide sequence of either strand of viral DNA from clone pHXB-2D having ATCC Accession No. 67082;
   (viii) a nucleotide sequence of either strand of viral DNA from *E. coli* clone X10-1 having ATCC Accession No. 67083; and
   (ix) an HIV-1 nucleotide sequence from the H9/HTLV-III cell line having ATCC Accession No. CRL 8543;

wherein the single-stranded nucleic acid does not form a duplex with HTLV-I and HTLV-II nucleic acids under conditions of stringency for hybridization under which the single-stranded nucleic acid forms a duplex with the HIV-1 nucleic acid;

wherein the duplex is outside of a mammalian cell and outside of an HIV-1 particle;

wherein the duplex comprises a double-stranded region and a single-stranded region on either side of the double-stranded region that is longer than the double-stranded region.

143. The composition of claim 142, wherein the single-stranded nucleic acid comprises a nucleotide sequence which is part of an HIV-1 gag open reading frame, an HIV-1 pol open reading frame, an HIV-1 env open reading frame or part of an HIV-1 long terminal repeat region.

144. The composition of claim 142, wherein the single-stranded nucleic acid comprises DNA.

145. The composition of claim 142, wherein the single-stranded nucleic acid comprises RNA.

146. A composition comprising a duplex formed between a Human Immunodeficiency Virus Type-1 (HIV-1) nucleic acid and a single-stranded nucleic acid comprising a nucleotide sequence selected from the group consisting of:
(i) a nucleotide sequence of either strand of viral DNA from lambda bacteriophage λ-HXB$_2$ having ATCC Accession No. 40231;
(ii) a nucleotide sequence of either strand of viral DNA from lambda bacteriophage λ-HXB$_3$ having ATCC Accession No. 40232;
(iii) a nucleotide sequence of either strand of viral DNA from clone BH10 having ATCC Accession No. 40125;
(iv) a nucleotide sequence of either strand of viral DNA from clone BH5 having ATCC Accession No. 40126;
(v) a nucleotide sequence of either strand of viral DNA from clone BH8 having ATCC Accession No. 40127;
(vi) a nucleotide sequence of either strand of viral DNA from clone pHXB3 having ATCC Accession No. 67081;
(vii) a nucleotide sequence of either strand of viral DNA from clone pHXB-2D having ATCC Accession No. 67082;
(viii) a nucleotide sequence of either strand of viral DNA from *E. coli* clone X10-1 having ATCC Accession No. 67083; and
(ix) an HIV-1 nucleotide sequence from the H9/HTLV-III cell line having ATCC Accession No. CRL 8543;
wherein the single-stranded nucleic acid does not form a duplex with HTLV-I and HTLV-II nucleic acids under conditions of stringency for hybridization under which the single-stranded nucleic acid forms a duplex with the HIV-1 nucleic acid;
wherein the duplex is outside of a mammalian cell and outside of an HIV-1 particle;
wherein the duplex comprises a double-stranded region and a single-stranded region on either side of the double-stranded region that is longer than the double-stranded region; and
wherein the single-stranded nucleic acid is attached to a non-HIV-1 nucleic acid through a covalent bond.

147. The composition of claim 146, wherein the single-stranded nucleic acid comprises a nucleotide sequence which is part of an HIV-1 gag open reading frame, an HIV-1 pol open reading frame, an HIV-1 env open reading frame or part of an HIV-1 long terminal repeat region.

148. The composition of claim 146, wherein the single-stranded nucleic acid comprises DNA.

149. The composition of claim 146, wherein the single-stranded nucleic acid comprises RNA.

150. A nucleic acid comprising a nucleotide sequence selected from the group consisting of
(i) a nucleotide sequence of either strand of viral DNA from lambda bacteriophage λ-HXB$_2$ having ATCC Accession No. 40231;
(ii) a nucleotide sequence of either strand of viral DNA from lambda bacteriophage λ-HXB$_3$ having ATCC Accession No. 40232;
(iii) a nucleotide sequence of either strand of viral DNA from clone BH10 having ATCC Accession No. 40125;
(iv) a nucleotide sequence of either strand of viral DNA from clone BH5 having ATCC Accession No. 40126;
(v) a nucleotide sequence of either strand of viral DNA from clone BH8 having ATCC Accession No. 40127;
(vi) a nucleotide sequence of either strand of viral DNA from clone pHXB3 having ATCC Accession No. 67081;
(vii) a nucleotide sequence of either strand of viral DNA from clone pHXB-2D having ATCC Accession No. 67082;
(viii) a nucleotide sequence of either strand of viral DNA from *E. coli* clone X10-1 having ATCC Accession No. 67083; and
(ix) a Human Immunodeficiency Virus Type-1 (HIV-1) nucleotide sequence from the H9/HTLV-III cell line having ATCC Accession No. CRL 8543;
wherein the nucleic acid does not form a duplex with HTLV-I and HTLV-II nucleic acids under conditions of stringency for hybridization under which the nucleic acid forms a duplex with an HIV-1 nucleic acid; and
wherein the nucleic acid is covalently attached to a solid support.

151. The nucleic acid of claim 150, wherein the nucleic acid comprises a nucleotide sequence which is part of an HIV-1 gag open reading frame, an HIV-1 pol open reading frame, an HIV-1 env open reading frame or part of an HIV-1 long terminal repeat region.

152. The nucleic acid of claim 150, wherein the nucleic acid comprises DNA.

153. The nucleic acid of claim 150, wherein the nucleic acid comprises RNA.

154. A nucleic acid comprising a nucleotide sequence selected from the group consisting of
(i) a nucleotide sequence of either strand of viral DNA from lambda bacteriophage λ-HXB$_2$ having ATCC Accession No. 40231;
(ii) a nucleotide sequence of either strand of viral DNA from lambda bacteriophage λ-HXB$_3$ having ATCC Accession No. 40232;
(iii) a nucleotide sequence of either strand of viral DNA from clone BH10 having ATCC Accession No. 40125;
(iv) a nucleotide sequence of either strand of viral DNA from clone BH5 having ATCC Accession No. 40126;
(v) a nucleotide sequence of either strand of viral DNA from clone BH8 having ATCC Accession No. 40127;
(vi) a nucleotide sequence of either strand of viral DNA from clone pHXB3 having ATCC Accession No. 67081;
(vii) a nucleotide sequence of either strand of viral DNA from clone pHXB-2D having ATCC Accession No. 67082;
(viii) a nucleotide sequence of either strand of viral DNA from *E. coli* clone X10-1 having ATCC Accession No. 67083; and
(ix) a Human Immunodeficiency Virus Type-1 (HIV-1) nucleotide sequence from the H9/HTLV-III cell line having ATCC Accession No. CRL 8543;

wherein the nucleic acid does not form a duplex with HTLV-I and HTLV-II nucleic acids under conditions of stringency for hybridization under which the nucleic acid forms a duplex with an HIV-1 nucleic acid;

wherein the nucleic acid comprises a detectable label covalently attached to the nucleic acid; and wherein the detectable label is not an additional nucleic acid.

155. The nucleic acid of claim 154, wherein the nucleic acid comprises a nucleotide sequence which is part of an HIV-1 gag open reading frame, an HIV-1 pol open reading frame, an HIV-1 env open reading frame or part of an HIV-1 long terminal repeat region.

156. The nucleic acid of claim 154, wherein the nucleic acid comprises DNA.

157. The nucleic acid of claim 154, wherein the nucleic acid comprises RNA.

158. A nucleic acid comprising a nucleotide sequence selected from the group consisting of
   (i) a nucleotide sequence of either strand of viral DNA from lambda bacteriophage λ-HXB$_2$ having ATCC Accession No. 40231;
   (ii) a nucleotide sequence of either strand of viral DNA from lambda bacteriophage λ-HXB$_3$ having ATCC Accession No. 40232;
   (iii) a nucleotide sequence of either strand of viral DNA from clone BH10 having ATCC Accession No. 40125;
   (iv) a nucleotide sequence of either strand of viral DNA from clone BH5 having ATCC Accession No. 40126;
   (v) a nucleotide sequence of either strand of viral DNA from clone BH8 having ATCC Accession No. 40127;
   (vi) a nucleotide sequence of either strand of viral DNA from clone pHXB3 having ATCC Accession No. 67081;
   (vii) a nucleotide sequence of either strand of viral DNA from clone pHXB-2D having ATCC Accession No. 67082;
   (viii) a nucleotide sequence of either strand of viral DNA from *E. coli* clone X10-1 having ATCC Accession No. 67083; and
   (ix) a Human Immunodeficiency Virus Type-1 (HIV-1) nucleotide sequence from the H9/HTLV-III cell line having ATCC Accession No. CRL 8543;

wherein the nucleic acid does not form a duplex with HTLV-I and HTLV-II nucleic acids under conditions of stringency for hybridization under which the nucleic acid forms a duplex with an HIV-1 nucleic acid;

wherein the nucleic acid is outside of a mammalian cell and outside of a viral particle; and wherein the nucleic acid is attached to a non-HIV-1 nucleic acid through a covalent bond.

159. The nucleic acid of claim 158, wherein the nucleic acid comprises a nucleotide sequence which is part of an HIV-1 gag open reading frame, an HIV-1 pol open reading frame, an HIV-1 env open reading frame or part of an HIV-1 long terminal repeat region.

160. The nucleic acid of claim 158, wherein the nucleic acid comprises DNA.

161. The nucleic acid of claim 158, wherein the nucleic acid comprises RNA.

* * * * *